United States Patent
Hummel et al.

(10) Patent No.: US 7,727,960 B2
(45) Date of Patent: Jun. 1, 2010

(54) C5A RECEPTOR ANTAGONISTS

(75) Inventors: Gerd Hummel, Berlin (DE); Elsa Locardi, Berlin (DE); Thomas Polakowski, Berlin (DE); Dirk Scharn, Berlin (DE); Karsten Schnatbaum, Berlin (DE)

(73) Assignee: Jerini AG, Berlin (DE)

( * ) Notice: Subject to any disclaimer, the term of this patent is extended or adjusted under 35 U.S.C. 154(b) by 0 days.

(21) Appl. No.: 10/564,788

(22) PCT Filed: Jul. 19, 2004

(86) PCT No.: PCT/EP2004/008057

§ 371 (c)(1),
(2), (4) Date: Jan. 17, 2006

(87) PCT Pub. No.: WO2005/010030

PCT Pub. Date: Feb. 3, 2005

(65) Prior Publication Data

US 2006/0183883 A1    Aug. 17, 2006

(30) Foreign Application Priority Data

Jul. 17, 2003   (EP) .................................. 03016233

(51) Int. Cl.
*A61K 38/08* (2006.01)
(52) U.S. Cl. .......................... 514/17; 530/329
(58) Field of Classification Search .................. None
See application file for complete search history.

(56) References Cited

U.S. PATENT DOCUMENTS 5,387,671 A * 2/1995 Kawai et al. ................. 530/329

FOREIGN PATENT DOCUMENTS

| WO | WO 90/09162 A | 8/1990 |
|---|---|---|
| WO | WO 92/12168 A | 7/1992 |
| WO | WO 99/00406 A | 1/1999 |
| WO | WO 03/033528 A | 4/2003 |
| WO | WO 03/086448 A | 10/2003 |
| WO | WO 2004/035079 A1 | 4/2004 |

OTHER PUBLICATIONS

March et al., "Potent cyclic antagonists of the complement C5a receptor on human polymorphonuclear leukocytes. Relationships between structures and activity", Molecular Pharmacology, vol. 65, No. 4, Apr. 1, 2004, pp. 868-879.

Finch et al., "Low-Molecular-Weight Peptidic and Cyclic Antagonists of the Receptor for the Complement Factor C5a", Journal of Medicinal Chemistry, vol. 42, No. 11, Jun. 3, 1999, pp. 1965-1974.

Wong et al., "Small molecular probes for G-protein-coupled C5a receptors: conformationally constrained antagonists derived from the C terminus of the human plasma protein C5a", Journal of Medicinal Chemistry, vol. 41, No. 18, Aug. 27, 1998, pp. 3417-3425.

Demartino et al., "Arginine 206 of the C5a receptor is critical for ligand recognition and receptor activation by C-terminal hexapeptide analogs", Journal of Biological Chemistry, vol. 270, No. 27, 1995, pp. 15966-15969.

March, Darren R. et al., "Potent Cyclic Antagonists of the Complement C5a Receptor on Human Polymorphonuclear Leukocytes. Relationships between Structures and Activity," Institute for Molecular Bioscience and School of Biomedical Sciences, vol. 65, No. 4, Jan. 7, 2004, pp. 868-879.

DeMartino, Julie A. et al., "Arginine 206 of the C5a Receptor is Critical for Ligand Recognition and Receptor Activation by C-terminal Hexapeptide Analogs," The Journal of Biological Chemistry, vol. 270, No. 27, Jul. 7, 1995, pp. 15966-15969.

* cited by examiner

*Primary Examiner*—Anish Gupta
*Assistant Examiner*—Ronald T Niebauer
(74) *Attorney, Agent, or Firm*—Rothwell, Figg, Ernst & Manbeck, P.C.

(57) ABSTRACT

The invention relates to a C5a receptor antagonist of structure (I), wherein X1 is a radical having a mass of about 1-300 and stands for R5-, R5-CO—, R5-N(R6)-CO—, R5-O—CO—, R5-SO$_2$—, R5-N(R6)-SO$_2$—, R5-N(R6)-, R5-N(R6)-CS—, R5-N(R6)-C(NH)—, R5-CS—, R5-P(O)OH—, R5-B (OH)— or R5-CH=N—O—CH$_2$—CO—, wherein R5/R6 represent H, F, hydroxy, alkyl, substituted alkyl, cycloalkyl, substituted cycloalkyl, heterocyclyl, substituted heterocyclyl, arylalkyl, substituted arylalkyl, aryl, substituted aryl, heteroaryl, substituted heteroaryl, acyl, substituted acyl, alkoxy, alkoxyalkyl, substituted alkoxyalkyl, aryloxyalkyl or substituted aryloxyalkyl; X2=radical (biological bonding properties of a mimicrying phenylalanine unit); X3/X4=spacer (amino acids, amino-acid analogs and amino-acid derivatives); X5=radical (biological bonding properties of a mimicrying cyclohexylalanine or homoleucine unit); X6=radical (biological bonding properties of a mimicrying tryptophan unit); X7=radical (biological bonding properties of a mimicrying norleucine or phenylalanine unit), a chemical bond being formed between X3 and X7.

2 Claims, 1 Drawing Sheet

C5A RECEPTOR ANTAGONISTS

CROSS REFERENCE TO RELATED APPLICATION

This application is a 35 USC §371 National Phase Entry Application from PCT/EP2004/008057, filed Jul. 19, 2004, and designating the United States.

The present invention is related to antagonist of the C5a receptor and the use thereof.

PRIOR ART

Besides the adaptive immune system another—developmental much older—system for the defence against infection exists. This system is called complement system and consists of more than 30 soluble and membrane bound proteins. The complement system can be activated without or together with the adaptive immune system to eliminate, e.g., pathogenic bacteria. An uncontrolled activation or inadequate regulation of the complement system is related to a number of inflammatory diseases like septic shock, reperfusion injury, rheumatoid arthritis, transplant rejection, acute respiratory distress syndrome (ARDS), systemic lupus erythematosis (SLE), and glomerulonephritis. Numerous overviews over the relation between the complement system and diseases are published (e.g. Kirschfink 1997 Immunopharmacology 38: 51-62; Markides 1998 Pharmacological Reviews 50: 59-87, Walport 2001 The New England Journal of Medicine 344: 1140-1144, Walport 2001 The New England Journal of Medicine 344: 1058-66).

Activation of the complement system takes place via three different pathways. They are called classical, alternative, and mannose-binding lectin (MBL) way. All pathways proceed via the sequential processing and thus activation of pro-forms of proteases. As each activated protease can cleave and therefore activate the next pro-form, an amplification of the initial reaction is obtained. This is similar to the clotting cascade. An overview over the complement system is given by Sim and Laich (2000 Biochemical Society Transactions 28: 545-550).

Some of the most important proteins that are generated upon complement activation are C3a, C3b, C5a, and C5b. These proteins will be discussed in detail.

C3b is an essential part of a central protease of the complement cascade, the C5 convertase. C3b is part of the C5 convertase from both, the classical and alternative pathway of complement activation. The MLB pathway is proceeding via the convertases of the classical pathway, too. The C5 convertase is responsible for the progress of the complement cascade and catalyses the cleavage of C5. Additionally, C3b is covalently attached to the surface of, e. g., bacteria which are thus more prone to phagocytosis by macrophages. Similar processes are described for immune complex clearance.

C3a is the smaller fragment that is produced in addition to C3b upon cleavage of C3. C3a is a comparatively weak chemokine and belongs to the anaphylatoxins.

C5b is formed by cleavage of C5. This cleavage product is the starting point for the formation of the membrane attack complex (MAC). The MAC forms a pore which perforates both plasma membranes of bacteria and endogenous cells. Due to the pore formation the perforated cells can be lysed.

C5a is the 74 amino acid N-terminal cleavage product of the α-chain of plasma protein C5 and is released by the activity of the C5 convertase. C5a is bound by its receptor which is referred to as C5a receptor C5aR1 or CD88, with high affinity and triggers a number of pro-inflammatory effects. It is one of the most potent chemokines and belongs as C3a to the anaphylatoxins. The C5aR can be found on many cells. This receptor is particularly found on neutrophils, macrophages, smooth muscle cells, and endothelial cells.

C5a release is thought to be directly or indirectly responsible for many diseases. Examples are sepsis (Huber-Lang et al. 2001 Faseb Journal 15: 568-570), multiple sclerosis (Mullerladner et al. 1996 Journal of Neurological Science 144: 135-141), reperfusion injury (Riley et al. 2000 Journal of Thoriacic and Cardiovascular Surgery 120: 350-358), psoriasis (Bergh et al. 1993 Archives of Dermatological Research 285: 131-134), rheumatoid arthritis (Woodruff et al. 2002 Arthritis and Rheumattism 46: 2476-85) und immune complex associated diseases in general (Heller et al. 1999 Journal of Immunology 163: 985-994). An overview over C5a related diseases is found in Köhl (2001 Molecular Immunology 38: 51-62).

Although it is obvious that C5a is responsible for many of the symptoms of inflammatory diseases, until today no drug directly aiming at the interaction between the receptor and its ligand was approved. The C5aR is a particularly interesting target. This is especially the case due to the finding that mice lacking the receptor do not show an unusual phenotype (Hopken et al. 1996 Nature 383: 86-89). This means that the complement cascade with its useful functions for defence against pathogens (MAC formation) and immune complex clearance can still proceed in an unhindered manner even when the receptor is totally inactivated.

The development of a specific C5a receptor antagonist also referred to herein as C5aR antagonist, was part of past programs. Among others, small molecules have been looked for. Examples for such molecules are L-156602 (Merck), RPR120033 (Rhone-Poulenc), W-54011 (Mitsubishi Pharma), and NGD 2000-1 (Neurogen). All currently known inhibitors with a molecular weight of <500 g/mol have at least one of the following drawbacks: low specificity, agonistic properties, too low affinity, poor solubility, inadequate metabolic stability, or inhibition of P450 enzymes.

Another way for the development of C5aR inhibitors is based on the use of recombinant proteins. Examples for such protein based antagonists are CGS 32359 (Ciba-Geigy, Pellas et al. 1998 Journal of Immunology 160: 5616-5621), ΔpIII-A8 (Heller et al. 1999 Journal of Immunology 163: 985-994) and antibodies, which can be of recombinant or non-recombinant origin (Huber-Lang et al. 2001 Faseb Journal 15: 568-570). These C5aR antagonists are proteins and therefore expensive in production. They have comparatively high affinities and specificities but have the drawback of pronounced immunogenicity. In addition, proteins can be effectively administered only by costly procedure such as, e. g., injection.

The C-terminal sequence information of C5a was used for the development of peptidic C5aR antagonists. Peptides as therapeutically useable antagonists of the C5aR are advantageous over protein therapeutics because of lower production costs, reduced immunogenicity, and high plasma stability. In addition they are more specific than most of the currently known small molecules. Many peptidic antagonists are described in the literature. A common feature of nearly all C5aR antagonists is their origin in the C-terminus of C5a. Examples for these peptidic C5aR antagonists or partial agonists are found in the following patents and patent applications: U.S. Pat. No. 4,692,511, U.S. Pat. No. 5,663,148, WO 90/09162, WO 92/11858, WO 92/12168, WO 92/21361, WO 94/07518, WO 94/07815, WO 95/25957, WO 96/06629, WO 99/00406 und WO 99/13899, WO 03/033528. In De Martino et al. (1995 Journal of Biological Chemistry 270: 15966-15969) a first attempt for a structural explanation of the importance of the C-terminal arginine in peptidic C5aR antagonists was made. It is shown on page 15967 that the C-terminal arginine is very important for the affinity and activity of the described peptides. It is pointed out that both the positively charged guanidinium group and the negative charge of the carboxy group are important for the affinity improving properties of arginine. The impact of both residues was further characterized (p. 15966), whereby guanidinium group is responsible for the energy releasing contact with the receptor while the free carboxy group annuls the interference with Arg-206 of the receptor.

Nearly all of the C5aR binding peptides described to date have the positively charged amino acid arginine at the C-terminus. Sequences of these peptides are published in both scientific literature (Finch et al. 1999 Journal of Medicinical Chemistry 42: 1965-1974; Wong et al. 1999 IDrugs 2: 686-693; Psczkowski et al. 1999 Pharmacology 128: 1461-1466) and in the patent applications and patents recited above.

In WO 90/09162 38 peptidic inhibitors are presented along with their $IC_{50}$ values (example 2, 13, 23, 31, 91, 106, 111, 117, 131, 150, 165, 182, 188, 202, 213, 220, 229, 245, 247, 249, 279, 282, 295, 296, 305, 316, 338, 348, 377, 402, 404, 409, 421, 424, 432, 445, 455, 460). Out of these peptides 37 peptides have a C-terminal arginine and only one peptide has a different C-terminal amino acid (tyrosine, example 305). The amino acid sequence of example 305 of WO 90/09162 is Ac-Phe-Lys-Ala-Cha-Ala-Leu-ala-Tyr-OH [SEQ ID NO: 1] and an $IC_{50}$ value of 0.17 µM was shown for the binding. This is more than a ten-fold decrease in the affinity compared to other described peptides with a C-terminal Arg (e.g. Ac-Phe-Lys-Ala-Cha-Ala-Leu-N-Methyl(D)ala-Arg-OH (example 296) [SEQ ID NO: 2] and (N-Ethyl)Phe-Lys-Ala-Cha-Ala-Leu-N-Methyl(D)ala-Arg-OH (example 402) [SEQ ID NO: 3] with an $IC_{50}$ value of 0.012 µM and 0.011 µM, respectively). In a functional assay as used in this application the tyrosine containing compound shows an $IC_{50}$ value of 1.3 µM. Functional assays are generally more predictive for in vivo activities than binding assays. It becomes thus clear that the use of tyrosine as C-terminal amino acid did not lead to a peptide which could be used for the development of a pharmaceutically useable C5aR antagonist. This is possibly also the reason for the author not to describe further tyrosine containing peptides together with values for their activity.

In WO 92/12168 additional 20 peptides are described along with their $IC_{50}$ values (binding to C5aR). 19 out of these peptides have a terminal arginin which can be in either the D or the L form. One peptide has a C-terminal phenylbutanoyl residue which could interact via hydrophobic interactions. This peptide (example 170) has the sequence (N-Methyl)Phe-Lys-Pro-cha-Phe-Phenylbutanoyl [SEQ ID NO: 4] and is said to have an IC50 value of only 2.6 µM which does not seem to be sufficient for use as a drug. An immediate comparison between the C-terminal argininyl and phenylbutanoyl from this application is not possible since a directly comparable structure was not disclosed. Example 105 from WO 92/12168 ((N-Methyl)Phe-Lys-Pro-cha-ψ{CH$_2$- N(CH$_2$CH$_2$C$_6$H$_5$)}-Arg-OH) [SEQ ID NO: 5] is the best suited compound for comparison with example 170. The $IC_{50}$ value for this hexamere is 0.36 µM. This means the substitution of Arg leads to an activity decrease in this example, too.

Among the 22 examples of WO 94/07518 for which $IC_{50}$ values have been presented, all peptides have a C-terminal arginine.

The $IC_{50}$ values indicated in WO 90/09162, WO 92/12168, and WO 94/07518 are derived from measurements with isolated membranes from polymorphonuclear neutrophilic granulocytes (PMN membranes) because at the time when these experiments were performed, C5a overexpressing cells could not be generated. Results from these measurements do not reflect the affinity of the compounds to whole cells. The compounds have a reduced affinity to receptors on whole cells (Kawai et al. 1991 Journal of Medicinal Chemistry 34: 2068-71; Rollins et al. 1988 Journal of Biological Chemistry 263: 520-526). It is, however, more meaningful to measure the biological activity rather than the binding of the antagonist to the receptor. Often such functional assays are used for G protein coupled receptors.

The examples presented in international patent applications WO 95/25957 und WO 96/06629 for which $IC_{50}$ values are known, are without any exception peptides containing a C-terminal arginine. This is also true for the papers of Wong et al. (Wong et al. 1998 Journal of Medicinal Chemistry 41: 3417-3425) and Finch et al. (Finch et al. 1999 Journal of Medicinal Chemistry 42: 1965-1974). In these papers 6 and 31, respectively, linear and cyclic 6 or 7-mer peptides are described.

In WO 99/00406 a number of cyclic and linear peptidic inhibitors are described. Their common feature is the C-terminal arginine. A model of the pharmacophore which is outlined in WO 99/00406 is directly pointing towards the required positive charge which can be realised by arginine (WO 99/00406 page 12, line 13ff).

The C-terminal arginine is also of crucial importance for the activity in the naturally occurring C5a. The agonistic potency is reduced by a factor 10 to 1000, depending on the used assay system, when this arginine is cleaved off by carboxypeptidases (C5a-desArg) (Gerard und Gerard 1994 Annual Reviews in Immunology 12: 775-808).

In WO 03/033528 single substitutions of various amino acids in the molecule Ac-Phe[Orn-Pro-cha-Trp-Arg](compound 1) [SEQ ID NO: 6] are reported. A decrease of the affinity to the C5aR and a decrease in antagonistic potency is described for the substitution of the Arg with homoarginine (compound 44), citrulline (compound 45), lysine (Verbindung 47), or canavanine (compound 47). The reported $IC_{50}$ values as a measure for affinity are 1.36 µM (44), 6 µM (45), and 24 µM (47), respectively. No $IC_{50}$ value is reported for canavanine. This points to a significant decrease in the affinity to the C5areceptor due to these arginine substitutions ($IC_{50}$ of 1 is 0.45 µM). Apart from the effects of charged arginine substitutions (homoarginine and lysine), in particular the strong decrease in binding strength upon exchange of the charged arginine (0.45 µM) by the uncharged citrulline (6 µM) is remarkable. The antagonistic activity is reduced even more (Arg: 0.028 µM, Cit: 0.690 µM). The significance of a positive charge is thus underlined by the fact that the guanidinium group (Arg) and the urea group (Cit) are bioisosteres and need a comparable space. This also reflects that the size of the side chain itself is not sufficient as a criterium for predicting the activity. WO 03/033528 sets forth that the arginine (1) substitution to citrulline (45) results in a compound with allegedly remarkable antagonistic properties (p. 44, line 28ff). However, the cut off rate for what is remarkable, is chosen arbitrarily and the significant 24-fold drop in activity underlines the in the prior art well known importance of the C-terminal arginine in the peptidic C5aR antagonists. The citrulline containing peptide 45 is by the way the only peptide that has no positive net charge under physiological conditions and for which a value for binding and the antagonistic activity is reported in WO 03/033528.

In a review of Morikis and Lambris (2002 Biochemical Society Transactions 30: 1026-1036) the importance of the arginine for the affinity of agonists and antagonists to the C5a receptor is stressed.

It is apparent that the prior art requires a C-terminal localized positive charge for peptidic and peptidomimetic C5a ligands with noteworthy inhibitory activity ($IC_{50}$<200 nM). This charge is realized usually by arginine.

The problem underlying the present application is the provision of C5aR antagonists. Another problem underlying the present invention is the provision of drugs, that can be used for the treatment of diseases, in which the C5a receptor is involved in a causal, indirect or symptomatic manner.

In a first aspect of the invention the problem is solved by a compound, preferably a C5a receptor antagonist, with the following structure:

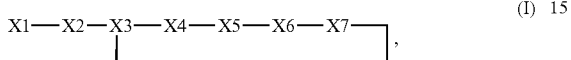
(I)

whereby

X1 is a radical having a mass of about 1-300 and whereby X1 is preferably chosen from the group including R5-, R5-CO—, R5-N(R6)-CO—, R5-O—CO—, R5-$SO_2$—, R5-N(R6)-$SO_2$—, R5-N(R6)-, R5-N(R6)-CS—, R5-N(R6)-C(NH)—, R5-CS—, R5-P(O)OH—, R5-B(OH)—, R5-CH=N—O—$CH_2$—CO—, in which R5 and R6 individually and independently are chosen from the group comprising H, F, hydroxy, alkyl, substituted alkyl, cycloalkyl, substituted cycloalkyl, heterocyclyl, substituted heterocyclyl, arylalkyl, substituted arylalkyl, aryl, substituted aryl, heteroaryl, substituted heteroaryl, acyl, substituted acyl, alkoxy, alkoxyalkyl, substituted alkoxyalkyl, aryloxyalkyl and substituted aryloxyalkyl, X2 is a radical that mimics the biologic binding characteristics of a phenylalanine unit, X3 and X4 individually and independently are a spacer, whereby the spacer is preferably selected from the group comprising amino acids, amino acid analogs and amino acid derivates, X5 is a radical that mimics the biologic binding characteristics of a cyclohexylalanine or homoleucine unit, X6 is a radical that mimics the biologic binding characteristics of a tryptophane unit, X7 is a radical that mimics the biologic binding characteristics of a norleucine or phenylalanine unit, a chemical bond is formed between X3 and X7, and the lines—in formula (I) indicate chemical bonds, whereby the chemical bond individually and independently is selected from the group comprising covalent bonds, ionic bonds and coordinative bonds, whereby preferably the bond is a chemical bond and more preferably the chemical bond is a bond selected from the group comprising amide bonds, disulfide bonds, ether bonds, thioether bonds, oxime bonds and aminotriazine bonds.

In an embodiment X3 and X7 are individually an amino acid, amino acid analog or amino acid derivative, whereby the chemical bond between X3 and X7 is formed under participation of at least one moiety of X3 and X7, and the moieties for X3 and X7 are individually and independently selected from the group comprising the C terminus, the N terminus and the respective side chain of the amino acid.

In an embodiment X1 is a radical with a mass of about 1-300, whereby the radical is preferably selected from the group comprising R5, R5-CO—, R5-N(R6)-CO—, R5-O—CO—, R5-$SO_2$—, R5-N(R6)-C(NH)—, whereby R5 and R6 are individually and independently selected from the group comprising H, alkyl, substituted alkyl, cycloalkyl, substituted cycloalkyl, heterocyclyl, substituted heterocyclyl, aryl and substituted aryl;

X2 and X6 are individually and independently an aromatic amino acid, a derivative or an analogon thereof;

X5 and X7 are individually and independently a hydrophobic amino acid, a derivative or an analogon thereof.

In an embodiment X2, X5, X6 and X7 individually and independently have the following structure:

(III)

wherein

X is C(R4) or N,

R1 is optionally present and if present then R1 is a radical, that is selected from the group comprising >N-R1B, >C(R1B)(R1D) and >O, whereby R1B and R1D are individually and independently selected from the group comprising H, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, cycloalkylalkyl and substituted cycloalkylalkyl;

R2 is optionally present and if R2 is present then R2 is a radical that is selected from the group comprising >C=O, >C=S, >$SO_2$, >S=O, >C=NH, >C=N—CN, >PO(OH), >B(OH), >$CH_2$, >$CH_2$CO, >CHF and >$CF_2$;

R4 is a radical, whereby the radical is selected from the group comprising H, F, $CH_3$, $CF_3$, alkyl and substituted alkyl;

the binding of structure (III) to the moieties X1 and X3, X4 and X6, X5 and X7, and X6 and X3 is preferably carried out via R1 and R2;

for X2 and for X6 individually and independently R3 is a radical, in which the radical comprises an aromatic group and is selected from the group comprising aryl, substituted aryl, heteroaryl, substituted heteroaryl, arylalkyl, substituted arylalkyl, heteroarylalkyl, substituted heteroarylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl; and for X5 and for X7 individually and independently R3 is a radical, whereby the radical comprises an aliphatic or aromatic group and preferably is seletected from the group comprising alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl.

In a preferred embodiment a ring is formed under participation of R3 and R4.

In an embodiment, for X2 and for X6 individually and independently R3 is selected from the group comprising phenyl, substituted phenyl, benzyl, substituted benzyl, 1,1-diphenylmethyl, substituted 1,1-diphenylmethyl, naphthylmethyl, substituted naphthylmethyl, thienylmethyl, substituted thienylmethyl, benzothienylmethyl, substituted benzothienylmethyl, imidazolylmethyl, substituted imidazolylmethyl, indolylmethyl and substituted indolylmethyl.

In an embodiment, for X5 and for X7 individually and independently R3 is selected from the group comprising C3-C5-alkyl, substituted C3-C5-alkyl, C5-C7-cycloalkyl, substituted C5-C7-cycloalkyl, C5-C7-cycloalkylmethyl, substituted C5-C7-cycloalkylmethyl, cycloalkylethyl, substituted cycloalkylethyl, benzyl, substituted benzyl, phenylethyl, naphthylmethyl, thienylmethyl, propenyl, propinyl, methylthioethyl, imidazolylmethyl, substituted imidazolylmethyl, indolylmethyl and substituted indolylmethyl.

In an embodiment X1 is selected from the group comprising H, acetyl, propanoyl, butanoyl, benzoyl, fluoromethylcarbonyl, difluoromethylcarbonyl, phenyl, oxycarbonyl, methyl-oxycarbonyl, phenyl-aminocarbonyl, methyl-aminocarbonyl, phenyl-sulfonyl, 2,6-dioxo-hexahydro-pyrimidine-4-carbonyl and methyl-sulfonyl.

In an embodiment X2 is a derivative of an amino acid that is selected from the group comprising phenylalanine, 2-fluoro-phenylalanine, 3-fluoro-phenylalanine, 4-fluoro-phenylalanine, 2-chlorophenylalanine, 3-chlorophenylalanine, 4-chlorophenylalanine, 1-naphtylalanine, 2-thienylalanine, 3-thienylalanine, 3,3-diphenylalanine, tyrosine, tryptophane, histidine and each respective derivatives thereof;

or X2 and X1 taken together are PhCH$_2$CH$_2$CO— or PhCH$_2$—;

X6 is a derivative of an amino acid, that is selected from the group comprising tryptophane, phenylalanine, tyrosine, histidine, 1-naphtylalanine, benzothienylalanine, 2-aminoindan-2-carboxylic acid, 2-thienylalanine, 3-thienylalanine, 2-fluoro-phenylalanine, 3-fluoro-phenylalanine, 4-fluoro-phenylalanine, 2-chlorophenylalanine, 3-chlorophenylalanine, 4-chlorophenylalanine and respective derivatives thereof;

X5 is a derivative of an amino acid that is seletected from the group comprising D-cyclohexylalanine, D-cyclohexylglycine, D-homo-cyclohexylalanine, D-homoleucine, D-cysteine(tBu), D-cysteine(iPr), octahydroindol-2-carboxylic acid, 2-methyl-D-phenylalanine and respective derivatives thereof; and X7 is a derivative of an amino acid that is seletected from the group comprising norvaline, norleucine, homo-leucine, leucine, isoleucine, Valine, cysteine, cysteine(Me), cysteine(Et), cysteine(Pr), methionine, allylglycine, propargylglycine, cyclohexylglycine, cyclohexylalanine, phenylalanine, tyrosine, tryptophane, histidine, 1-naphtylalanine, 2-thienylalanine, 3-thienylalanine and respective derivatives thereof.

In an embodiment X1 and/or X4 comprise one or more groups that improve water solubility, whereby the water solubility improving group is seletected from the group comprising hydroxy, keto, carboxamido, ether, urea, carbamate, amino, substituted amino, Guanidino, pyridyl and carboxyl.

In a second aspect of the invention the problem is solved by a compound, preferably a C5a receptor antagonist, having the following structure:

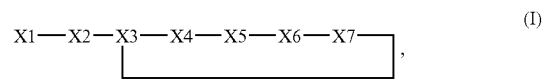

whereby X1-X3 and X5-X7 are defined in accordance with the first aspect and whereby X4 is a cyclic or a non-cyclic amino acid, whereby the cyclic amino acid is seletected from the group comprising proline, pipecolinic acid, azetidine-2-carboxylic acid, tetrahydroisochinoline-3-carboxylic acid, tetrahydroisochinoline-1-carboxylic acid, octahydroindole-2-carboxylic acid, 1-aza-bicyclo-[3.3.0]-octane-2-carboxylic acid, 4-phenyl-pyrrolidine-2-carboxylic acid, cis-Hyp and trans-Hyp, and whereby the non-cyclic amino acid is selected from the group comprising Ser, Gln, Asn, Cys (O$_2$CH$_2$CH$_2$CONH$_2$), Arg, Hyp (COCH$_2$OCH$_2$CH$_2$OCH$_2$CH$_2$OCH$_3$), Hyp(CONH—CH$_2$CH(OH)—CH$_2$OH) and respective derivatives thereof and respective analogs thereof; and the lines—in formula (I) indicate chemical bonds, whereby the chemical bond is individually and independently selected from the group comprising covalent bonds, ionic bonds and coordinative bonds, whereby preferably the bond is a chemical bond and more preferably the chemical bond is a bond selected from the group comprising amide bonds, disulfide bonds, ether bonds, thioether bonds, oxime bonds and aminotriazine bonds.

In an embodiment the amino acid represented by X4 is preferably selected from the group comprising proline, pipecolinic acid, azetidine-2-carboxylic acid, tetrahydroisochinoline-3-carboxylic acid, tetrahydroisochinoline-1-carboxylic acid, octahydroindole-2-carboxylic acid, 1-aza-bicyclo-[3.3.0]-octane-2-carboxylic acid, 4-phenyl-pyrrolidine-2-carboxylic acid, Hyp, Ser, Gln, Asn, Cys (O$_2$CH$_2$CH$_2$CONH$_2$) and Arg.

In an embodiment X2 is a derivative of an amino acid that is selected from the group comprising phenylalanine, 2-fluoro-phenylalanine, 3-fluoro-phenylalanine, 4-fluoro-phenylalanine, 2-chlorophenylalanine, 3-chlorophenylalanine, 4-chlorophenylalanine, 1-naphtylalanine, 2-thienylalanine, 3-thienylalanine, 3,3-diphenylalanine, tyrosine, tryptophane, histidine and respective derivatives thereof;

or X2 and X1 taken together are PhCH$_2$CH$_2$CO— or PhCH$_2$—;

X6 is a derivative of an amino acid that is selected from the group comprising tryptophane, phenylalanine, tyrosine, histidine, 1-naphtylalanine, benzothienylalanine, 2-aminoindane-2-carboxylic acid, 2-thienylalanine, 3-thienylalanine, 2-fluoro-phenylalanine, 3-fluoro-phenylalanine, 4-fluoro-phenylalanine, 2-chlorophenylalanine, 3-chlorophenylalanine, 4-chlorophenylalanine and respective derivatives thereof;

X5 is a derivative of an amino acid that is selected from the group comprising D-cyclohexylalanine, D-cyclohexylglycine, D-homo-cyclohexylalanine, D-homoleucine, D-cysteine(tBu), D-cysteine(iPr), octahydroindole-2-carboxylic acid, 2-methyl-D-phenylalanine and respective derivatives thereof; and X7 is a derivative of an amino acid that is selected from the group comprising norvaline, norleucine, homo-leucine, leucine, isoleucine, Valine, cysteine, cysteine(Me), cysteine(Et), cysteine(Pr), methionine, allylglycine, propargylglycine, cyclohexylglycine, cyclohexylalanine, phenylalanine, tyrosine, tryptophane, histidine, 1-naphtylalanine, 2-thienylalanine, 3-thienylalanine and respective derivatives thereof.

In a third aspect of the invention the problem is solved by a compound, preferably a C5a receptor antagonist, having the following structure:

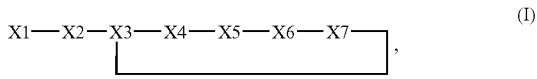

(I)

whereby X1-X2 and X4-X7 are defined in accordance with the first and/or the second aspect of the present invention and whereby X3 has the following structure

(IV)

wherein

X is C(R4) or N,

R1 is optionally present and if R1 is present then R1 is a radical which is selected from the group comprising >N-R1B, >C(R1B)(R1D) and >O, whereby R1B and R1D are individually and independently selected from the group comprising H, alkyl, substituted alkyl, cycloalkyl, substituted cycloalkyl, heterocyclyl, substituted heterocyclyl, aryl, substituted aryl, heteroaryl, substituted heteroaryl, arylakyl, substituted arylalkyl, cycloalkylalkyl and substituted cycloalkylalkyl;

R2 is optionally present and if R2 is present then R2 is a radical that is selected from the group comprising >C=O, >C=S, >SO₂, >PO(OH), >B(OH), >CH₂, >CH₂CO, >CHF and >CF₂;

R4 is a radical, whereby the radical is selected from the group comprising H, F, CF₃, alkyl and substituted alkyl;

the binding of structure (IV) to the moieties X2 and X4 preferably takes place via R1 and R2;

R3 is a radical, whereby the radical is selected from the group comprising H, alkyl, substituted alkyl, cycloalkyl, substituted cycloalkyl, heterocyclyl, substituted heterocyclyl, aryl, substituted aryl, heteroaryl, substituted heteroaryl, cycloalkylalkyl, substituted cycloalkylalkyl, heterocyclylalkyl, substituted heterocyclylalkyl, arylalkyl, substituted arylalkyl, heteroarylalkyl and substituted heteroarylalkyl.

Y is optionally present and if Y is present then Y is a radical that is selected from the group comprising —N(YB)—, —O—, —S—, —S—S—, —CO—, —C=N—O—, —CO—N(YB)— and

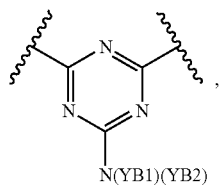

whereby YB, YB1 and YB2 are individually and independently selected from the group comprising H, alkyl, substituted alkyl, cycloalkyl, substituted cycloalkyl, heterocyclyl, substituted heterocyclyl, aryl, substituted aryl, heteroaryl, substituted heteroaryl, arylakyl, substituted arylalkyl, cycloalkylalkyl and substituted cycloalkylalkyl.

In an embodiment R3 is a radical selected from the group comprising methyl, ethyl, propyl, butyl, benzyl and

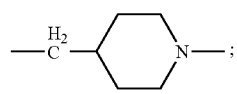

Y is optionally present and if Y is present then Y is a radical selected from the group comprising —N(YB)—, —O—, —S— and —S—S—, and YB is preferably defined in accordance with the third aspect.

In an embodiment X2 is a derivative of an amino acid selected from the group comprising phenylalanine, 2-fluoro-phenylalanine, 3-fluoro-phenylalanine, 4-fluoro-phenylalanine, 2-chlorophenylalanine, 3-chlorophenylalanine, 4-chlorophenylalanine, 1-naphtylalanine, 2-thienylalanine, 3-thienylalanine, 3,3-diphenylalanine, tyrosine, tryptophane, histidine and respective derivatives thereof;

or X2 and X1 taken together are PhCH₂CH₂CO— or PhCH₂—;

X6 is a derivative of an amino acid selected from the group comprising tryptophane, phenylalanine, tyrosine, histidine, 1-naphtylalanine, benzothienylalanine, 2-aminoindane-2-carboxylic acid, 2-thienylalanine, 3-thienylalanine, 2-fluoro-phenylalanine, 3-fluoro-phenylalanine, 4-fluoro-phenylalanine, 2-chlorophenylalanine, 3-chlorophenylalanine, 4-chlorophenylalanine and respective derivatives thereof;

X5 is a derivative of an amino acid selected from the group comprising D-cyclohexylalanine, D-cyclohexylglycine, D-homo-cyclohexylalanine, D-homoleucine, D-cysteine (tBu), D-cysteine(iPr), octahydroindole-2-carboxylic acid, 2-methyl-D-phenylalanine and respective derivatives thereof; and X7 is a derivative of an amino acid selected from the group comprising norvaline, norleucine, homo-leucine, leucine, isoleucine, valine, cysteine, cysteine(Me), cysteine(Et), cysteine(Pr), methionine, allylglycine, propargylglycine, cyclohexylglycine, cyclohexylalanine, phenylalanine, tyrosine, tryptophane, histidine, 1-naphtylalanine, 2-thienylalanine, 3-thienylalanine and respective derivatives thereof.

In an embodiment of any of the first to the third aspect of the present invention X3 is a derivative of an amino acid selected from the group comprising alpha-amino-glycine, alpha-beta-diaminopropionic acid (Dap), alpha-gamma-diaminobutyric acid (Dab), ornithine, lysine, homolysine, Phe (4-NH₂), 2-amino-3-(4-piperidinyl)propionic acid and 2-amino-3-(3-piperidinyl)propionic acid, and the amino acid is derivatized at the side chain.

In a fourth aspect of the invention the problem is solved by a compound, preferably a C5a receptor antagonist, preferably according to any of the first to the fourth aspect of the present invention, having the following structure:

(V)

[Structure of formula V showing cyclic peptide with labels A, B, C1, C2, D, E, F, Z1, Z3, NH groups and carbonyls]

whereby

A is selected from the group comprising H, NH$_2$, NHalkyl, Nalkyl2, NHacyl and OH, B is selected from the group comprising CH2(aryl), CH(aryl)2, CH2(heteroaryl), substituted CH2(aryl), aryl, substituted aryl and heteroaryl, C1 and C2 are individually and independently selected from the group comprising alkyl and substituted alkyl, whereby between C1 and C2 optionally a bond can be formed, D is selected from the group comprising alkyl, cycloalkyl, CH2(cycloalkyl), CH2CH2(cycloalkyl), CH2Ph(2-Me) and CH2-S-alkyl, E is selected from the group comprising CH2(aryl), substituted CH2(aryl) and CH2(heteroaryl), F is selected from the group comprising alkyl, CH2-S-alkyl, CH2CH2-S-Me, CH2CH=CH2, CH—CCH, cyclohexyl, CH2cyclohexyl, CH2Ph, CH2naphtyl, CH2thienyl, Z1 is selected from the group comprising (CH2)nNH with n=1, 2, 3, 4, (CH2)3O, (CH2)2O, (CH2)4, (CH2)3, CH2Ph(4-NH) and CH2(4-piperidinyl), and Z3 is optionally present and if Z3 is present then it is selected from the group comprising CO and CH2.

The individual moieties of this embodiment of the compound according to the present invention as depicted in formula (V), can be linked to the moieties of the compounds according to the present invention as of formula (I) as follows:

X1-X2 is

[Structure showing B, A and aldehyde group]

X3 is

[Structure showing NH, Z1 and aldehyde group]

X4 is

[Structure showing C2, C1, N and aldehyde group]

X5 is

[Structure showing NH-D with aldehyde]

X6 is

[Structure showing NH, E with carbonyl]

and X7 is

[Structure showing NH, F with carbonyl]

In an embodiment of the fourth aspect A is selected from the group comprising H, NH2, NHEt, NHAc, OH, B is selected from the group comprising CH2Ph, CH2Ph(4-F), CH(Ph)2, CH2thienyl, CH2naphtyl, phenyl, Ph(4-F) and thienyl, C1 is selected from the group comprising H and methyl, C2 is selected from the group comprising methyl and CH2OH, or if C1 and C2 are connected by a bond, the resulting structure is selected from the group comprising —(CH2)2-, —(CH2)3-, —(CH2)4- and —CH$_2$CH(OH)CH2-.

D is selected from the group comprising CH2CH2iPr, CH2iPr, cyclohexyl, CH2cyclohexyl, CH2CH2cyclohexyl, CH2Ph(2-Me), CH2-S-tBu and CH2-S-iPr, E is selected from the group comprising CH2Ph, CH2Ph(2-Cl), CH2Ph(3-Cl), CH2Ph(4-Cl), CH2Ph(2-F), CH2Ph(3-F), CH2Ph(4-F), CH2indolyl, CH2thienyl, CH2benzothienyl and CH2naphtyl, F is selected from the group comprising (CH2)3CH3, (CH2)2CH3, (CH2)2-iPr, CH2-ipr, iPr, CH2-S-Et, CH2CH2-S-Me, CH2CH=CH2, CH2-CCH and cyclohexyl, Z1 is selected from the group comprising (CH2)nNH with n=1, 2, 3, 4, (CH2)3O, CH2Ph(4-NH) and CH2(4-piperidinyl), and Z3 is optionally present, and if Z3 is present, then it is selected from the group comprising CO and CH2.

In a fifth aspect of the invention the problem is solved by a compound, preferably a C5a receptor antagonist, whereby the compound has the following structure:

13

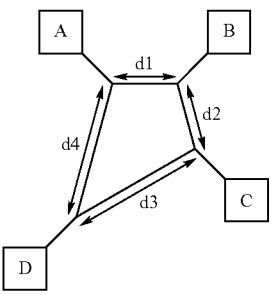

whereby d1, d2, d3 and d4 represent the distances of A, B, C and D in at least one energetically accessible conformer of the compound and have the following values:

d1=5.1±1.0 Å d2=11.5±1.0 Å d3=10.0±1.5 Å d4=6.9±1.5 Å

A and C are individually and independently a hydrophobic radical, whereby the hydrophobic radical is selected from the group comprising alkyl, cycloalkyl, heterocyclyl, aryl and heteroaryl;

B and D are individually and independently an aromatic or a heteroaromatic radical, whereby preferably the aromatic radical is aryl, and preferably the heteroaromatic radical is heteroaryl.

In an embodiment A and C are individually and independently selected from the group comprising C3-C6-alkyl, C5-C7-cycloalkyl, methylthioethyl, methylthio-tert-butyl, indolyl, phenyl, naphtyl, thienyl, propenyl, propinyl, hydroxyphenyl, indolyl and imidazolyl;

B is selected from the group comprising phenyl, substituted phenyl, naphtyl, thienyl, benzothienyl, hydroxyphenyl, indolyl, and imidazolyl; and D is selected from the group comprising phenyl, naphtyl, thienyl, thiazolyl, furanyl, hydroxyphenyl, indolyl and imidazolyl.

In a sixth aspect of the invention the problem is solved by a compound, preferably a C5a receptor antagonist, having the following structure:

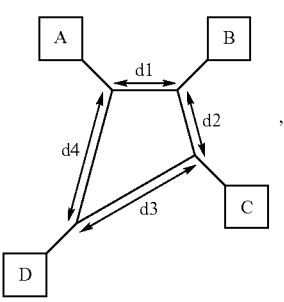

whereby

A, B, C and D represent the C-alpha atoms in amino acids, amino acid analogs or amino acid derivatives,

14 d1, d2, d3 and d4 represent the distances of A, B, C and D in at least one energetically accessible conformer of the compound and have the following values:

d1=3,9±0,5 Å d2=3,9±0,5 Å d3=9,0±1,5 Å d4=9,0±1,5 Å;

whereby the amino acids whose alpha-atoms are represented by A and C, individually and independently have a hydrophobic amino acid side chain that comprises an alkyl-, cycloalkyl, cycloalkylalkyl, heterocyclyl, aryl, arylalkyl, heteroaryl, heteroarylalkyl or methylthio-tert-butyl group, whereby the amino acids whose alpha-atoms are represented by B and D, individually and independently have an aromatic or heteroaromatic amino acid side chain that comprises an aryl, arylalkyl, heteroaryl or heteroarylalkyl group.

In an embodiment the amino acid whose alpha-atom is represented by A, is seletected from the group comprising C3-C6-alkyl, methylthioethyl, propenyl, propinyl, R5, methyl-R5 and ethyl-R5, whereby R5 is a radical that is selected from the group comprising C5-C7-cycloalkyl, phenyl, substituted phenyl, hydroxyphenyl, indolyl, imidazolyl, naphtyl and thienyl;

the amino acid whose alpha-atom is represented by B, is selected from the group comprising R5, methyl-R5 and ethyl-R5, whereby R5 is a radical that is selected from the group comprising phenyl, substituted phenyl, naphtyl, thienyl, benzothienyl, hydroxyphenyl, indolyl and imidazolyl;

the amino acid whose alpha-atom is represented by C, is selected from the group comprising C3-C6-alkyl, R5, methyl-R5 and ethyl-R5, whereby R5 is a radical that is selected from the group comprising C5-C7-cycloalkyl, phenyl, 1-methyl-phenyl, 2-methyl-phenyl, 3-methyl-phenyl and S-tBu; and the amino acid whose alpha-atom is represented by D, is selected from the group comprising R5, methyl-R5 and ethyl-R5, whereby R5 is a radical, that is selected from the group comprising phenyl, naphthyl, thienyl, thiazolyl, furanyl, hydroxyphenyl, indolyl and imidazolyl.

In a seventh aspect of the invention the problem is solved by a compound, preferably a C5a receptor antagonist, having the following structure:

X1-X2-X3-X4-X5-X6-X7-X8, (II)

whereby

X1 is a radical having a mass of about 1-300 and whereby X1 is preferably selected from the group comprising R5-, R5-CO—, R5-N(R6)-CO—, R5-O—CO—, R5-SO$_2$—, R5-N(R6)-SO$_2$—, R5-N(R6)-, R5-N(R6)-CS—, R5-N(R6)-C(NH)—, R5-CS—, R5-P(O)OH—, R5-B(OH)—, R5-CH=N—O—CH$_2$—CO—, whereby R5 and R6 are individually and independently selected from the group comprising H, F, hydroxy, alkyl, substituted alkyl, cycloalkyl, substituted cycloalkyl, heterocyclyl, substituted heterocyclyl, arylalkyl, substituted arylalkyl, aryl, substituted aryl, heteroaryl, substituted heteroaryl, acyl, substituted acyl, alkoxy, alkoxyalkyl, substituted alkoxyalkyl, aryloxyalkyl and substituted aryloxyalkyl, X2 is a radical that mimics the biological binding characteristics of a phenylalanine unit, X3 and X4 are individually and independently a spacer, whereby the spacer is preferably selected from the group comprising amino acids, amino acid analogs and amino acid derivates, X5 is a radical that mimics the biological binding characteristics of a cyclohexylalanine or homoleucine unit, X6 is a radical that mimics the biological binding characteristics of a tryptophane unit, X7 is a radical that mimics the biological binding characteristics of a norleucine or phenylalanine unit, X8 is a radical, whereby the radical is optionally present in structure II, and if it is present, it is selected from the group comprising H, $NH_2$, OH, NH—OH, NH—Oalkyl, amino, substituted amino, alkoxy, substituted alkoxy, hydrazino, substituted hydrazino, aminooxy, substituted aminooxy, alkyl, substituted alkyl, cycloalkyl, substituted cycloalkyl, heterocyclyl, substituted heterocyclyl, heteroaryl, substituted heteroaryl, arylalkyl, substituted arylalkyl, aryl, substituted aryl, amino acid, amino acid derivative and amino acid analogon;

the connecting lines—in formula (II) represent chemical bonds, whereby the chemical bond is individually and independently selected from the group comprising covalent bonds, ionic bonds and coordinative bonds, whereby preferably the bond is a chemical bond and more preferably the chemical bond is a bond selected from the group comprising amide bonds, disulfide bonds, ether bonds, thioether bonds, oxime bonds and aminotriazine bonds.

In an embodiment X1 is a radical having a mass of about 1-300, whereby the radical is preferably selected from the group comprising R5, R5-CO—, R5-N(R6)-CO—, R5-O-CO—, $R5\text{-}SO_2$—, R5-N(R6)-C(NH)—, whereby preferably R5 and R6 are individually and independently selected from the group comprising H, alkyl, substituted alkyl, cycloalkyl, substituted cycloalkyl, heterocyclyl, substituted heterocyclyl, aryl and substituted aryl;

X2 and X6 are individually and independently an aromatic amino acid, a derivative or an analogon thereof;

X5 and X7 are individually and independently a hydrophobic amino acid, a derivative or an analogon thereof.

In an embodiment X2, X5, X6 and X7 have individually and independently the following structure:

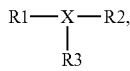
(III)

whereby

X is C(R4) or N,

R1 is optionally present and if R1 is present, it is a radical that is selected from the group comprising >N-R1B, >C(R1B)(R1D) and >O, whereby R1B and R1D are individually and independently selected from the group comprising H, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, cycloalkylalkyl and substituted cycloalkylalkyl;

R2 is optionally present and if R2 is present, it is a radical selected from the group comprising >C=O, >C=S, $>SO_2$, >S=O, >C=NH, >C=N—CN, >PO(OH), >B(OH), $>CH_2$, $>CH_2CO$, >CHF and $>CF_2$;

R4 is a radical, whereby the radical is selected from the group comprising H, F, $CH_3$, $CF_3$, alkyl and substituted alkyl;

and the binding of structure (III) to the moieties X1 and X3, X4 and X6, X5 and X7, and X6 and X8 preferably takes place via R1 and R2;

for X2 and for X6 individually and independently R3 is a radical, whereby the radical comprises an aromatic group and is selected from the group comprising aryl, substituted aryl, heteroaryl, substituted heteroaryl, arylalkyl, substituted arylalkyl, heteroarylalkyl, substituted heteroarylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl; and for X5 and for X7 individually and independently R3 is a radical, whereby the radical comprises an aliphatic or aromatic group and preferably is selected from the group comprising alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl.

In an embodiment a ring is formed using R3 and R4.

In an embodiment for X2 and for X6 individually and independently R3 is selected from the group comprising phenyl, substituted phenyl, benzyl, substituted benzyl, 1,1-diphenylmethyl, substituted 1,1-diphenylmethyl, naphthylmethyl, substituted naphthylmethyl, thienylmethyl, substituted thienylmethyl, benzothienylmethyl, substituted benzothienylmethyl, imidazolylmethyl, substituted imidazolylmethyl, indolylmethyl and substituted indolylmethyl.

In an embodiment for X5 and for X7 individually and independently R3 is selected from the group comprising C3-C5-alkyl, substituted C3-C5-alkyl, C5-C7-cycloalkyl, substituted C5-C7-cycloalkyl, C5-C7-cycloalkylmethyl, substituted C5-C7-cycloalkylmethyl, cycloalkylethyl, substituted cycloalkylethyl, benzyl, substituted benzyl, phenylethyl, naphthylmethyl, thienylmethyl, propenyl, propinyl, methylthioethyl, imidazolylmethyl, substituted imidazolylmethyl, indolylmethyl and substituted indolylmethyl.

In an embodiment of any of the preceding aspects and more particularly of the seventh aspect of the present invention X8 is selected from the group comprising H, OR1 and NR1R2, whereby R1 and R2 are individually and independently selected from the group comprising H, alkyl, aryl, cycloalkyl and arylalkyl.

In an embodiment of the seventh aspect X1 is selected from the group comprising H, acetyl, propanoyl, butanoyl, benzoyl, fluoromethylcarbonyl, difluoromethylcarbonyl, phenyl, oxycarbonyl, methyl-oxycarbonyl, phenyl-aminocarbonyl, methyl-aminocarbonyl, phenyl-sulfonyl, 2,6-dioxo-hexahydro-pyrimidine-4-carbonyl and methyl-sulfonyl.

In an embodiment of the seventh aspect X1 and/or X4 comprise one or more groups that improve water solubility, whereby the water solubility improving group is selected from the group comprising hydroxy, keto, carboxamido, ether, urea, carbamate, amino, substituted amino, guanidino, pyridyl and carboxyl.

In a eighth aspect of the invention the problem is solved by a compound, preferably a C5a receptor antagonist, having the following structure:

X1-X2-X3-X4-X5-X6-X7-X8, (II)

whereby X1-X3 and X5-X8 are defined in accordance with the seventh aspect of the present invention and whereby X4 is a cyclic or a non-cyclic amino acid, whereby the cyclic amino acid is selected from the group comprising proline, pipecolic acid, azetidine-2-carbonic acid, tetrahydroisoquinoline-3-carboxylic acid, tetrahydroisoquinoline-1-carboxylic acid, octahydroindole-2-carboxylic acid, 1-aza-bicyclo-[3.3.0]-octane-2-carboxylic acid, 4-phenyl-pyrrolidine-2-carboxylic acid, cis-Hyp and trans-Hyp, and the non-cyclic amino acid is selected from the group comprising Ser, Gln, Asn, Cys($O_2CH_2CH_2CONH_2$), Arg, Hyp ($COCH_2OCH_2CH_2OCH_2CH_2OCH_3$), Hyp(CONH—$CH_2CH(OH)$—$CH_2OH$) and respective derivatives thereof and respective analogs thereof; and the connecting lines—in formula (I) represent chemical bonds, whereby preferably the chemical bond is individually and independently selected from the group comprising covalent bonds, ionic bonds and coordinative bonds, whereby preferably the bond is a chemical bond and more preferably the chemical bond is a bond selected from the group comprising amide bonds, disulfide bonds, ether bonds, thioether bonds, oxime bonds and aminotriazine bonds.

In an embodiment of the eighth aspect of the present invention the amino acid represented by X4 preferably is chosen from the group comprising proline, Pipecolic acid, azetidine-2-carboxylic acid, tetrahydroisoquinoline-3-carboxylic acid, tetrahydroisoquinoline-1-carboxylic acid, octahydroindole-2-carboxylic acid, 1-aza-bicyclo-[3.3.0]-octane-2-carboxylic acid, 4-phenyl-pyrrolidine-2-carboxylic acid, Hyp, Ser, Gln, Asn, Cys($O_2CH_2CH_2CONH_2$) and Arg.

In a ninth aspect of the invention the problem is solved by a compound, preferably a C5a receptor antagonist, having the following structure:

X1-X2-X3-X4-X5-X6-X7-X8, (II)

whereby X1-X2 and X4-X8 are defined in accordance with the seventh and eighth aspect of the present invention and whereby X3 has the following structure:

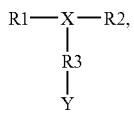

(IV)

whereby

X is C(R4) or N,

R1 is optionally present and if R1 is present it is a radical selected from the group comprising >N-R1B, >C(R1B)(R1D) and >O, whereby R1B and R1D are individually and independently selected from the group comprising H, alkyl, substituted alkyl, cycloalkyl, substituted cycloalkyl, heterocyclyl, substituted heterocyclyl, aryl, substituted aryl, heteroaryl, substituted heteroaryl, arylakyl, substituted arylalkyl, cycloalkylalkyl and substituted cycloalkylalkyl;

R2 is optionally present and if R2 is present it is a radical selected from the group comprising >C=O, >C=S, >$SO_2$, >PO(OH), >B(OH), >$CH_2$, >$CH_2CO$, >CHF and >$CF_2$;

R4 is a radical, whereby the radical is selected from the group comprising H, F, $CF_3$, alkyl and substituted alkyl;

the binding of structure (IV) to the moieties X2 and X4 preferably takes place via R1 and R2;

R3 is a radical selected from the group comprising H, alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted heterocyclylalkyl, aryl, substituted aryl, arylalkyl, substituted arylalkyl, heteroaryl, substituted heteroaryl, heteroarylalkyl, substituted heteroarylalkyl, acyl, substituted acyl, alkoxyalkyl, substituted alkoxyalkyl, aryloxyalkyl, substituted aryloxyalkyl, sulfhydrylalkyl, substituted sulfhydrylalkyl, hydroxyalkyl, substituted hydroxyalkyl, carboxyalkyl, substituted carboxyalkyl, carboxamidoalkyl, substituted carboxamidoalkyl, carboxyhydrazinoalkyl, ureidoalkyl aminoalkyl, substituted aminoalkyl, guanidinoalkyl and substituted guanidinoalkyl;

Y is optionally present and if present is a radical that is selected from the group comprising H, —N(YB1)-CO-YB2, —N(YB1)-CO—N(YB2)(YB3), —N(YB1)-C(N-YB2)-N(YB3)(YB4), —N(YB1)(YB2), —N(YB1)-$SO_2$-YB2, O-YB1, S-YB1, —CO-YB1, —CO—N(YB1)(YB2) and —C=N—O-YB1, whereby YB1, YB2, YB3 and YB4 are individually and independently selected from the group comprising H, CN, $NO_2$, alkyl, substituted alkyl, cycloalkyl, substituted cycloalkyl, heterocyclyl, substituted heterocyclyl, aryl, substituted aryl, heteroaryl, substituted heteroaryl, arylakyl, substituted arylalkyl, cycloalkylalkyl and substituted cycloalkylalkyl.

In an embodiment of the ninth aspect R3 is a radical having the structure

—$(CH_2)_m$—Y (VII)

or

—$(CH_2)_m$—$C_6H_4$—Y, (VIII) ist whereby m is 1, 2, 3 or 4;

Y is N(R3b)(R3c) or —N(YB1)-C(N-YB2)-N(YB3)(YB4), whereby R3b, R3c, YB1, YB2, YB3 and YB4 are individually and independently selected from the group comprising H, CN and alkyl.

In an embodiment of the ninth aspect a ring is formed between each two moieties of the compound, whereby the moieties of the compound are individually and independently selected from the group comprising YB1, YB2, YB3 and YB4.

In an embodiment of the ninth aspect the ring is formed using YB2 and YB3.

In an embodiment of the ninth aspect Y is —$NH_2$or

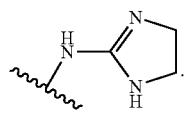

(IX)

In an embodiment of any of the seventh to the ninth aspect of the present invention X2 is a derivative of an amino acid selected from the group comprising phenylalanine, 2-fluoro-phenylalanine, 3-fluoro-phenylalanine, 4-fluoro-phenylalanine, 2-chloro-phenylalanine, 3-chloro-phenylalanine, 4-chloro-phenylalanine, 1-naphtylalanine, 2-thienylalanine, 3-thienylalanine, 3,3-diphenylalanine, tyrosine, tryptophane, histidine and respective derivatives thereof;
or X2 and X1 together are $PhCH_2CH_2CO-$ or $PhCH_2-$;
X6 is a derivative of an amino acid selected from the group comprising tryptophane, phenylalanine, tyrosine, histidine, 1-naphtylalanine, benzothienylalanine, 2-aminoindane-2-carboxylic acid, 2-thienylalanine, 3-thienylalanine, 2-fluoro-phenylalanine, 3-fluoro-phenylalanine, 4-fluoro-phenylalanine, 2-chloro-phenylalanine, 3-chloro-phenylalanine, 4-chloro-phenylalanine and respective derivatives thereof;
X5 is a derivative of an amino acid selected from the group comprising D-cyclohexylalanine, D-cyclohexylglycine, D-homo-cyclohexylalanine, D-homoleucine, D-cysteine (tBu), D-cysteine(iPr), octahydroindole-2-carboxylic acid, 2-methyl-D-phenylalanine and respective derivatives thereof; and
X7 is a derivative of an amino acid selected from the group comprising norvaline, norleucine, homo-leucine, leucine, isoleucine, valine, cysteine, cysteine(Me), cysteine(Et), cysteine(Pr), methionine, allylglycine, propargylglycine, cyclohexylglycine, cyclohexylalanine, phenylalanine, tyrosine, tryptophane, histidine, 1-naphtylalanine, 2-thienylalanine, 3-thienylalanine and respective derivatives thereof.

In an embodiment of any of the seventh to the ninth aspect of the present invention X3 is an amino acid derivative of an amino acid, whereby the amino acid is selected from the group comprising alpha-amino-glycine, alpha-beta-diamino-propionic acid (Dap), alpha-gamma-diaminobutanoic acid (Dab), ornithine, lysine, homolysine, Phe(4-$NH_2$), 2-amino-3-(4-piperidinyl)propionic acid and 2-amino-3-(3-piperidinyl)propionic acid, and the amino acid is derivatized at the side chain.

In a tenth aspect of the invention the problem is solved by a compound, preferably a C5a receptor antagonist, preferably of any of the seventh to the ninth aspect, having the following structure:

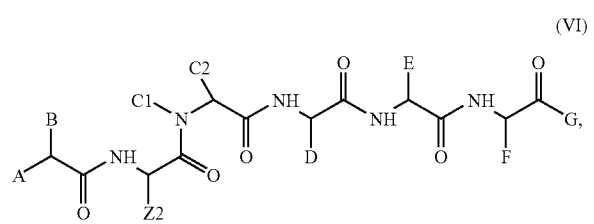

(VI)

whereby
A is selected from the group comprising H, $NH_2$, NHalkyl, $Nalkyl_2$, NHacyl, substituted NHacyl and OH,
B is selected from the group comprising $CH_2$(aryl), CH(aryl)$_2$, $CH_2$(heteroaryl) and substituted $CH_2$(aryl),
C1 and C2 are individually and independently selected from the group comprising alkyl and substituted alkyl, whereby optionally a bond can be formed between C1 and C2,
D is selected from the group comprising alkyl, cycloalkyl, $CH_2$(cycloalkyl), $CH_2CH_2$(cycloalkyl), $CH_2Ph$(2-Me) and $CH_2$—S-alkyl,
E is selected from the group comprising $CH_2$(aryl), substituted $CH_2$(aryl) and $CH_2$(heteroaryl),
F is selected from the group comprising alkyl, $CH_2$—S-alkyl, $CH_2CH_2$—S—Me, $CH_2CH=CH_2$, CH—CCH, cyclohexyl, $CH_2$cyclohexyl, $CH_2Ph$, $CH_2$naphtyl, $CH_2$thienyl, and
Z2 is -R3-Y—, whereby R3 is selected from the group comprising H, alkyl, arylalkyl, and Y is optionally present, and if Y is present, Y is selected from the group comprising H, N(YB1)(YB2), N(YB1)C(N-YB2)-N(YB3)(YB4),

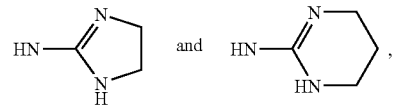

whereby YB1, YB2, YB3 and YB4 are individually and independently selected from the group comprising H, CN and alkyl, and optionally a ring is formed using at least two of YB1, YB2, YB3 and YB4, and
G is selected from the group comprising H, OR1 and NR1R2, whereby R1 and R2 are individually and independently selected from the group comprising H, alkyl, aryl, cycloalkyl and arylalkyl.

In an embodiment of the tenth aspect A is selected from the group comprising H, $NH_2$, NHEt, NHAc, OH,
B is selected from the group comprising $CH_2Ph$, $CH_2Ph$(4-F), CH(Ph)$_2$, $CH_2$thienyl and $CH_2$naphtyl,
C1 is selected from the group comprising H and methyl, C2 is selected from the group comprising methyl and $CH_2OH$, or if C1 and C2 are connected by a bond, the thus resulting structure is selected from the group comprising —$(CH_2)_2$—, —$(CH_2)_3$—, —$(CH_2)_4$— and —$CH_2CH(OH)CH_2$—.
D is selected from the group comprising $CH_2CH_2iPr$, $CH_2iPr$, cyclohexyl, $CH_2$cyclohexyl, $CH_2CH_2$cyclohexyl, $CH_2Ph$(2-Me), $CH_2$—S-tBu and $CH_2$—S-iPr,
E is selected from the group comprising g$CH_2Ph$, $CH_2Ph$(2-Cl), $CH_2Ph$(3-Cl), $CH_2Ph$(4-Cl), $CH_2Ph$(2-F), $CH_2Ph$(3-F), $CH_2Ph$(4-F), $CH_2$indolyl, $CH_2$thienyl, $CH_2$benzothienyl and $CH_2$naphtyl,
F is selected from the group comprising $(CH_2)_3CH_3$, $(CH_2)_2CH_3$, $(CH_2)_2$-ipr, $CH_2$-iPr, iPr, $CH_2$—S-Et, $CH_2CH_2$—S—Me, $CH_2CH=CH_2$, $CH_2$—CCH and cyclohexyl,
Z2 is -R3-Y—, whereby R3 is selected from the group comprising $CH_2$, $(CH_2)_2$, $(CH_2)_3$, $(CH_2)_4$ and $CH_2$—$C_6H_4$, and Y is selected from the group comprising $NH_2$, NHEt, N(Et)$_2$, NH—C(NH)—$NH_2$ and

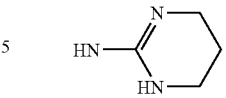

and
G is selected from the group comprising $NH_2$, NHMe, OH, and H.

The individual moieties of these embodiments of the compound according to the present invention as depicted in formula (VI), can be linked to the moieties of the compounds according to the present invention as of formula (II) as follows:

X1-X2 is

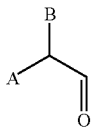

X3 is

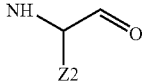

X4 is

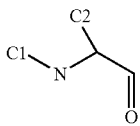

X5 is

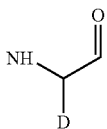

X6 is

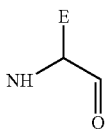

X7 is

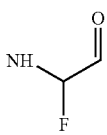

and X8 is G.

In an embodiment of any of the first to the tenth aspect of the present invention the compound is one of the following compounds:

| No. | Compound |
|---|---|
| 1 | Ac-Phe-[Orn-Pro-cha-Trp-Phe] [SEQ ID NO: 7] |
| 2 | Ac-Phe-[Orn-Hyp-cha-Trp-Phe] |
| 3 | $HOCH_2(CHOH)_4$—C=N—O—$CH_2$—CO-Phe-[Orn-Pro-cha-Trp-Nle] |
| 4 | X-Phe-[Orn-Pro-cha-Trp-Nle]; X = 2-acetamido-1-methyl-glucuronyl |
| 5 | Ac-Phe-[Orn-Hyp($COCH_2OCH_2CH_2OCH_2CH_2OCH_3$)-cha-Trp-Nle] |
| 6 | Ac-Phe-[Orn-Hyp(CONH—$CH_2$CH(OH)—$CH_2$OH)-cha-Trp-Nle] |
| 20 | Ac-Phe-[Orn-Pro-cha-Trp-Ecr] |
| 28 | Ac-Phe-[Orn-Pro-cha-Trp-Nle] |
| 29 | Ac-Phe-[Orn-Pro-cha-Trp-Met] [SEQ ID NO: 8] |
| 31 | Ac-Phe-[Orn-Pro-cha-Trp-Nva] |
| 32 | Ac-Phe-[Orn-Pro-cha-Trp-Hle] |
| 33 | Ac-Phe-[Orn-Pro-cha-Trp-Eaf] |
| 34 | Ac-Phe-[Orn-Pro-cha-Trp-Ebd] |
| 35 | Ac-Phe-[Orn-Pro-cha-Trp-Eag] |
| 36 | Ac-Phe-[Orn-Pro-cha-Trp-Pmf] |
| 37 | Ac-Phe-[Orn-Pro-cha-Trp-2Ni] |
| 38 | Ac-Phe-[Orn-Pro-cha-Trp-Thi] |
| 41 | Ph—$CH_2$—$CH_2$—CO-[Orn-Pro-cha-Trp-Nle] |
| 42 | H-Phe-[Orn-Pro-cha-Trp-Nle] |
| 43 | Ac-Lys-Phe-[Orn-Pro-cha-Trp-Nle] [SEQ ID NO: 9] |
| 44 | H-Phe-[Orn-Ser-cha-Trp-Nle] |
| 51 | Ac-Phe-Orn-Pro-cha-Trp-Phe-$NH_2$ [SEQ ID NO: 10] |
| 52 | Ac-Phe-Orn-Aze-cha-Bta-Phe-$NH_2$ |
| 53 | Ac-Phe-Orn-Pro-cha-Bta-2Ni—$NH_2$ |
| 54 | Ac-Phe-Orn-Pro-cha-Bta-Cha-$NH_2$ |
| 55 | Ac-Phe-Orn-Pip-cha-Trp-Phe-$NH_2$ |
| 56 | Ph—$CH_2$-[Orn-Pro-cha-Trp-Nle] |
| 57 | Ph—$CH_2$-[Orn-Pro-cha-Trp-Phe] |
| 58 | Ac-Phe-[Orn-Pro-cha-Trp-1Ni] |
| 59 | Ph—CH(OH)—$CH_2$—CO-[Orn-Pro-cha-Trp-Nle] |
| 61 | Ac-Phe-Orn-Pro-cha-Trp-Phe-$NH_2$ [SEQ ID NO: 11] |
| 62 | Ac-Phe-Orn-Pro-cha-Bta-Phe-$NH_2$ |
| 64 | Ac-Phe-Orn-Pro-cha-Trp-2Ni—$NH_2$ |
| 65 | Ac-Phe-Orn-Pro-cha-Trp-Cha-$NH_2$ |
| 66 | Ac-Thi-Orn-Aze-cha-Bta-Phe-$NH_2$ |
| 67 | Ac-Thi-Orn-Pip-cha-Bta-Phe-$NH_2$ |
| 68 | Ac-Phe-Orn-Pro-cha-Trp-Eap-$NH_2$ |
| 69 | $Me_2$-Phe-Orn-Pro-cha-Trp-Phe-$NH_2$ [SEQ ID NO: 12] |
| 70 | $Ph_2$—CH—$CH_2$—CO-Orn-Pro-cha-Trp-Phe-$NH_2$ |
| 71 | Ac-Ebw-Orn-Pro-cha-Trp-Phe-$NH_2$ |
| 72 | Ac-Phe-Orn-Pro-cha-Trp-NH—$CH_2$—$CH_2$—Ph |
| 73 | Ac-Phe-Orn-Aze-cha-Bta-NH—$CH_2$—$CH_2$—Ph |
| 74 | H-Phe-Orn-Pro-cha-Trp-Phe-$NH_2$ [SEQ ID NO: 13] |
| 75 | H—Me-Phe-Orn-Pro-cha-Trp-Phe-$NH_2$ [SEQ ID NO: 14] |
| 76 | Bu-NH—CO-Phe-Orn-Pro-cha-Trp-Phe-$NH_2$ [SEQ ID NO: 15] |
| 77 | Ac-Thi-Orn-Pro-cha-Trp-Phe-$NH_2$ |
| 78 | Ac-Ebw-Orn-Pro-cha-Trp-Phe-$NH_2$ |
| 79 | Ac-Phe-Orn-Ala-cha-Trp-Phe-$NH_2$ [SEQ ID NO: 16] |
| 80 | Ac-Phe-Orn-Pro-cha-Trp-Thi-$NH_2$ |
| 81 | Ac-Phe-Orn-Aze-cha-Pcf-Phe-$NH_2$ |
| 82 | Ac-Phe-Orn(Ac)-Pro-cha-Trp-Phe-$NH_2$ [SEQ ID NO: 17] |
| 83 | Ac-Phe-Orn-Aze-cha-Trp-Phe-$NH_2$ |
| 84 | Ac-Phe-Trp-Pro-cha-Trp-Phe-$NH_2$ [SEQ ID NO: 18] |
| 85 | Ph—NH—CO-Phe-Orn-Pro-cha-Trp-Phe-$NH_2$ [SEQ ID NO: 19] |
| 86 | Bu-O—CO-Phe-Orn-Pro-cha-Trp-Phe-$NH_2$ [SEQ ID NO: 20] |
| 87 | Ac-Phe-Lys-Pro-cha-Trp-Phe-$NH_2$ [SEQ ID NO: 21] |
| 88 | Ac-Phe-Arg-Pro-cha-Trp-Phe-$NH_2$ [SEQ ID NO: 22] |
| 89 | Ac-Phe-Gln-Pro-cha-Trp-Phe-$NH_2$ [SEQ ID NO: 23] |

| No. | Compound |
|---|---|
| 92 | Ac-Phe-Orn-Pip-cha-Trp-Phe-NH$_2$ |
| 93 | Ac-Phe-Orn-Hyp-cha-Trp-Phe-NH$_2$ |
| 94 | Ac-Phe-Orn-Pro-cha-Trp-1Ni—NH$_2$ |
| 95 | Ac-Phe-Orn-Aze-cha-Bta-Phe-NH—Me |
| 96 | CH$_3$—SO$_2$-Phe-Orn-Aze-cha-Bta-Phe-NH$_2$ |
| 99 | Ac-Phe-Orn-Aze-cha-Pff-Phe-NH$_2$ |
| 100 | Ac-Phe-Orn-Aze-cha-Mcf-Phe-NH$_2$ |
| 101 | Ac-Phe-Orn(Ac)-Aze-cha-Bta-Phe-NH$_2$ |
| 102 | Ac-Ebw-Orn-Pro-cha-Trp-Phe-NH$_2$ |
| 103 | Ac-Phe-Trp-Pro-cha-Trp-Phe-NH$_2$ [SEQ ID NO: 24] |
| 104 | Ac-Phe-Arg-Pro-cha-Trp-Phe-NH$_2$ [SEQ ID NO: 25] |
| 105 | Ac-Phe-Orn-Pip-cha-Trp-Phe-NH$_2$ |
| 106 | 3PP-Orn-Aze-cha-Bta-Phe-NH$_2$ |
| 107 | Ac-Phe-Orn-Tic-cha-Trp-Phe-NH$_2$ |
| 108 | Ac-Phe-Orn-Ser-cha-Trp-Phe-NH$_2$ [SEQ ID NO: 26] |
| 109 | Ac-Phe-Orn-Pro-chg-Trp-Phe-NH$_2$ [SEQ ID NO: 27] |
| 110 | Ac-Phe-Orn-Pro-hch-Trp-Phe-NH$_2$ [SEQ ID NO: 28] |
| 111 | Ac-Phe-Orn-Pro-cha-Trp-Phg-NH$_2$ |
| 112 | Ac-Phe-Bta-Aze-cha-Bta-Phe-NH$_2$ |
| 113 | Ac-Phe-Trp-Pro-cha-Bta-Phe-NH$_2$ [SEQ ID NO: 29] |
| 115 | Ac-Phe-Orn-Pip-cha-Trp-Phe-OH |
| 116 | Ac-Phe-Orn-Tic-cha-Trp-Phe-OH |
| 117 | Ac-Phe-Orn-Ser-cha-Trp-Phe-OH [SEQ ID NO: 30] |
| 118 | Ac-Phe-Orn-Pro-chg-Trp-Phe-OH [SEQ ID NO: 31] |
| 119 | Ac-Phe-Eec-Pro-cha-Bta-Phe-NH$_2$ |
| 120 | Ac-Phe-Nle-Pro-cha-Bta-Phe-NH$_2$ |
| 121 | Ac-Phe-Har-Pro-cha-Bta-Phe-NH$_2$ |
| 122 | Ac-Phe-Arg-Pro-cha-Bta-Phe-NH$_2$ [SEQ ID NO: 32] |
| 123 | Ac-Phe-Cys(Acm)-Pro-cha-Bta-Phe-NH$_2$ [SEQ ID NO: 33] |
| 124 | Ac-Phe-Mpa-Pro-cha-Bta-Phe-NH$_2$ |
| 125 | Ac-Eby-Orn-Pro-cha-Bta-Phe-NH$_2$ |
| 126 | Ac-Phg-Orn-Pro-cha-Bta-Phe-NH$_2$ |
| 127 | Ac-Phe-Paf-Pro-cha-Bta-Phe-NH$_2$ |
| 128 | H$_2$N—CO-Phe-Orn-Pro-cha-Bta-Phe-NH$_2$ |
| 129 | Me—O—CO-Phe-Orn-Pro-cha-Bta-Phe-NH$_2$ |
| 130 | (—CO—CH$_2$—NH—CO—)-Phe-Orn-Pro-cha-Bta-Phe-NH$_2$ |
| 132 | Ac-Phe-Orn-Pro-hch-Trp-Phe-OH [SEQ ID NO: 34] |
| 133 | (—CO—CH$_2$—CH$_2$—CO—)-Phe-Orn-Pro-cha-Bta-Phe-NH$_2$ |
| 134 | $^t$Bu-CO-Phe-Orn-Pro-cha-Bta-Phe-NH$_2$ |
| 135 | Ac-Lys-Phe-Orn-Aze-cha-Bta-Phe-NH$_2$ |
| 136 | Ac-Gly-Phe-Orn-Aze-cha-Bta-Phe-NH$_2$ |
| 137 | Ac-Arg-Phe-Orn-Aze-cha-Bta-Phe-NH$_2$ |
| 138 | Ac-His-Phe-Orn-Aze-cha-Bta-Phe-NH$_2$ |
| 139 | Ac-Ser-Phe-Orn-Aze-cha-Bta-Phe-NH$_2$ |
| 140 | Ac-Guf-Phe-Orn-Aze-cha-Bta-Phe-NH$_2$ |
| 141 | Ac-Dab-Phe-Orn-Aze-cha-Bta-Phe-NH$_2$ |
| 142 | FH$_2$C—CO-Phe-Orn-Pro-cha-Bta-Phe-NH$_2$ |
| 143 | Ac-Phe-Orn(Et$_2$)-Pro-cha-Trp-Phe-NH$_2$ [SEQ ID NO: 35] |
| 144 | Ac-Phe-[Orn-Hyp-cha-Trp-Nle] |
| 145 | 3PP-[Orn-Hyp-cha-Trp-Nle] |
| 146 | Ac-Phe-[Orn-Pro-cha-Trp-Tyr] [SEQ ID NO: 36] |
| 147 | Ac-Phe-[Orn-Pro-omf-Trp-Nle] |
| 149 | Ac-Phe-Orn-Pro-hle-Bta-Phe-NH$_2$ |
| 150 | Ac-Phe-Arg(CH$_2$—CH$_2$)-Pro-cha-Bta-Phe-NH$_2$ [SEQ ID NO: 37] |
| 151 | Ac-Ala-Phe-Orn-Aze-cha-Bta-Phe-NH2 |
| 152 | Ac-Arg-Phe-Orn-Aze-cha-Bta-Phe-NH2 |
| 153 | Ac-Cit-Phe-Orn-Aze-cha-Bta-Phe-NH2 |
| 154 | Ac-Gly-Phe-Orn-Aze-cha-Bta-Phe-NH2 |
| 155 | Ac-Gly-Phe-Orn-Aze-chg-Bta-Phe-NH2 |
| 156 | Ac-Gly-Phe-Orn-Aze-hch-Bta-Phe-NH2 |
| 157 | Ac-Gly-Thi-Orn-Aze-cha-Bta-Phe-NH2 |
| 158 | Ac-His-Phe-Orn-Aze-cha-Bta-Phe-NH2 |
| 159 | Ac-Hyp-Phe-Orn-Aze-cha-Bta-Phe-NH2 |
| 160 | Ac-Lys-Phe-Orn-Aze-cha-Bta-Phe-NH2 |
| 161 | Ac-Mff-Orn-Pro-cha-Bta-Phe-NH2 |
| 162 | Ac-Mff-Orn-Pro-hle-Bta-Phe-NH2 |
| 163 | Ac-Mff-Orn-Pro-hle-Mcf-Mff-NH2 |
| 164 | Ac-Mmy-Orn-Pro-hle-Pff-Phe-NH2 |
| 165 | Ac-NMF-Orn-Pro-cha-Bta-Phe-NH2 |
| 166 | Ac-Off-Orn-Pro-cha-Bta-Phe-NH2 |
| 167 | Ac-Off-Orn-Pro-hle-Bta-Phe-NH2 |
| 168 | Ac-Orn-Phe-Orn-Aze-cha-Bta-Phe-NH2 |
| 169 | Ac-Pff-Orn-Pro-cha-Bta-Phe-NH2 |
| 170 | Ac-Pff-Orn-Pro-hle-Bta-Phe-NH2 |
| 171 | Ac-Pff-Orn-Pro-hle-Mcf-Pff-NH2 |
| 172 | Ac-Phe-[Cys-Pro-cha-Bta-Phe-Cys]-NH2 [SEQ ID NO: 38] |
| 173 | Ac-Phe-[Orn-Asn-cha-Trp-Nle] |
| 174 | Ac-Phe-[Orn-Aze-cha-Trp-Nle] |
| 175 | Ac-Phe-[Orn-Chy-cha-Trp-Nle] |
| 176 | Ac-Phe-[Orn-HyA-cha-Trp-Phe] |
| 177 | Ac-Phe-[Orn-Hyp-hle-Bta-Phe] |
| 178 | Ac-Phe-[Orn-Hyp-hle-Mcf-Phe] |
| 179 | Ac-Phe-[Orn-Hyp-hle-Pff-Nle] |
| 180 | Ac-Phe-[Orn-Hyp-hle-Pff-Phe] |
| 181 | Ac-Phe-[Orn-Hyp-hle-Trp-Phe] |
| 182 | Ac-Phe-[Orn-Hyp-Mmf-Trp-Nle] |
| 183 | Ac-Phe-[Orn-Hyp-Mmf-Trp-Phe] |
| 184 | Ac-Phe-[Orn-NMD-cha-Trp-Nle] |
| 185 | Ac-Phe-[Orn-Pip-hle-Bta-Phe] |
| 186 | Ac-Phe-[Orn-Pro-cha-Pff-Nle] |
| 187 | Ac-Phe-[Orn-Pro-cha-Pff-Phe] |
| 188 | Ac-Phe-[Orn-Pro-cha-Trp-1Ni] |
| 189 | Ac-Phe-[Orn-Pro-cha-Trp-Cha] |
| 190 | Ac-Phe-[Orn-Pro-cha-Trp-Chg] |
| 192 | Ac-Phe-[Orn-Pro-cha-Trp-Ecr] |
| 193 | Ac-Phe-[Orn-Pro-cha-Trp-Leu] [SEQ ID NO: 39] |
| 194 | Ac-Phe-[Orn-Pro-cha-Trp-nle] |
| 195 | Ac-Phe-[Orn-Pro-cha-Trp-Phe] [SEQ ID NO: 40] |
| 196 | Ac-Phe-[Orn-Pro-hle-Bta-Nle] |
| 197 | Ac-Phe-[Orn-Pro-hle-Bta-Phe] |
| 198 | Ac-Phe-[Orn-Pro-hle-Pff-Phe] |
| 199 | Ac-Phe-[Orn-Pro-hle-Trp-Nle] |
| 200 | Ac-Phe-[Orn-Ser-cha-Trp-Nle] |
| 201 | Ac-Phe-[Orn-Ser-cha-Trp-Nle] |
| 202 | Ac-Phe-[Orn-Ser-hle-Trp-Nle] |
| 203 | Ac-Phe-[Orn-Thr-cha-Trp-Nle] |
| 204 | Ac-Phe-[Orn-Tic-cha-Trp-Nle] |
| 205 | Ac-Phe-[Orn-Tic-cha-Trp-Nle] |
| 206 | Ac-Phe-Ala-Pro-cha-Bta-Phe-NH2 [SEQ ID NO: 41] |
| 207 | Ac-Phe-Arg-Pro-hle-Bta-Phe-NH2 [SEQ ID NO: 42] |
| 208 | Ac-Phe-Arg-Pro-hle-Mcf-Phe-NH2 [SEQ ID NO: 43] |
| 209 | Ac-Phe-Cit-Hyp-hle-Bta-Phe-NH2 |
| 210 | Ac-Phe-Cit-Pro-cha-Bta-Phe-NH2 |
| 211 | Ac-Phe-Cit-Pro-hle-Bta-Phe-NH2 |
| 212 | Ac-Phe-Cit-Ser-hle-Bta-Phe-NH2 |
| 213 | Ac-Phe-Dab-Aze-cha-Bta-Phe-NH2 |
| 214 | Ac-Phe-Dab-Aze-hle-Bta-Phe-NH2 |
| 215 | Ac-Phe-Dab-Pro-cha-Bta-Phe-NH2 |
| 216 | Ac-Phe-Dap-Pro-cha-Bta-Phe-NH2 |
| 217 | Ac-Phe-Ech-Pro-cha-Bta-Phe-NH2 |
| 218 | Ac-Phe-Eep-Pro-cha-Bta-Phe-NH2 |
| 219 | Ac-Phe-Fcn-Aze-cha-Bta-Phe-NH2 |
| 220 | Ac-Phe-Fcn-Pro-cha-Bta-Phe-NH2 |
| 221 | Ac-Phe-Fco-Pro-cha-Bta-Phe-NH2 |
| 222 | Ac-Phe-Fco-Pro-cha-Bta-Phe-NH2 |
| 223 | Ac-Phe-Fcp-Aze-cha-Bta-Phe-NH2 |
| 224 | Ac-Phe-Ffa-Aze-cha-Bta-Phe-NH2 |
| 225 | Ac-Phe-Ffa-Pro-cha-Bta-Phe-NH2 |
| 226 | Ac-Phe-Ffa-Pro-hle-Bta-Phe-NH2 |
| 227 | Ac-Phe-G23-Pro-cha-Bta-Phe-NH2 |
| 228 | Ac-Phe-Guf-Pro-cha-Bta-Phe-NH2 |
| 229 | Ac-Phe-Har-Aze-cha-Bta-Phe-NH2 |
| 230 | Ac-Phe-His-Pro-cha-Bta-Phe-NH2 |

-continued

| No. | Compound |
|---|---|
| | [SEQ ID NO: 44] |
| 231 | Ac-Phe-L22-Pro-cha-Bta-Phe-NH2 |
| 232 | Ac-Phe-OrA-Pro-cha-Bta-Phe-NH2 |
| 233 | Ac-Phe-OrE-Pro-cha-Bta-Phe-NH2 |
| 234 | Ac-Phe-Orn-Aze-hle-Bta-Phe-NH2 |
| 235 | Ac-Phe-Orn-Chy-cha-Bta-Phe-NH2 |
| 236 | Ac-Phe-Orn-Chy-hle-Pff-Phe-NH2 |
| 237 | Ac-Phe-Orn-G24-cha-Bta-Phe-NH2 |
| 238 | Ac-Phe-Orn-G25-cha-Bta-Phe-NH2 |
| 239 | Ac-Phe-Orn-G26-cha-Bta-Phe-NH2 |
| 240 | Ac-Phe-Orn-G27-cha-Bta-Phe-NH2 |
| 241 | Ac-Phe-Orn-G30-cha-Bta-Phe-NH2 |
| 242 | Ac-Phe-Orn-G31-cha-Bta-Phe-NH2 |
| 243 | Ac-Phe-Orn-Hse-cha-Bta-Phe-NH2 |
| 244 | Ac-Phe-Orn-Hyp-hle-Bta-Phe-NH2 |
| 245 | Ac-Phe-Orn-Hyp-hle-Pff-Phe-NH2 |
| 246 | Ac-Phe-Orn-NMA-cha-Bta-Phe-NH2 |
| 247 | Ac-Phe-Orn-NMS-cha-Bta-Phe-NH2 |
| 248 | Ac-Phe-Orn-Pro-cha-1Ni-Phe-NH2 |
| 249 | Ac-Phe-Orn-Pro-cha-Bta-1Ni—NH2 |
| 250 | Ac-Phe-Orn-Pro-cha-Bta-Bhf-NH2 |
| 251 | Ac-Phe-Orn-Pro-cha-Bta-Dff-NH2 |
| 252 | Ac-Phe-Orn-Pro-cha-Bta-Eaa-NH2 |
| 253 | Ac-Phe-Orn-Pro-cha-Bta-L19 |
| 254 | Ac-Phe-Orn-Pro-cha-Bta-Mcf-NH2 |
| 255 | Ac-Phe-Orn-Pro-cha-Bta-Mff-NH2 |
| 256 | Ac-Phe-Orn-Pro-cha-Bta-NH—CH(CH2OH)—CH2—Ph |
| 257 | Ac-Phe-Orn-Pro-Cha-Bta-NH-NBn-CO—NH2 |
| 258 | Ac-Phe-Orn-Pro-cha-Bta-Opa-NH2 |
| 259 | Ac-Phe-Orn-Pro-cha-Bta-Pcf-NH2 |
| 260 | Ac-Phe-Orn-Pro-cha-Bta-Pmf-NH2 |
| 261 | Ac-Phe-Orn-Pro-cha-Bta-Thi-NH2 |
| 262 | Ac-Phe-Orn-Pro-cha-Otf-Phe-NH2 |
| 263 | Ac-Phe-Orn-Pro-ctb-Bta-Phe-NH2 |
| 264 | Ac-Phe-Orn-Pro-ctb-Eaa-Phe-NH2 |
| 265 | Ac-Phe-Orn-Pro-ctb-Mcf-Phe-NH2 |
| 266 | Ac-Phe-Orn-Pro-ctb-Pff-Phe-NH2 |
| 267 | Ac-Phe-Orn-Pro-hch-Trp-Phe-OH |
| | [SEQ ID NO: 45] |
| 268 | Ac-Phe-Orn-Pro-hle-1Ni-Phe-NH2 |
| 269 | Ac-Phe-Orn-Pro-hle-6FW-Phe-NH2 |
| 270 | Ac-Phe-Orn-Pro-hle-Bta-1Ni—NH2 |
| 271 | Ac-Phe-Orn-Pro-hle-Bta-2Ni—NH2 |
| 272 | Ac-Phe-Orn-Pro-hle-Bta-5Ff-NH2 |
| 273 | Ac-Phe-Orn-Pro-hle-Bta-Aic-NH2 |
| 274 | Ac-Phe-Orn-Pro-hle-Bta-Cha-NH2 |
| 275 | Ac-Phe-Orn-Pro-hle-Bta-Chg-NH2 |
| 276 | Ac-Phe-Orn-Pro-hle-Bta-Eaa-NH2 |
| 277 | Ac-Phe-Orn-Pro-hle-Bta-Egy-NH2 |
| 278 | Ac-Phe-Orn-Pro-hle-Bta-Pcf-NH2 |
| 279 | Ac-Phe-Orn-Pro-hle-Bta-Pff-NH2 |
| 280 | Ac-Phe-Orn-Pro-hle-Bta-Phe-NH2 |
| 281 | Ac-Phe-Orn-Pro-hle-Bta-phe-OH |
| 282 | Ac-Phe-Orn-Pro-hle-Bta-Tyr-NH2 |
| 283 | Ac-Phe-Orn-Pro-hle-Dff-Phe-NH2 |
| 284 | Ac-Phe-Orn-Pro-hle-Eaa-Phe-NH2 |
| 285 | Ac-Phe-Orn-Pro-hle-Egc-Phe-NH2 |
| 286 | Ac-Phe-Orn-Pro-hle-Egy-Phe-NH2 |
| 287 | Ac-Phe-Orn-Pro-hle-Egz-Phe-NH2 |
| 288 | Ac-Phe-Orn-Pro-hle-Mcf-2Ni—NH2 |
| 289 | Ac-Phe-Orn-Pro-hle-Mcf-Cha-NH2 |
| 290 | Ac-Phe-Orn-Pro-hle-Mcf-Pff-NH2 |
| 291 | Ac-Phe-Orn-Pro-hle-Mcf-Phe-NH2 |
| 292 | Ac-Phe-Orn-Pro-hle-Mff-Phe-NH2 |
| 293 | Ac-Phe-Orn-Pro-hle-Mmy-Phe-NH2 |
| 294 | Ac-Phe-Orn-Pro-hle-Ocf-Phe-NH2 |
| 295 | Ac-Phe-Orn-Pro-hle-Off-Phe-NH2 |
| 296 | Ac-Phe-Orn-Pro-hle-Otf-Phe-NH2 |
| 297 | Ac-Phe-Orn-Pro-hle-Pff-2Ni—NH2 |
| 298 | Ac-Phe-Orn-Pro-hle-Pff-Cha-NH2 |
| 299 | Ac-Phe-Orn-Pro-hle-Pff-Eaa-NH2 |
| 300 | Ac-Phe-Orn-Pro-hle-Pff-Mmy-NH2 |
| 301 | Ac-Phe-Orn-Pro-hle-Pff-Pff-NH2 |
| 302 | Ac-Phe-Orn-Pro-hle-Pff-Phe-NH2 |
| 304 | Ac-Phe-Orn-Pro-hle-Phe-Phe-NH2 |

-continued

| No. | Compound |
|---|---|
| | [SEQ ID NO: 46] |
| 305 | Ac-Phe-Orn-Pro-hle-Tff-Phe-NH2 |
| 306 | Ac-Phe-Orn-Pro-hle-Trp-Phe-NH2 |
| | [SEQ ID NO: 47] |
| 307 | Ac-Phe-Orn-Pro-ile-Trp-Phe-NH2 |
| | [SEQ ID NO: 48] |
| 308 | Ac-Phe-Orn-Pro-omf-Bta-Phe-NH2 |
| 309 | Ac-Phe-Orn-Ser-cha-Bta-Phe-NH2 |
| 310 | Ac-Ser-Phe-Orn-Aze-cha-Bta-Phe-NH2 |
| 311 | Ac-Thi-[Orn-Pro-hle-Bta-Phe] |
| 312 | Ac-Thi-Orn-Pro-cha-Bta-Phe-NH2 |
| 313 | Ac-Thi-Orn-Pro-cha-Bta-Thi-NH2 |
| 314 | Ac-Thr-Phe-Orn-Aze-cha-Bta-Phe-NH2 |
| 315 | Bzl-[Orn-Pro-cha-Bta-Nle] |
| 316 | CH3CH2CO-Phe-Orn-Pro-cha-Bta-Phe-NH2 |
| 317 | Def-[Orn-Ser-hle-Trp-Nle] |
| 318 | Eby-Phe-[Orn-Hyp-cha-Trp-Phe] |
| 319 | Eth-Phe-[Orn-Pro-hle-Pff-Nle] |
| 320 | FAc-Phe-Fib-Aze-cha-Bta-Phe-NH2 |
| 321 | FAc-Phe-Orn-Aze-cha-Bta-Phe-NH2 |
| 322 | FAc-Phe-Orn-Pro-cha-Bta-Phe-NH2 |
| 323 | Fai-Phe-[Orn-Hyp-cha-Trp-Phe] |
| 324 | Faz-Orn-Pro-cha-Bta-Phe-NH2 |
| 325 | Fbi-Phe-[Orn-Pro-cha-Trp-Nle] |
| 326 | Fbn-Phe-[Orn-Hyp-cha-Trp-Phe] |
| 327 | Fbn-Phe-[Orn-Pro-cha-Trp-Nle] |
| 328 | Fbn-Phe-[Orn-Pro-cha-Trp-Nle] |
| 329 | Fbn-Phe-Cit-Pro-hle-Bta-Phe-NH2 |
| 330 | Fbo-Phe-[Orn-Pro-cha-Trp-Nle] |
| 331 | Fbp-[Orn-Pro-cha-Trp-Nle] |
| 332 | Fci-[Phe-Orn-Hyp-cha-Trp-Phe] |
| 333 | Fck-[Phe-Orn-Pro-cha-Trp-Nle] |
| 334 | Fck-Phe-[Orn-Pro-cha-Trp-Nle] |
| 335 | Fha-Phe-[Orn-Hyp-cha-Trp-Phe] |
| 336 | Fhb-[Phe-Orn-Hyp-cha-Trp-Phe] |
| 337 | Fhi-Phe-[Orn-Hyp-cha-Trp-Phe] |
| 338 | Fhu-Phe-[Orn-Pro-hle-Pff-Nle] |
| 339 | Fhu-Phe-Orn-Pro-cha-Bta-Phe-NH2 |
| 340 | Fid-Phe-Orn-Pro-cha-Bta-Phe-NH2 |
| 341 | H-Amf-[Orn-Aze-hle-Pff-Nle] |
| 342 | H-Bal-Phe-[Orn-Hyp-hle-Trp-Nle] |
| 343 | H-Bal-Phe-[Orn-Pro-hle-Pff-Nle] |
| 344 | H-Eby-[Orn-Hyp-hle-Trp-Nle] |
| 345 | H-Gly-Phe-Orn-Pro-cha-Bta-Phe-NH2 |
| | [SEQ ID NO: 49] |
| 346 | H-Nip-Phe-Cit-Pro-hle-Bta-Phe-NH2 |
| 347 | Hoo-Phe-[Orn-Hyp-hle-Pff-Nle] |
| 348 | Hoo-Phe-Cit-Pro-hle-Pff-Phe-NH2 |
| 349 | Hoo-Phe-Orn-Hyp-hle-Pff-Phe-NH2 |
| 350 | Hoo-Phe-Orn-Pro-hle-Bta-Phe-NH2 |
| 351 | Hoo-Phe-Orn-Pro-hle-Mcf-Phe-NH2 |
| 352 | Hoo-Phe-Orn-Pro-hle-Pff-Phe-NH2 |
| 353 | H-Phe-[Lys-Hyp-hle-Pff-Nle] |
| 354 | H-Phe-[Orn-Hym-hle-Mcf-Nle] |
| 355 | H-Phe-[Orn-Hym-hle-Pff-Phe] |
| 356 | H-Phe-[Orn-Hyp-cha-Trp-Nle] |
| 357 | H-Phe-[Orn-Hyp-cha-Trp-Phe] |
| 358 | H-Phe-[Orn-Hyp-ctb-Pff-Nle] |
| 359 | H-Phe-[Orn-Hyp-ctb-Trp-Nle] |
| 360 | H-Phe-[Orn-Hyp-ctb-Trp-Phe] |
| 361 | H-Phe-[Orn-Hyp-hle-Mcf-Leu] |
| 362 | H-Phe-[Orn-Hyp-hle-Pff-Chg] |
| 363 | H-Phe-[Orn-Hyp-hle-Pff-Hle] |
| 364 | H-Phe-[Orn-Hyp-hle-Pff-Leu] |
| 365 | H-Phe-[Orn-Hyp-hle-Pff-Nle] |
| 366 | H-Phe-[Orn-Hyp-hle-Pff-Phe] |
| 367 | H-Phe-[Orn-Hyp-hle-Trp-Hle] |
| 368 | H-Phe-[Orn-Hyp-hle-Trp-Leu] |
| 369 | H-Phe-[Orn-Hyp-hle-Trp-Nle] |
| 370 | H-Phe-[Orn-Hyp-hle-Trp-Nva] |
| 371 | H-Phe-[Orn-Hyp-hle-Trp-Phe] |
| 372 | H-Phe-[Orn-NMS-cha-Trp-Nle] |
| 373 | H-Phe-[Orn-NMS-hle-Pff-Phe] |
| 374 | H-Phe-[Orn-Pro-cha-Pff-Nle] |
| 375 | H-Phe-[Orn-Pro-cha-Pff-Phe] |
| 376 | H-Phe-[Orn-Pro-cha-Trp-Nle] |
| 377 | H-Phe-[Orn-Pro-hle-Mcf-Phe] |

-continued

| No. | Compound |
|---|---|
| 378 | H-Phe-[Orn-Pro-hle-Ocf-Phe] |
| 379 | H-Phe-[Orn-Pro-hle-Pff-Nle] |
| 380 | H-Phe-[Orn-Pro-hle-Pff-Phe] |
| 381 | H-Phe-[Orn-Pro-hle-Trp-Nle] |
| 382 | H-Phe-[Orn-Ser-cha-Trp-Nle] |
| 383 | H-Phe-[Orn-Ser-cha-Trp-Phe] [SEQ ID NO: 50] |
| 384 | H-Phe-[Orn-Ser-hle-Eaa-Nle] |
| 385 | H-Phe-[Orn-Ser-hle-Mcf-Leu] |
| 386 | H-Phe-[Orn-Ser-hle-Ocf-Nle] |
| 387 | H-Phe-[Orn-Ser-hle-Pff-Leu] |
| 388 | H-Phe-[Orn-Ser-hle-Pff-Nle] |
| 389 | H-Phe-[Orn-Ser-hle-Pff-Phe] |
| 390 | H-Phe-[Orn-Ser-hle-Trp-Nle] |
| 391 | H-Phe-Cit-Pro-hle-Bta-Phe-NH2 |
| 392 | Ohf-[Orn-Hyp-hle-Trp-Nle] |
| 393 | Tmg-Phe-[Orn-Hyp-cha-Trp-Phe] |

In an eleventh aspect of the invention the problem is solved by a pharmaceutical composition comprising at least one compound according to any of the preceding claims and additionally a pharmaceutically acceptable carrier.

In a twelvth aspect of the invention the problem is solved by the use of at least one of the compounds of any of the first to the tenth aspect of the present invention for the manufacture of a medicament.

In an embodiment of the twelvth aspect the medicament is used for the prevention and/or treatment of a condition associated with complement activation and/or where the inhibition of the complement system leads to a relief of the symptoms.

In an embodiment of the twelvth aspect the medicament is used for the prevention and/or treatment of a condition where the inhibition of the C5a receptor alone or in combination with other therapeutics leads to a relief of the symptoms.

In an embodiment of the twelvth aspect the condition and/or the symptoms to be treated are selected from the group comprising autoimmune diseases, acute inflammatory diseases, trauma, local inflammations, shock and burn.

In an embodiment of the twelvth aspect the condition is selected from the group comprising rheumatoid arthritis, ankylosis spodylitis, sarcoidosis, systemic lupus erythematosus, multiple sclerosis, psoriasis, septic shock, haemorrhagic shock, systemic inflammatory response syndrome (SIRS), multiple organ failure (MOF), asthma, vasculitis, myocarditis, dermatomyositis, inflammatory bowel disease (IBD), pemphigus, myasthenia gravis, glomerulonephritis, acute respiratory insufficiency, stroke, myocardial infarction, reperfusion injury, neurocognitive dysfunction, anti-phospholipid syndrome, burn, inflammatory diseases of the eye, local manifestations of systemic diseases, inflammatory diseases of the vasculature, and acute injuries of the central nervous system.

In an embodiment of the twelvth aspect the inflammatory disease of the eye is selected from the group comprising uveitis, age-related macular degeneration, diabetic retinopathy, diabetic macular edema, ocular pemphigoid, keratoconjunctivitis, Stevens-Johnson syndrome, and Graves ophthalmopathy.

In an embodiment of the twelvth aspect the condition is a local manifestation of a systemic disease, whereby the systemic disease is selected from the group comprising rheumatoid arthritis, SLE, type I diabetes, and type II diabetes.

In an embodiment of the twelvth aspect the manifestations are selected from the group comprising manifestations at the eye, at or in the brain, at the vessels, at the heart, at the lung, at the kidneys, at the liver, at the gastro-intestinal tract, at the spleen, at the skin, at the skeletal system, at the lymphatic system, and in the blood.

In an embodiment of the twelvth aspect the inflammatory disease of vasulature is selected from the group comprising vasculitis, vascular leakage, and atherosclerosis.

In a thirteenth aspect of the invention the problem is solved by the use of at least one compound according to any of the first to the tenth aspect of the present invention for the prevention and/or support of surgery, especially for the manufacture of a medicament for such purpose.

In an embodiment of the twelvth and thirteenth aspect of the present invention the medicament is used for the prevention and/or the support of surgery.

In an embodiment of the twelvth and thirteenth aspect of the present invention the medicament is used for the prevention and/or support and/or post-operative treatment of a surgery, whereby the surgery is selected from the group comprising CABG, PACT, PTA, MidCAB, OPCAB, thrombolysis, organ transplantation, and vessel clamping.

In an embodiment of the twelvth and thirteenth aspect of the present invention the medicament is used for thrombolytic treatment.

In an embodiment of the twelvth and thirteenth aspect of the present invention the medicament is used in the settings of dialysis therapy, optionally before, during, and/or after such treatment.

In an embodiment of the twelvth and thirteenth aspect of the present invention the medicament is used for the prevention of organ damage of a transplanted organ or of an organ to be transplanted.

In an embodiment of the twelvth and thirteenth aspect of the present invention the medicament is used for the prevention or treatment of transplant rejection.

In a still further aspect the present invention is related to a method for the treatment of patients, whereby the method comprises the administration of one or several of the compounds according to the present invention. The treatment may be a treatment in the narrower sense, however, also includes a preventive treatment and a secondary treatment. In an embodiment of the method the treatment is a treatment of CPB (cardiopulmonary bypass) patients which are to be protected against a neurocognitive dysfunction by a preventive administration of the inhibitors according to the present invention.

The patient to be treated is preferably a mammal, more preferably a domestic farming animal, sports animal and pet, and most preferably a human being. In a preferred embodiment the patient is a patient in of such treatment. In a further preferred embodiment the patient is suffering from one of the above mentioned diseases for the treatment of which the compounds according to the present invention may be used.

The invention thus provides for the first time such antagonists for the C5a receptor, that overcome the inherent pharmacological disadvantages of the antagonistic peptides of the prior art which contain a positive charge.

The invention is based on the surprising finding, that in contrast to the technical teaching of the prior art, also antagonists for the C5a receptor can be obtained which, under physiological conditions, especially at a pH of 7.4, do not have a positive net charge and/or whose C-terminal amino acid does not possess a positive charge under physiological conditions.

According to the understanding of the inventors the positive charge in peptides can be very disadvantageous from a pharmacological point of view. Positive charges can, e. g., lead to histamine release and cause lower membrane permeability (see example 15). Therefore it is particularly desired to develop a peptidic antagonist that does not possess a positive net charge (in the following also referred to as compound).

Additionally, the avoidance of a C-terminal positive charge can have further positive effects: For example, receptor specificity or important in vivo parameters like pharmacokinetics, plasma protein binding or mutagenicity can be positively influenced.

The compounds which are disclosed in the present invention were tested in a primary assay for thieir $IC_{50}$ values in a functional assay system. Preferably all compounds, peptides and peptidomimetics are regarded to have noteworthy inhibitory activity in the sense of the present invention, that have an $IC_{50}$ value of less than 200 nM in a functional assay system as described in example 1.

In particular the compounds of the invention are C5a receptor antagonists. Even more preferably they are peptides or peptidomimetics. Furthermore the invention is based on the surprising finding, that the compounds which are used in accordance with the present invention as C5a receptor antagonists posses an uncharged C-terminal amino acid, amino acid derivative or amino acid analog.

Particularly preferred compounds and antagonists according to the present invention are the following cyclic compounds.

| Nr. | Compound |
|---|---|
| 1 | Ac-Phe-[Orn-Pro-cha-Trp-Phe] [SEQ ID NO: 7] |
| 2 | Ac-Phe-[Orn-Hyp-cha-Trp-Phe] |
| 3 | HOCH2(CHOH)4—C=N—O—CH2—CO-Phe-[Orn-Pro-cha-Trp-Nle] |
| 4 | X-Phe-[Orn-Pro-cha-Trp-Nle]; X = 2-Acetamido-1-Methyl-Glucuronyl |
| 5 | Ac-Phe-[Orn-Hyp(COCH2OCH2CH2OCH2CH2OCH3)-cha-Trp-Nle] |
| 6 | Ac-Phe-[Orn-Hyp(CONH—CH2CH(OH)—CH2OH)-cha-Trp-Nle] |
| 20 | Ac-Phe-[Orn-Pro-cha-Trp-Ecr] |
| 28 | Ac-Phe-[Orn-Pro-cha-Trp-Nle] |
| 29 | Ac-Phe-[Orn-Pro-cha-Trp-Met] [SEQ ID NO: 8] |
| 31 | Ac-Phe-[Orn-Pro-cha-Trp-Nva] |
| 32 | Ac-Phe-[Orn-Pro-cha-Trp-Hle] |
| 33 | Ac-Phe-[Orn-Pro-cha-Trp-Eaf] |
| 34 | Ac-Phe-[Orn-Pro-cha-Trp-Ebd] |
| 35 | Ac-Phe-[Orn-Pro-cha-Trp-Eag] |
| 36 | Ac-Phe-[Orn-Pro-cha-Trp-Pmf] |
| 37 | Ac-Phe-[Orn-Pro-cha-Trp-2Ni] |
| 38 | Ac-Phe-[Orn-Pro-cha-Trp-Thi] |
| 41 | Ph—CH2—CH2—CO-[Orn-Pro-cha-Trp-Nle] |
| 42 | H-Phe-[Orn-Pro-cha-Trp-Nle] |
| 43 | Ac-Lys-Phe-[Orn-Pro-cha-Trp-Nle] [SEQ ID NO: 9] |
| 44 | H-Phe-[Orn-Ser-cha-Trp-Nle] |
| 56 | Ph—CH2-[Orn-Pro-cha-Trp-Nle] |
| 57 | Ph—CH2-[Orn-Pro-cha-Trp-Phe] |
| 58 | Ac-Phe-[Orn-Pro-cha-Trp-1Ni] |
| 59 | Ph—CH(OH)—CH2—CO-[Orn-Pro-cha-Trp-Nle] |
| 144 | Ac-Phe-[Orn-Hyp-cha-Trp-Nle] |
| 145 | 3PP-[Orn-Hyp-cha-Trp-Nle] |
| 146 | Ac-Phe-[Orn-Pro-cha-Trp-Tyr] [SEQ ID NO: 36] |
| 147 | Ac-Phe-[Orn-Pro-omf-Trp-Nle] |
| 172 | Ac-Phe-[Cys-Pro-cha-Bta-Phe-Cys]-NH2 [SEQ ID NO: 38] |
| 173 | Ac-Phe-[Orn-Asn-cha-Trp-Nle] |
| 174 | Ac-Phe-[Orn-Aze-cha-Trp-Nle] |
| 175 | Ac-Phe-[Orn-Chy-cha-Trp-Nle] |
| 176 | Ac-Phe-[Orn-HyA-cha-Trp-Phe] |
| 177 | Ac-Phe-[Orn-Hyp-hle-Bta-Phe] |
| 178 | Ac-Phe-[Orn-Hyp-hle-Mcf-Phe] |

-continued

| Nr. | Compound |
|---|---|
| 179 | Ac-Phe-[Orn-Hyp-hle-Pff-Nle] |
| 180 | Ac-Phe-[Orn-Hyp-hle-Pff-Phe] |
| 181 | Ac-Phe-[Orn-Hyp-hle-Trp-Phe] |
| 182 | Ac-Phe-[Orn-Hyp-Mmf-Trp-Nle] |
| 183 | Ac-Phe-[Orn-Hyp-Mmf-Trp-Phe] |
| 184 | Ac-Phe-[Orn-NMD-cha-Trp-Nle] |
| 185 | Ac-Phe-[Orn-Pip-hle-Bta-Phe] |
| 186 | Ac-Phe-[Orn-Pro-cha-Pff-Nle] |
| 187 | Ac-Phe-[Orn-Pro-cha-Pff-Phe] |
| 188 | Ac-Phe-[Orn-Pro-cha-Trp-1Ni] |
| 189 | Ac-Phe-[Orn-Pro-cha-Trp-Cha] |
| 190 | Ac-Phe-[Orn-Pro-cha-Trp-Chg] |
| 192 | Ac-Phe-[Orn-Pro-cha-Trp-Ecr] |
| 193 | Ac-Phe-[Orn-Pro-cha-Trp-Leu] [SEQ ID NO: 39] |
| 194 | Ac-Phe-[Orn-Pro-cha-Trp-nle] |
| 195 | Ac-Phe-[Orn-Pro-cha-Trp-Phe] [SEQ ID NO: 40] |
| 196 | Ac-Phe-[Orn-Pro-hle-Bta-Nle] |
| 197 | Ac-Phe-[Orn-Pro-hle-Bta-Phe] |
| 198 | Ac-Phe-[Orn-Pro-hle-Pff-Phe] |
| 199 | Ac-Phe-[Orn-Pro-hle-Trp-Nle] |
| 200 | Ac-Phe-[Orn-Ser-cha-Trp-Nle] |
| 201 | Ac-Phe-[Orn-Ser-cha-Trp-Nle] |
| 202 | Ac-Phe-[Orn-Ser-hle-Trp-Nle] |
| 203 | Ac-Phe-[Orn-Thr-cha-Trp-Nle] |
| 204 | Ac-Phe-[Orn-Tic-cha-Trp-Nle] |
| 205 | Ac-Phe-[Orn-Tic-cha-Trp-Nle] |
| 311 | Ac-Thi-[Orn-Pro-hle-Bta-Phe] |
| 315 | Bzl-[Orn-Pro-cha-Bta-Nle] |
| 317 | Def-[Orn-Ser-hle-Trp-Nle] |
| 318 | Eby-Phe-[Orn-Hyp-cha-Trp-Phe] |
| 319 | Eth-Phe-[Orn-Pro-hle-Pff-Nle] |
| 323 | Fai-Phe-[Orn-Hyp-cha-Trp-Phe] |
| 325 | Fbi-Phe-[Orn-Pro-cha-Trp-Nle] |
| 326 | Fbn-Phe-[Orn-Hyp-cha-Trp-Phe] |
| 327 | Fbn-Phe-[Orn-Pro-cha-Trp-Nle] |
| 328 | Fbn-Phe-[Orn-Pro-cha-Trp-Nle] |
| 330 | Fbo-Phe-[Orn-Pro-cha-Trp-Nle] |
| 331 | Fbp-[Orn-Pro-cha-Trp-Nle] |
| 332 | Fci-Phe-Orn-Hyp-cha-Trp-Phe] |
| 333 | Fck-Phe-[Orn-Pro-cha-Trp-Nle] |
| 334 | Fck-Phe-[Orn-Pro-cha-Trp-Nle] |
| 335 | Fha-Phe-[Orn-Hyp-cha-Trp-Phe] |
| 336 | Fhb-[Phe-Orn-Hyp-cha-Trp-Phe] |
| 337 | Fhi-Phe-[Orn-Hyp-cha-Trp-Phe] |
| 338 | Fhu-Phe-[Orn-Pro-hle-Pff-Nle] |
| 341 | H-Amf-[Orn-Aze-hle-Pff-Nle] |
| 342 | H-Bal-Phe-[Orn-Hyp-hle-Trp-Nle] |
| 343 | H-Bal-Phe-[Orn-Pro-hle-Pff-Nle] |
| 344 | H-Eby-[Orn-Hyp-hle-Trp-Nle] |
| 347 | Hoo-Phe-[Orn-Hyp-hle-Pff-Nle] |
| 353 | H-Phe-[Lys-Hyp-hle-Pff-Nle] |
| 354 | H-Phe-[Orn-Hym-hle-Mcf-Nle] |
| 355 | H-Phe-[Orn-Hym-hle-Pff-Phe] |
| 356 | H-Phe-[Orn-Hyp-cha-Trp-Nle] |
| 357 | H-Phe-[Orn-Hyp-cha-Trp-Phe] |
| 358 | H-Phe-[Orn-Hyp-ctb-Pff-Nle] |
| 359 | H-Phe-[Orn-Hyp-ctb-Trp-Nle] |
| 360 | H-Phe-[Orn-Hyp-ctb-Trp-Phe] |
| 361 | H-Phe-[Orn-Hyp-hle-Mcf-Leu] |
| 362 | H-Phe-[Orn-Hyp-hle-Pff-Chg] |
| 363 | H-Phe-[Orn-Hyp-hle-Pff-Hle] |
| 364 | H-Phe-[Orn-Hyp-hle-Pff-Leu] |
| 365 | H-Phe-[Orn-Hyp-hle-Pff-Nle] |
| 366 | H-Phe-[Orn-Hyp-hle-Pff-Phe] |
| 367 | H-Phe-[Orn-Hyp-hle-Trp-Hle] |
| 368 | H-Phe-[Orn-Hyp-hle-Trp-Leu] |
| 369 | H-Phe-[Orn-Hyp-hle-Trp-Nle] |
| 370 | H-Phe-[Orn-Hyp-hle-Trp-Nva] |
| 371 | H-Phe-[Orn-Hyp-hle-Trp-Phe] |
| 372 | H-Phe-[Orn-NMS-cha-Trp-Nle] |
| 373 | H-Phe-[Orn-NMS-hle-Pff-Phe] |
| 374 | H-Phe-[Orn-Pro-cha-Pff-Nle] |
| 375 | H-Phe-[Orn-Pro-cha-Pff-Phe] |
| 376 | H-Phe-[Orn-Pro-cha-Trp-Nle] |
| 377 | H-Phe-[Orn-Pro-hle-Mcf-Phe] |

| Nr. | Compound |
|---|---|
| 378 | H-Phe-[Orn-Pro-hle-Ocf-Phe] |
| 379 | H-Phe-[Orn-Pro-hle-Pff-Nle] |
| 380 | H-Phe-[Orn-Pro-hle-Pff-Phe] |
| 381 | H-Phe-[Orn-Pro-hle-Trp-Nle] |
| 382 | H-Phe-[Orn-Ser-cha-Trp-Nle] |
| 383 | H-Phe-[Orn-Ser-cha-Trp-Phe] [SEQ ID NO: 50] |
| 384 | H-Phe-[Orn-Ser-hle-Eaa-Nle] |
| 385 | H-Phe-[Orn-Ser-hle-Mcf-Leu] |
| 386 | H-Phe-[Orn-Ser-hle-Ocf-Nle] |
| 387 | H-Phe-[Orn-Ser-hle-Pff-Leu] |
| 388 | H-Phe-[Orn-Ser-hle-Pff-Nle] |
| 389 | H-Phe-[Orn-Ser-hle-Pff-Phe] |
| 390 | H-Phe-[Orn-Ser-hle-Trp-Nle] |
| 392 | Ohf-[Orn-Hyp-hle-Trp-Nle] |
| 393 | Tmg-Phe-[Orn-Hyp-cha-Trp-Phe] |

In connection with the present invention, however, it was also surprisingly found that linear, thus structurally flexible, peptides can be as potent inhibitors as structurally fixed cyclic peptides. The reason for this may be the substitution of the C-terminal charged arginine by hydrophobic amino acids, amino acid derivatives or amino acid analogs. Examples for such linear peptidic inhibitors according to the invention are in particular the compounds shown in the following table:

| | |
|---|---|
| 51 | Ac-Phe-Orn-Pro-cha-Trp-Phe-NH2 [SEQ ID NO: 10] |
| 52 | Ac-Phe-Orn-Aze-cha-Bta-Phe-NH2 |
| 53 | Ac-Phe-Orn-Pro-cha-Bta-2Ni—NH2 |
| 54 | Ac-Phe-Orn-Pro-cha-Bta-Cha-NH2 |
| 55 | Ac-Phe-Orn-Pip-cha-Trp-Phe-NH2 |
| 61 | Ac-Phe-Orn-Pro-cha-Trp-Phe-NH2 [SEQ ID NO: 11] |
| 62 | Ac-Phe-Orn-Pro-cha-Bta-Phe-NH2 |
| 64 | Ac-Phe-Orn-Pro-cha-Trp-2Ni—NH2 |
| 65 | Ac-Phe-Orn-Pro-cha-Trp-Cha-NH2 |
| 66 | Ac-Thi-Orn-Aze-cha-Bta-Phe-NH2 |
| 67 | Ac-Thi-Orn-Pip-cha-Bta-Phe-NH2 |
| 68 | Ac-Phe-Orn-Pro-cha-Trp-Eap-NH2 |
| 69 | Me2-Phe-Orn-Pro-cha-Trp-Phe-NH2 [SEQ ID NO: 12] |
| 70 | Ph2-CH—CH2—CO-Orn-Pro-cha-Trp-Phe-NH2 |
| 71 | Ac-Ebw-Orn-Pro-cha-Trp-Phe-NH2 |
| 72 | Ac-Phe-Orn-Pro-cha-Trp-NH—CH2—CH2—Ph |
| 73 | Ac-Phe-Orn-Aze-cha-Bta-NH—CH2—CH2—Ph |
| 74 | H-Phe-Orn-Pro-cha-Trp-Phe-NH2 [SEQ ID NO: 13] |
| 75 | H—Me-Phe-Orn-Pro-cha-Trp-Phe-NH2 [SEQ ID NO: 14] |
| 76 | Bu-NH—CO-Phe-Orn-Pro-cha-Trp-Phe-NH2 [SEQ ID NO: 15] |
| 77 | Ac-Thi-Orn-Pro-cha-Trp-Phe-NH2 |
| 78 | Ac-Ebw-Orn-Pro-cha-Trp-Phe-NH2 |
| 79 | Ac-Phe-Orn-Ala-cha-Trp-Phe-NH2 [SEQ ID NO: 16] |
| 80 | Ac-Phe-Orn-Pro-cha-Trp-Thi-NH2 |
| 81 | Ac-Phe-Orn-Aze-cha-Pcf-Phe-NH2 |
| 82 | Ac-Phe-Orn(Ac)-Pro-cha-Trp-Phe-NH2 [SEQ ID NO: 17] |
| 83 | Ac-Phe-Orn-Aze-cha-Trp-Phe-NH2 |
| 84 | Ac-Phe-Trp-Pro-cha-Trp-Phe-NH2 [SEQ ID NO: 18] |
| 85 | Ph—NH—CO-Phe-Orn-Pro-cha-Trp-Phe-NH2 [SEQ ID NO: 19] |
| 86 | Bu-O—CO-Phe-Orn-Pro-cha-Trp-Phe-NH2 [SEQ ID NO: 20] |
| 87 | Ac-Phe-Lys-Pro-cha-Trp-Phe-NH2 [SEQ ID NO: 21] |
| 88 | Ac-Phe-Arg-Pro-cha-Trp-Phe-NH2 [SEQ ID NO: 22] |
| 89 | Ac-Phe-Gln-Pro-cha-Trp-Phe-NH2 [SEQ ID NO: 23] |
| 90 | Ac-Phe-Ser-Pro-cha-Trp-Phe-NH2 [SEQ ID NO: 51] |
| 91 | Ac-Phe-Glu-Pro-cha-Trp-Phe-NH2 [SEQ ID NO: 52] |
| 92 | Ac-Phe-Orn-Pip-cha-Trp-Phe-NH2 |
| 93 | Ac-Phe-Orn-Hyp-cha-Trp-Phe-NH2 |
| 94 | Ac-Phe-Orn-Pro-cha-Trp-1Ni—NH2 |
| 95 | Ac-Phe-Orn-Aze-cha-Bta-Phe-NH—Me |
| 96 | CH3—SO2-Phe-Orn-Aze-cha-Bta-Phe-NH2 |
| 99 | Ac-Phe-Orn-Aze-cha-Pff-Phe-NH2 |
| 100 | Ac-Phe-Orn-Aze-cha-Mcf-Phe-NH2 |
| 101 | Ac-Phe-Orn(Ac)-Aze-cha-Bta-Phe-NH2 |
| 102 | Ac-Ebw-Orn-Pro-cha-Trp-Phe-NH2 |
| 103 | Ac-Phe-Trp-Pro-cha-Trp-Phe-NH2 [SEQ ID NO: 24] |
| 104 | Ac-Phe-Arg-Pro-cha-Trp-Phe-NH2 [SEQ ID NO: 25] |
| 105 | Ac-Phe-Orn-Pip-cha-Trp-Phe-NH2 |
| 106 | 3PP-Orn-Aze-cha-Bta-Phe-NH2 |
| 107 | Ac-Phe-Orn-Tic-cha-Trp-Phe-NH2 |
| 108 | Ac-Phe-Orn-Ser-cha-Trp-Phe-NH2 [SEQ ID NO: 26] |
| 109 | Ac-Phe-Orn-Pro-chg-Trp-Phe-NH2 [SEQ ID NO: 27] |
| 110 | Ac-Phe-Orn-Pro-hch-Trp-Phe-NH2 [SEQ ID NO: 28] |
| 111 | Ac-Phe-Orn-Pro-cha-Trp-Phg-NH2 |
| 112 | Ac-Phe-Bta-Aze-cha-Bta-Phe-NH2 |
| 113 | Ac-Phe-Trp-Pro-cha-Bta-Phe-NH2 [SEQ ID NO: 29] |
| 115 | Ac-Phe-Orn-Pip-cha-Trp-Phe-OH |
| 116 | Ac-Phe-Orn-Tic-cha-Trp-Phe-OH |
| 117 | Ac-Phe-Orn-Ser-cha-Trp-Phe-OH [SEQ ID NO: 30] |
| 118 | Ac-Phe-Orn-Pro-chg-Trp-Phe-OH [SEQ ID NO: 31] |
| 119 | Ac-Phe-Eec-Pro-cha-Bta-Phe-NH2 |
| 120 | Ac-Phe-Nle-Pro-cha-Bta-Phe-NH2 |
| 121 | Ac-Phe-Har-Pro-cha-Bta-Phe-NH2 |
| 122 | Ac-Phe-Arg-Pro-cha-Bta-Phe-NH2 [SEQ ID NO: 32] |
| 123 | Ac-Phe-Cys(Acm)-Pro-cha-Bta-Phe-NH2 [SEQ ID NO: 33] |
| 124 | Ac-Phe-Mpa-Pro-cha-Bta-Phe-NH2 |
| 125 | Ac-Eby-Orn-Pro-cha-Bta-Phe-NH2 |
| 126 | Ac-Phg-Orn-Pro-cha-Bta-Phe-NH2 |
| 127 | Ac-Phe-Paf-Pro-cha-Bta-Phe-NH2 |
| 128 | H2N—CO-Phe-Orn-Pro-cha-Bta-Phe-NH2 |
| 129 | Me—O—CO-Phe-Orn-Pro-cha-Bta-Phe-NH2 |
| 130 | (—CO—CH2—NH—CO—)-Phe-Orn-Pro-cha-Bta-Phe-NH2 |
| 132 | Ac-Phe-Orn-Pro-hch-Trp-Phe-OH [SEQ ID NO: 34] |
| 133 | (—CO—CH2—CH2—CO—)-Phe-Orn-Pro-cha-Bta-Phe-NH2 |
| 134 | tBu-CO-Phe-Orn-Pro-cha-Bta-Phe-NH2 |
| 135 | Ac-Lys-Phe-Orn-Aze-cha-Bta-Phe-NH2 |
| 136 | Ac-Gly-Phe-Orn-Aze-cha-Bta-Phe-NH2 |
| 137 | Ac-Arg-Phe-Orn-Aze-cha-Bta-Phe-NH2 |
| 138 | Ac-His-Phe-Orn-Aze-cha-Bta-Phe-NH2 |
| 139 | Ac-Ser-Phe-Orn-Aze-cha-Bta-Phe-NH2 |
| 140 | Ac-Guf-Phe-Orn-Aze-cha-Bta-Phe-NH2 |
| 141 | Ac-Dab-Phe-Orn-Aze-cha-Bta-Phe-NH2 |
| 142 | FH2C—CO-Phe-Orn-Pro-cha-Bta-Phe-NH2 |
| 143 | Ac-Phe-Orn(Et2)-Pro-cha-Trp-Phe-NH2 [SEQ ID NO: 35] |
| 148 | Ac-Phe-N(nBu)—CH2—CO-Pro-cha-Trp-Phe-NH2 [SEQ ID NO: 53] |
| 149 | Ac-Phe-Orn-Pro-hle-Bta-Phe-NH2 |
| 150 | Ac-Phe-Arg(CH2—CH2)-Pro-cha-Bta-Phe-NH2 [SEQ ID NO: 37] |
| 151 | Ac-Ala-Phe-Orn-Aze-cha-Bta-Phe-NH2 |
| 152 | Ac-Arg-Phe-Orn-Aze-cha-Bta-Phe-NH2 |
| 153 | Ac-Cit-Phe-Orn-Aze-cha-Bta-Phe-NH2 |
| 154 | Ac-Gly-Phe-Orn-Aze-cha-Bta-Phe-NH2 |
| 155 | Ac-Gly-Phe-Orn-Aze-chg-Bta-Phe-NH2 |
| 156 | Ac-Gly-Phe-Orn-Aze-hch-Bta-Phe-NH2 |
| 157 | Ac-Gly-Thi-Orn-Aze-cha-Bta-Phe-NH2 |

-continued

| | |
|---|---|
| 158 | Ac-His-Phe-Orn-Aze-cha-Bta-Phe-NH2 |
| 159 | Ac-Hyp-Phe-Orn-Aze-cha-Bta-Phe-NH2 |
| 160 | Ac-Lys-Phe-Orn-Aze-cha-Bta-Phe-NH2 |
| 161 | Ac-Mff-Orn-Pro-cha-Bta-Phe-NH2 |
| 162 | Ac-Mff-Orn-Pro-hle-Bta-Phe-NH2 |
| 163 | Ac-Mff-Orn-Pro-hle-Mcf-Mff-NH2 |
| 164 | Ac-Mmy-Orn-Pro-hle-Pff-Phe-NH2 |
| 165 | Ac-NMF-Orn-Pro-cha-Bta-Phe-NH2 |
| 166 | Ac-Off-Orn-Pro-cha-Bta-Phe-NH2 |
| 167 | Ac-Off-Orn-Pro-hle-Bta-Phe-NH2 |
| 168 | Ac-Orn-Phe-Orn-Aze-cha-Bta-Phe-NH2 |
| 169 | Ac-Pff-Orn-Pro-cha-Bta-Phe-NH2 |
| 170 | Ac-Pff-Orn-Pro-hle-Bta-Phe-NH2 |
| 171 | Ac-Pff-Orn-Pro-hle-Mcf-Pff-NH2 |
| 206 | Ac-Phe-Ala-Pro-cha-Bta-Phe-NH2 [SEQ ID NO: 41] |
| 207 | Ac-Phe-Arg-Pro-hle-Bta-Phe-NH2 [SEQ ID NO: 42] |
| 208 | Ac-Phe-Arg-Pro-hle-Mcf-Phe-NH2 [SEQ ID NO: 43] |
| 209 | Ac-Phe-Cit-Hyp-hle-Bta-Phe-NH2 |
| 210 | Ac-Phe-Cit-Pro-cha-Bta-Phe-NH2 |
| 211 | Ac-Phe-Cit-Pro-hle-Bta-Phe-NH2 |
| 212 | Ac-Phe-Cit-Ser-hle-Bta-Phe-NH2 |
| 213 | Ac-Phe-Dab-Aze-cha-Bta-Phe-NH2 |
| 214 | Ac-Phe-Dab-Aze-hle-Bta-Phe-NH2 |
| 215 | Ac-Phe-Dab-Pro-cha-Bta-Phe-NH2 |
| 216 | Ac-Phe-Dap-Pro-cha-Bta-Phe-NH2 |
| 217 | Ac-Phe-Ech-Pro-cha-Bta-Phe-NH2 |
| 218 | Ac-Phe-Eep-Pro-cha-Bta-Phe-NH2 |
| 219 | Ac-Phe-Fcn-Aze-cha-Bta-Phe-NH2 |
| 220 | Ac-Phe-Fcn-Pro-cha-Bta-Phe-NH2 |
| 221 | Ac-Phe-Fco-Pro-cha-Bta-Phe-NH2 |
| 222 | Ac-Phe-Fco-Pro-cha-Bta-Phe-NH2 |
| 223 | Ac-Phe-Fcp-Aze-cha-Bta-Phe-NH2 |
| 224 | Ac-Phe-Ffa-Aze-cha-Bta-Phe-NH2 |
| 225 | Ac-Phe-Ffa-Pro-cha-Bta-Phe-NH2 |
| 226 | Ac-Phe-Ffa-Pro-hle-Bta-Phe-NH2 |
| 227 | Ac-Phe-G23-Pro-cha-Bta-Phe-NH2 |
| 228 | Ac-Phe-Guf-Pro-cha-Bta-Phe-NH2 |
| 229 | Ac-Phe-Har-Aze-cha-Bta-Phe-NH2 |
| 230 | Ac-Phe-His-Pro-cha-Bta-Phe-NH2 [SEQ ID NO: 44] |
| 231 | Ac-Phe-L22-Pro-cha-Bta-Phe-NH2 |
| 232 | Ac-Phe-OrA-Pro-cha-Bta-Phe-NH2 |
| 233 | Ac-Phe-OrE-Pro-cha-Bta-Phe-NH2 |
| 234 | Ac-Phe-Orn-Aze-hle-Bta-Phe-NH2 |
| 235 | Ac-Phe-Orn-Chy-cha-Bta-Phe-NH2 |
| 236 | Ac-Phe-Orn-Chy-hle-Pff-Phe-NH2 |
| 237 | Ac-Phe-Orn-G24-cha-Bta-Phe-NH2 |
| 238 | Ac-Phe-Orn-G25-cha-Bta-Phe-NH2 |
| 239 | Ac-Phe-Orn-G26-cha-Bta-Phe-NH2 |
| 240 | Ac-Phe-Orn-G27-cha-Bta-Phe-NH2 |
| 241 | Ac-Phe-Orn-G30-cha-Bta-Phe-NH2 |
| 242 | Ac-Phe-Orn-G31-cha-Bta-Phe-NH2 |
| 243 | Ac-Phe-Orn-Hse-cha-Bta-Phe-NH2 |
| 244 | Ac-Phe-Orn-Hyp-hle-Bta-Phe-NH2 |
| 245 | Ac-Phe-Orn-Hyp-hle-Pff-Phe-NH2 |
| 246 | Ac-Phe-Orn-NMA-cha-Bta-Phe-NH2 |
| 247 | Ac-Phe-Orn-NMS-cha-Bta-Phe-NH2 |
| 248 | Ac-Phe-Orn-Pro-cha-1Ni-Phe-NH2 |
| 249 | Ac-Phe-Orn-Pro-cha-Bta-1N—NH2 |
| 250 | Ac-Phe-Orn-Pro-cha-Bta-Bhf-NH2 |
| 251 | Ac-Phe-Orn-Pro-cha-Bta-Dff-NH2 |
| 252 | Ac-Phe-Orn-Pro-cha-Bta-Eaa-NH2 |
| 253 | Ac-Phe-Orn-Pro-cha-Bta-L19 |
| 254 | Ac-Phe-Orn-Pro-cha-Bta-Mcf-NH2 |
| 255 | Ac-Phe-Orn-Pro-cha-Bta-Mff-NH2 |
| 256 | Ac-Phe-Orn-Pro-cha-Bta-NH—CH(CH2OH)—CH2—Ph |
| 257 | Ac-Phe-Orn-Pro-Cha-Bta-NH-NBn-CO—NH2 |
| 258 | Ac-Phe-Orn-Pro-cha-Bta-Opa-NH2 |
| 259 | Ac-Phe-Orn-Pro-cha-Bta-Pcf-NH2 |
| 260 | Ac-Phe-Orn-Pro-cha-Bta-Pmf-NH2 |
| 261 | Ac-Phe-Orn-Pro-cha-Bta-Thi-NH2 |
| 262 | Ac-Phe-Orn-Pro-cha-Bta-Otf-NH2 |
| 263 | Ac-Phe-Orn-Pro-ctb-Bta-Phe-NH2 |
| 264 | Ac-Phe-Orn-Pro-ctb-Eaa-Phe-NH2 |
| 265 | Ac-Phe-Orn-Pro-ctb-Mcf-Phe-NH2 |
| 266 | Ac-Phe-Orn-Pro-ctb-Pff-Phe-NH2 |
| 267 | Ac-Phe-Orn-Pro-hch-Trp-Phe-OH [SEQ ID NO: 45] |
| 268 | Ac-Phe-Orn-Pro-hle-1Ni-Phe-NH2 |
| 269 | Ac-Phe-Orn-Pro-hle-6FW-Phe-NH2 |
| 270 | Ac-Phe-Orn-Pro-hle-Bta-1Ni—NH2 |
| 271 | Ac-Phe-Orn-Pro-hle-Bta-2Ni—NH2 |
| 272 | Ac-Phe-Orn-Pro-hle-Bta-5Ff-NH2 |
| 273 | Ac-Phe-Orn-Pro-hle-Bta-Aic-NH2 |
| 274 | Ac-Phe-Orn-Pro-hle-Bta-Cha-NH2 |
| 275 | Ac-Phe-Orn-Pro-hle-Bta-Chg-NH2 |
| 276 | Ac-Phe-Orn-Pro-hle-Bta-Eaa-NH2 |
| 277 | Ac-Phe-Orn-Pro-hle-Bta-Egy-NH2 |
| 278 | Ac-Phe-Orn-Pro-hle-Bta-Pcf-NH2 |
| 279 | Ac-Phe-Orn-Pro-hle-Bta-Pff-NH2 |
| 280 | Ac-Phe-Orn-Pro-hle-Bta-Phe-NH2 |
| 281 | Ac-Phe-Orn-Pro-hle-Bta-phe-OH |
| 282 | Ac-Phe-Orn-Pro-hle-Bta-Tyr-NH2 |
| 283 | Ac-Phe-Orn-Pro-hle-Dff-Phe-NH2 |
| 284 | Ac-Phe-Orn-Pro-hle-Eaa-Phe-NH2 |
| 285 | Ac-Phe-Orn-Pro-hle-Egc-Phe-NH2 |
| 286 | Ac-Phe-Orn-Pro-hle-Egy-Phe-NH2 |
| 287 | Ac-Phe-Orn-Pro-hle-Egz-Phe-NH2 |
| 288 | Ac-Phe-Orn-Pro-hle-Mcf-2Ni—NH2 |
| 289 | Ac-Phe-Orn-Pro-hle-Mcf-Cha-NH2 |
| 290 | Ac-Phe-Orn-Pro-hle-Mcf-Pff-NH2 |
| 291 | Ac-Phe-Orn-Pro-hle-Mcf-Phe-NH2 |
| 292 | Ac-Phe-Orn-Pro-hle-Mff-Phe-NH2 |
| 293 | Ac-Phe-Orn-Pro-hle-Mmy-Phe-NH2 |
| 294 | Ac-Phe-Orn-Pro-hle-Ocf-Phe-NH2 |
| 295 | Ac-Phe-Orn-Pro-hle-Off-Phe-NH2 |
| 296 | Ac-Phe-Orn-Pro-hle-Otf-Phe-NH2 |
| 297 | Ac-Phe-Orn-Pro-hle-Pff-2Ni—NH2 |
| 298 | Ac-Phe-Orn-Pro-hle-Pff-Cha-NH2 |
| 299 | Ac-Phe-Orn-Pro-hle-Pff-Eaa-NH2 |
| 300 | Ac-Phe-Orn-Pro-hle-Pff-Mmy-NH2 |
| 301 | Ac-Phe-Orn-Pro-hle-Pff-Pff-NH2 |
| 302 | Ac-Phe-Orn-Pro-hle-Pff-Phe-NH2 |
| 304 | Ac-Phe-Orn-Pro-hle-Phe-Phe-NH2 [SEQ ID NO: 46] |
| 305 | Ac-Phe-Orn-Pro-hle-Tff-Phe-NH2 |
| 306 | Ac-Phe-Orn-Pro-hle-Trp-Phe-NH2 [SEQ ID NO: 47] |
| 307 | Ac-Phe-Orn-Pro-ile-Trp-Phe-NH2 [SEQ ID NO: 48] |
| 308 | Ac-Phe-Orn-Pro-omf-Bta-Phe-NH2 |
| 309 | Ac-Phe-Orn-Ser-cha-Bta-Phe-NH2 |
| 310 | Ac-Ser-Phe-Orn-Aze-cha-Bta-Phe-NH2 |
| 312 | Ac-Thi-Orn-Pro-cha-Bta-Phe-NH2 |
| 313 | Ac-Thi-Orn-Pro-cha-Bta-Thi-NH2 |
| 314 | Ac-Thr-Phe-Orn-Aze-cha-Bta-Phe-NH2 |
| 316 | CH3CH2CO-Phe-Orn-Pro-cha-Bta-Phe-NH2 |
| 320 | FAc-Phe-Fib-Aze-cha-Bta-Phe-NH2 |
| 321 | FAc-Phe-Orn-Aze-cha-Bta-Phe-NH2 |
| 322 | FAc-Phe-Orn-Pro-cha-Bta-Phe-NH2 |
| 324 | Faz-Orn-Pro-cha-Bta-Phe-NH2 |
| 329 | Fbn-Phe-Cit-Pro-hle-Bta-Phe-NH2 |
| 339 | Fhu-Phe-Orn-Pro-cha-Bta-Phe-NH2 |
| 340 | Fid-Phe-Orn-Pro-cha-Bta-Phe-NH2 |
| 345 | H-Gly-Phe-Orn-Pro-cha-Bta-Phe-NH2 [SEQ ID NO: 49] |
| 346 | H-Nip-Phe-Cit-Pro-hle-Bta-Phe-NH2 |
| 348 | Hoo-Phe-Cit-Pro-hle-Pff-Phe-NH2 |
| 349 | Hoo-Phe-Orn-Hyp-hle-Pff-Phe-NH2 |
| 350 | Hoo-Phe-Orn-Pro-hle-Bta-Phe-NH2 |
| 351 | Hoo-Phe-Orn-Pro-hle-Mcf-Phe-NH2 |
| 352 | Hoo-Phe-Orn-Pro-hle-Pff-Phe-NH2 |
| 391 | H-Phe-Cit-Pro-hle-Bta-Phe-NH2 |

The linear peptides known from the prior art such as Finch et al. 1999 Journal of Medicinical Chemistry 42: 1965-1974; Wong et al. 1999 IDrugs 2: 686-693, U.S. Pat. No. 4,692,511, U.S. Pat. No. 5,663,148, WO 90/09162, WO 92/11858, WO 92/12168, WO 92/21361, WO 94/07518, WO 94/07815, WO 95/25957, WO 96/06629, WO 99/00406, and WO 99/13899 are in general significantly worse antagonists of C5a compared to cyclic peptides which are described in WO 99/00406 (e.g. Ac-Phe -[Lys-Pro-cha-Trp-arg] [SEQ ID NO: 54], Ac-Phe-[Orn-Pro-cha-Trp-arg] [SEQ ID NO: 55], Ac-Phe-[Orn-Pro-cha-Trp-Arg] [SEQ ID NO: 56], Ac-Phe-[Lys-Pro-cha-Trp-Arg] [SEQ ID NO: 57]). The in terms of antagonistic activity most active linear peptide described in WO 99/00406 has the sequence Me-Phe-Lys-Pro-cha-Trp-arg [SEQ ID NO: 58] and an $IC_{50}$ of 0.085 µM (measured with the cellular myeloperoxidase release assay with human PMNs). In contrast thereto, the comparable cyclic peptide Ac-Phe-[Lys-Pro-cha-Trp-arg] SEQ ID NO: 59] (also from WO 99/00406) has an $IC_{50}$ of 0.012 µM. In WO 99/00406 it is mentioned that the decreased structural flexibility of the cyclic peptide leads to the decrease, i.e. an improvement of the $IC_{50}$. This is reflected in the development of cyclic—meaning least flexible—inhibitors like Ac-Phe-[Lys-Pro-cha-Trp-arg] [SEQ ID NO: 60] and Ac-Phe-[Orn-Pro-cha-Trp-Arg] [SEQ ID NO: 61].

Thus, the inventors intentionally departed from the understanding of the prior art regarding at least one aspect of the present invention and accordingly provide a new class of compounds which can be used as C5aR antagonists.

The present invention describes for the first time peptidic and peptidomimetic C5aR antagonists having IC50s <200 nM, which do not have a positive net charge under physiological pH values (pH 7.4) and/or which C-terminal amino acid does not carry a positive charge. The $IC_{50}$ value is determined with a functional assay (Köhl 1997 The Anaphylatoxins. In: Dodds, A. W., Sim, R. B. (Eds.), Complement: A Practical Approach. Oxford, pp. 135-163). The compounds according to this invention can therefore be used as C5aR antagonists, especially under physiological conditions.

The compounds according to this invention do underline the finding that a suitable hydrophobic substitution of an aliphatic, aromatic or heteroaromatic kind can replace the C-terminal arginine of C5aR binding peptides.

Another feature of the compounds according to this invention, especially of the peptides and peptidomimetics, is the absence of agonistic activity in a cellular assay up to a concentration of at least 1430 nM. Example 12 shows by way of example results from measurements with selected peptides according to the present invention using a method for determinating C5aR agonistic activities. Obviously, the compounds according to the present invention do not show any agonistics activity up to the highest concentration used. Within the present invention the following compounds in accordance with the present invention are examples for peptides in accordance with the present invention which are pure antagonists: $HOCH_2(CHOH)_4$—C=N—O—$CH_2$—CO-Phe-[Orn-Pro-cha-Trp-Nle], Ph-$CH_2$—$CH_2$—CO-[Orn-Pro-cha-Trp-Nle], Ac-Phe-[Orn-Hyp-cha-Trp-Phe], H-Phe-[Orn-Pro-cha-Trp-Phe] [SEQ ID NO: 13], Ac-Phe-[Orn-Pro-cha-Trp-Phe] [SEQ ID NO: 7], Ac-Lys-Phe-[Orn-Pro-cha-Trp-Nle] [SEQ ID NO: 9], H-Phe-[Orn-Pro-cha-Trp-Nle], H-Phe-[Orn-Ser-cha-Trp-Nle], Ac-Phe-[Orn-Pro-cha-Trp-Eaf], Ac-Phe-Orn-Pro-cha -Trp-Phe-$NH_2$ [SEQ ID NO: 10], Ac-Phe-Orn-Pro-cha-Bta-Phe-$NH_2$, Ac-Ebw-Orn -Pro-cha-Trp-Phe-$NH_2$, Ac-Phe-Orn-cha-cha-Bta-Phe-$NH_2$, Ac-Phe-Arg-Pro-cha-Trp-Phe-$NH_2$ [SEQ ID NO: 22], Ac-Phe-Orn-Pip-cha-Trp-Phe-$NH_2$, Ac-Phe-Orn-Aze-cha-Trp-Phe-$NH_2$, Ac-Phe-Trp-Pro-cha-Trp-Phe-$NH_2$ [SEQ ID NO: 18], Ac-Thi-Orn-Pip-cha-Bta-Phe-$NH_2$, Ac-Phe-Orn-Pro-hle-Bta-Phe -$NH_2$, Ac-Phe-Arg($CH_2$—$CH_2$)-Pro-cha-Bta-Phe-$NH_2$ [SEQ ID NO: 37 ].

For a detailed analysis of the C5aR antagonism and the development of a pharmacophore model of the compound Ac-Phe-[Orn-Pro-cha-Trp-Arg] [SEQ ID NO: 61] the amino acids Phe, Trp and Arg were replaced by L-alanine, Pro was replaced by NMe-alanine and cha was replaced by D-alanine (single substitutions). The resulting peptides were analysed with a functional assay with regard to their C5aR antagonistic activity (example 11). From this approach it is apparent that the substitution of the amino acid side chains of Trp, cha, and Phe by methyl groups results in a pronounced loss of activity ($IC_{50}$ values >30 µM). In contrast to that the activity of the antagonist Ac-Phe-[Orn-Pro-cha-Trp-Arg] [SEQ ID NO: 61] is comparable to the activity of the molecule having Pro replaced by NMeAla ($IC_{50}$=20 nM compared to 25 nM). The substitution of Ala for Arg also leads to a significant loss in activity ($IC_{50}$=20 nM to $IC_{50}$=5.6 µM) which is nevertheless less pronounced than for the substitution of Trp and Phe.

Additional substitutions at the peptide Ac-Phe-[Orn-Pro-cha-Trp-Arg] [SEQ ID NO: 61] and similar compounds lead to a number of peptides and peptidomimetics, respectively, which, surprisingly, have noteworthy activities (example 11). Especially the following peptides show noteworthy inhibitory activity: Ac-Phe-[Orn-Pro-cha-Trp-Phe] [SEQ ID NO: 7], Ac-Phe-[Orn-Hyp-cha-Trp-Phe], Ac-Phe-[Orn-Pro-cha-Trp-Paf], Ac-Phe-[Orn-Pro-cha-Trp-Ecr], Ac-Phe-[Orn-Pro-cha-Trp-Ppa], Ac-Phe-[Orn-Pro-cha-Trp-Nle], Ac-Phe-[Orn-Pro-cha-Trp-Met] [SEQ ID NO: 8, Ac-Phe-[Orn-Pro-cha-Trp-Nva], Ac-Phe-[Orn-Pro-cha-Trp-Hle], Ac-Phe-[Orn-Pro-cha-Trp-Eaf], Ac-Phe-[Orn-Pro-cha-Trp-Ebd], Ac-Phe-[Orn-Pro-cha-Trp-Eag], Ac-Phe-[Orn-Pro-cha-Trp-Pmf], Ac-Phe-[Orn-Pro-cha-Trp-2Ni], Ac-Phe-[Orn-Pro-cha-Trp-Thi], H-Phe-[Orn-Pro-cha-Trp-Nle], Ac-Phe-[Orn-Pro-cha-Trp-Nle], Ac-Lys-Phe-[Orn-Pro-cha-Trp-Nle] [SEQ ID NO: 9], Ac-Phe-[Orn-Ser-cha-Trp-Phe] [SEQ ID NO: 26], $HOCH_2(CHOH)_4$—C=N—O—$CH_2$—CO-Phe-[Orn-Pro-cha-Trp-Nle], Ac-Phe-[Orn-Hyp($COCH_2OCH_2CH_2OCH_2CH_2OCH_3$)-cha-Trp-Phe], Ac-Phe-[Orn-Hyp($CONHCH_2COH(OH)CH_2OH$)-cha-Trp-Phe], Phenylpropionyl-[Orn-Pro-cha-Trp-Nle]Ac-Phe-Orn-Pro-hle-Bta-Phe-$NH_2$, Ac-Phe-Arg($CH_2$—$CH_2$)-Pro-cha-Bta-Phe-$NH_2$[SEQ ID NO: 37].

The oral absorption of peptides is influenced by a variety of factors like size, charge, and hydrophobicity. Nevertheless, the oral availability of a peptide cannot be predicted a priori. In general, peptides are regarded to have poor oral availablity (Burton et al. 1996 Journal of Pharmaceutical Sciences 85: 1337-1340). A model for the estimation of the oral absorption is the measurement of the AB permeability through a monolayer of gut epithelial cells (e.g. CaCo2 or TC-7) (example15, Lennernäs 1997 Journal of Pharmacy and Pharmacology 49: 627-38). The compounds according to the invention which can be used as C5aR antagonists, show a significantly increased AB permeability due to the hydrophobic substitution of the C-terminal arginine. For example, the antagonist Ac-Phe-[Orn-Hyp-cha-Trp-Phe] has a surprisingly high permeability of $14.3 \times 10^{-6}$ cm/s compared to the bad permeability of $0.52 \times 10^{-6}$ of the charged antagonist Ac-Phe-[Orn-Pro-cha-Trp-Arg] [SEQ ID NO: 61]. The high permeability is in terms of figures within a range close to the one of orally well available compounds. An example for an orally well available compound is Propanolol, which shows an AB permeability of $31.1 \times 10^{-6}$ cm/s in this test by Lennernäs.

It is also within the present invention that, in an embodiment, the compounds according to the present invention have introduced groups at X1 and/or X4 which improve water solubility. Especially useful for improving water solubility is the introduction of groups which are able to have strong interactions with water and which are strongly solvatized. Frequently used groups are: hydroxy, keto, carboxamido, ether, urea, carbamate, amino, substituted amino, guanidino, pyridyl, carboxyl. The disclosed groups can explicitly be introduced at all positions at X1 and/or X4, and both one and several of the water solubility increasing groups can be introduced. Examples for the introduction of several groups are the attachments of carbohydrate residues and ethylene glycols.

Therefore, the present invention especially also includes peptidic and peptidomimetic C5aR antagonists, especially according to the present invention, the solubility of which is improved by additional modifications. Such modifications are known to the one skilled in the art and include, for example, the introduction of the previously mentioned solubility improving groups. That this is an efficient method and, respectively, leads to highly active antagonists will be demonstraded by the following examples.

In accordance with example 13, compound 1 shows a solubility of 8% in aqueous HEPES buffer (pH 7.4). In contrast thereto, compound 40 has a solubility of 94% in HEPES buffer. Compound 2 which has an additional OH group compared to compound 1, shows a solubility of 13%. By adding more complex hydrophilic groups as shown for compound 4, the solubility is increased from 22% (compound 28) to 84% (compound 4). This is even true although compound 4 is not charged. Thus it is ensured that the peptide and peptidomimetics according to the present invention, despite their hydrophobic character, can be converted into a well water-soluble form.

In the following some terms are set forth the meaning of which is to be used for embodiments of the present invention, in particular those which are set forth herein in more detail. Although these terms are occasionally referred to as definitions, the meaning of the various terms is not necessarily limited thereto.

The term "comprises" means, in preferred embodiments, that the respective structural element is included, but the structure is not limited to it.

The term "substituted" means, in preferred embodiments, that one or several hydrogen atoms of a group or a compound is/are replaced by a different atom, group of atoms, molecule or group of molecules. In connection therewith, such an atom, group of atoms, molecules and group of molecules itself/themselves is/are referred to as substituents or substitutions. A prerequisite for any substitution is that the customary normal valence of the atom is not exceeded, and that the substitution results in a stable compound. By the substitution of two hydrogen atoms a carbonyl group (C=O) can be generated. Carbonyl groups are preferably not present in aromatic moieties.

Substituents or substitutions can preferably be selected individually or in any combination from the group consisting of hydroxyl, alkoxyl, mercapto, alkyl, alkenyl, alkynyl, alkoxy, alkylthio, alkylsulfinyl, cycloalkyl, heterocyclyl, aryl, arylalkyl, arylalkoxy, heteroaryl, aryloxy, halogen, trifluoromethyl, difluoromethyl, cyano, nitro, azido, amino, aminoalkyl, carboxamido, —C(O)H, acyl, oxazolyl oxyacyl, carboxyl, carbamate, trialkylsilyl, sulphonyl, sulfone amide and sulfuryl. Each substituent itself can be substituted further by one or several further substituents. This applies particularly to alkyl, cycloalkyl, heterocyclyl, aryl, heteroaryl and aryloxy. Furthermore any definitions set forth herein apply also to substituents.

The term "alkyl" refers, in preferred embodiments of the present invention, to a saturated aliphatic radical comprising from one to ten carbon atoms or a mono- or polyunsaturated aliphatic hydrocarbon radical comprising from two to twelve carbon atoms and at least one double and triple bond. The term "alkyl" includes both branched and unbranched alkyl groups. Unbranched alkyl groups having from one to eight carbon atoms are preferred. Unbranched alkyl groups having from one to six carbon atoms and branched alkyl groups having from three to six carbon atoms are particularly preferred. It should be understood that the term "alkyl" comprises any analogs which can be put together from combination terms of the prefix "alk" or "alkyl".

For example, the term "alkoxy" or "alkylthio" refers to an alkyl group which is linked by an oxygen or sulfur atom. "Alkanoyl" refers to an alkyl group which is linked by a carbonyl group (C=O).

The term "cycloalkyl" refers, in an embodiment of the present invention, to the cyclic derivatives of an alkyl group as defmed above, which is optionally unsaturated and/or substituted. Saturated cycloalkyl groups are preferred, particularly those having from three to eight carbon atoms. Particularly preferred are cycloalkyl groups having three to six carbon atoms.

The term "aryl" refers, in an embodiment of the present invention, to an aromatic group having from 6 to 14 carbon atoms, whereby "substituted aryl" refers to aryl groups bearing one or more substituents.

Each of the above defined groups "alkyl", "cycloalkyl", and "aryl" comprise the respective halogenated derivatives, whereby the halogenated derivatives may comprise one or several halogen atoms. The halogenated derivatives comprise any halogen radical as defined in the following.

The term "halo" refers, in a preferred embodiment of the present invention, to a halogen radical selected from fluoro, chloro, bromo, and iodo. Preferred halo groups are fluoro, chloro and bromo.

The term "heteroaryl" refers, in an embodiment of the present invention, to a stable 5- to 8-membered, preferably 5- or 6-membered monocyclic or 8- to 11-membered bicyclic aromatic heterocyclic radical, whereby each heterocycle may consist of both carbon atoms and from 1 to 4 heteroatoms selected from the group consisting of nitrogen, oxygen, and sulfur. The heterocycle may be linked by any atom of the cycle creacting a stable structure. Within the present invention preferred heteroaryl radicals are, for example, furanyl, thienyl, pyrrolyl, oxazolyl, thiazolyl, imidazolyl, pyrazolyl, isoxazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthridinyl, pteridinyl, carbazolyl, acridinyl, phenazinyl, phenothiazinyl and phenoxazinyl.

The term "heterocyclyl" refers, in an embodiment of the present invention, to a stable 5- to 8-membered, preferably 5- or 6-membered monocyclic or 8- to 11-membered bicyclic heterocyclic radical which may be either saturated or unsaturated, but is not aromatic. Each heterocycle consists of both carbon atoms and from 1 to 4 heteroatoms selected from the group consisting of nitrogen, oxygen and sulfur. The heterocycle may be linked by any atom of the cycle, which results in a stable structure. Preferred heterocyclic radicals within the present invention include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 2,5-dioxo-hexahydro-pyrimidin-4-yl, 2,6-dioxo-piperidin-4-yl, 2-oxo-hexahydro-pyrimidin-4-yl, 2,6-dioxo-hexahydro-pyrimidin-4-yl, 3,6-dioxo-piperazin-2-yl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

When the terms "heterocyclyl", "heteroaryl" and "aryl" are used together with other expressions and terms, the above definitions are further applicable. For example, "aroyl" refers to a phenyl or naphthyl group linked to a carbonyl group (C=O).

Each aryl or heteroaryl compound also includes its partially or fully hydrogenated derivatives. For example, quinolinyl may also include decahydroquinolinyl and tetrahydroquinolinyl. Naphthyl may also include the hydrogenated derivatives such as tetrahydronaphthyl.

Within the present invention by the terms "nitrogen" or "N" and "sulfur" or "S" any oxidized derivative of nitrogen like nitrones, N-oxides or of sulfur like sulfoxides, sulfones and the quaternized forms of any basic nitrogen and HCl- or TFA-salts are included.

Radicals can be any of mono-, di-, tri-, and tetra-radicals. Because of this it is possible that the meaning of various terms slightly changes. For example, a di-radical described as "propyl", inevitably means "propyplene" (e.g. —(CH$_2$)$_3$—).

Any wording which specifies the limits of a range such as, e. g., "from 1 to 5" means any integer from 1 to 5, i. e. 1, 2, 3, 4 and 5. In other words, any range that is defined by two integers comprises both the two integers defining said limits of the definition and any integer comprised in said range.

The present invention also comprises all isotopes of atoms of the described compounds. Isotopes are atoms having the same atomic number but different mass numbers. For example, tritium and deuterium are isotopes of hydrogen. Examples for carbon isotopes are $^{11}C$, $^{13}C$ and $^{14}C$.

The term "energetically accessible conformer" means any conformer of a compound that falls within about a 20 kcal/mol window above the lowest energy conformation. In connection therewith, e. g., a Monte Carlo or systematic conformational search using MM2, MM3, or MMFF force fields as implemented in molecular modeling software such as MacroModel® v 7.0, Schrödinger Inc. Portland, Oreg., USA (http://www.schrodinger.com) or the like, can be used.

Amino acids are well-known to the ones skilled in the art and defined by the fact that a molecule comprises both an amino and a carboxylic acid group. Both natural and unnatural amino acids can be meant. Examples are α-, β-, and ω-amino acids, whereby preferably α-amino acids, more preferably α-L-amino-acids are used. In case an amino acid is not specified in more detail (e.g. "tryptophane"), both the L-and the D-form are meant.

A natural amino acid is an L-amino acid selected from the group glycine, leucine, isoleucine, valine, alanine, phenylalanine, tyrosine, tryptophane, aspartic acid, asparagine, glutamic acid, glutamine, cysteine, methionine, arginine, lysine, proline, serine, threonine and histidine.

An unnatural amino acid is a non proteinogenic amino acid, which includes, but is not limited to, D-amino acids, N-alkyl-amino acids, homo amino acids, α,α-disubstituted amino acids and dehydro amino acids.

Amino acid derivatives are compounds which result from amino acids by modifying the N and/or C-termus. Non-limiting examples are the conversion of the carboxy group to salts, esters, acylhydrazides, hydroxamic acids or amides, and the conversion of the amino group to amides, ureas, thioureas, thioamides, sulfonamides, phosphoric acid amides, boric acid amides or alkyl amines. Parts of compounds, which result from modifications of amino acids at the C and/or N-termini, can also be referred to as amino acid units. Furthermore, the amino acids can also be derivatized at their side chains. If a derivatized amino acid is an amino acid, the side chain of which is derivatized one or several times, this kind of derivatization is usually specifically indicated herein. A preferred derivatisation of the side chain may be made in particular where the side chain bears a functional group. A preferred functional group is, for example, an amino group, a carboxy group, a thiol group or an alcohol group.

Amino acid analogues are compounds, which result from amino acids by replacing the amino and/or carboxy group by other groups which can mimic them. Non-limiting examples are the incorporation of thioamides, ureas, thioureas, acylhydrazides, esters, alkyl amines, sulfonamides, phosphoric acid amides, ketones, alcohols, boronic acid amides, benzodiazepines and other aromatic or non-aromatic heterocycles (for a review see M. A. Estiarte, D. H. Rich in Burgers Medicinal Chemistry, 6th edition, volume 1, part 4, John Wiley & Sons, New York, 2002).

Aromatic amino acids are amino acids which comprise aryl or heteroaryl groups. Non-limiting examples are phenylalanine, 2-fluoro-phenylalanine, 3-fluoro-phenylalanine, 4-fluoro-phenylalanine, 2-chloro-phenylalanine, 3-chloro-phenylalanine, 4-chloro-phenylalanine, tyrosine, histidine, tryptophane, homo-phenylalanine, homo-tyrosine, homo-histidine, homo-tryptophane, 1-naphtylalanine, 2-naphtylalanine, 2-thienylalanine, 3-thienylalanine, benzothienylalanine, furylalanine, thiazolylalanine, pyridylalanine, tetrahydroisochinoline-2-Carboxylic acid, 2-aminoindane-2-carboxylic acid, biphenylalanine, 3,3-diphenylalanine and corresponding D- and β-amino acids.

Hydrophobic amino acids are amino acids, which comprise hydrophobic alkyl-, cycloalkyl-, heterocyclyl, aryl or heteroaryl groups. Non-limiting examples are leucine, isoleucine, valine, phenylalanine, tyrosine, histidine, cysteine, cysteine(iPr), cysteine(tBu), methionine, proline, tryptophane, norleucine, norvaline, homoleucine, cyclohexyl alanine, cyclopentyl alanine, 1-naphtylalanine, 2-naphtylalanine, 2-thienylalanine, 3-thienylalanine, benzothienylalanine, allyl glycine, propargylglycine, 2-methyl-phenylalanine, 3-methyl-phenylalanine, 4-methyl-phenylalanine, homocyclohexylalanine, cyclohexyl glycine, n-cyclohexylglycine, octahydroindol-2-carboxylic acid and corresponding D- and β-amino acids.

The biological binding characteristics of an amino acid unit are those binding characteristics shown by the respective amino acid during the interaction with a biological molecule. Biological molecules are especially molecules exerting a biological function. Non-limiting examples of such biological molecules are protein- or peptide-based receptors.

Groups or units which mimic or imitate the biological binding characteristics of an amino acid, are defined as groups, which can establish with a receptor or interacting partner, preferably a biological receptor or a biological interaction partner, an interaction identical or similar to the amino acid itself. For the selection of such groups it is preferred to take into consideration those which are the most wide-spread ones in terms of most preferred interactions of the respective amino acids with biological receptors. For example, the oxygen atom of a carbonyl group of an amino acid can function as hydrogen bond acceptor, whereas the NH proton can establish interactions as hydrogen bond donor. Amino acids can additionally interact with receptors via their side chains. Phenylalanine and tryptophane can establish both hydrophobic interactions via the methylene side chain or the aromatic groups and π-π-interactions via the aromatic groups. Additionally, the indole group of the tryptophane can serve as a hydrogen bond donor via its NH group. Cyclohexyl alanine and norleucine can, in principle, establish hydrophobic interactions with biological receptors via their alkyl and/or cycloalkyl side chains. Not only the complete side chain of an amino acid, but also parts of the side chain can establish important interactions.

If a group or a unit, which is to mimic or imitate the biological binding characteristics of an amino acid or shall exhibit this characteristic, is capable of establishing at least one of the above-mentioned interactions of the respective amino acid, then this group or unit can mimic its biological binding characteristics.

As used herein in connection with the definition of the groups, the term "and respective derivatives thereof" refers to the fact that all derivatives of the individual compounds, groups of compounds, parts of molecules, radicals or chemical groups as recited in the respective group, can each be present as derivatives.

As used herein the term "individually and independently" refers to the fact that the two or more substituents mentioned can be designed as described in the respective paragraph. The wording "individually and independently" shall only avoid unnecessary repetitions and discloses that any of the mentioned substituents can exhibit the described arrangement, whereby the arrangement for each substituent is made individually or is individually present and is not affected by the selection of one or several of the other substituents.

It is generally within the scope of the present invention that the substituents described for the individual compounds according to the invention, in particular for the generic structures, are also applicable to all of the generic formulas with the corresponding substituents, if not indicated to the contrary.

Spacers as used herein, are in preferred embodiments organic radicals having a molecular weight of approximately 1-300, which allow a covalent linkage between different chemical groups if not indicated to the contrary for the individual case. Examples are simple groups like

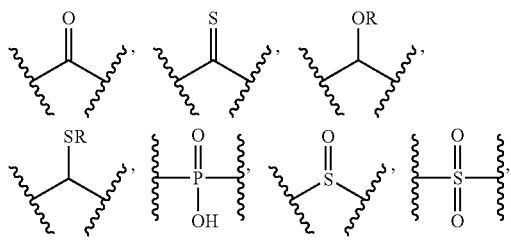

or more complex units like

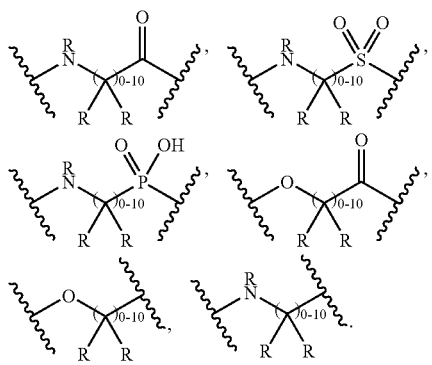

wherein R is, for each substitution, individually and independently a residue with a molecular weight of approximately 1-300. Preferably, R is a radical selected from the group comprising H, alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted heterocyclylalkyl, aryl, substituted aryl, arylalkyl, substituted arylalkyl, heteroaryl, substituted heteroaryl, heteroaryl alkyl, substituted heteroarylalkyl, acyl, substituted acyl, alkoxyalkyl, substituted alkoxyalkyl, aryloxyalkyl, substituted aryloxyalkyl, sulfhydrylalkyl, substituted sulfhydrylalkyl, hydroxyalkyl, substituted hydroxyalkyl, carboxyalkyl, substituted carboxyalkyl, carboxamidoalkyl, substituted carboxamidoalkyl, carboxyhydrazinoalkyl, ureidoalkyl, aminoalkyl, substituted aminoalkyl, guanidinoalkyl and substituted guanidinoalkyl.

Spacers are preferably selected from the group comprising

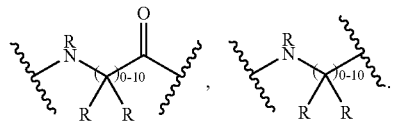

wherein R is preferably a radical selected from the group comprising H, alkyl, substituted alkyl, arylalkyl, substituted arylalkyl, heteroarylalkyl and substituted heteroarylalkyl.

Peptides carrying a positive net charge, can cause a histamine release (Jasani et al. 1979 Biochemical Journal 181: 623-632). In particular subcutaneous administration and/or implantation of subcutaneous depots is not possible with such compounds. In case of orally administered drugs absorption of the drugs is particularly important. The absorption of charged molecules is usually inferior to the one of uncharged molecules under otherwise identical conditions (Veber et al. 2002 Journal of Medicinal Chemistry 45: 2615-2623). Due to the missing net charge of the compounds according to the present invention they are also suitable for use as oral drugs.

The compounds according to the present invention can be used for the manufacture of medicaments, in particular for the manifacture of medicaments for the prevention and/or treatment of immuno inflammatory diseases. In particular the following diseases belong to the group of immuno inflammatory diseases: Autoimmune diseases, acute inflammatory diseases, trauma, local inflammations, septic shock and hemorrhagic shock. In preferred embodiments these diseases are selected from the group consisting of rheumatoid arthritis, systemic lupus erythematodes, multiple sclerosis, psoriasis, septic shock, asthma, vasculitis, dermatomyositis, inflammatory diseases of the intestine (IBD: inflammatory bowel disease), pemphigus, myasthenia grave, glomerulonephritis, acute respiratory insufficiency, cerebral apoplexy, cardiac infarction, reperfusion injury, neurocognitive dysfunctions, antiphospholipid syndrome, bums, inflammatory diseases of the eye such as, e.g., uveitis, age related macular degeneration, diabetic retinopathy, local manifestations of systemic diseases such as rheumatoid arthritis, SLE, diabetes of the eye, the brain, the vasculature, the heart, the lung, the kidneys, the liver, the gastrointestinal tract, the spleen, the skin or other organ systems, inflammatory diseases of the vasculature e.g. vasculitis, arteriosclerosis, and acute injuries of the central nervous system. All these diseases and/or clinical characteristics are mainly derived from the group of immuno inflammatory and inflammatory diseases, respectively, whereby the inflammatory response of these diseases may be either the cause or a secondary reaction thereof.

The present invention is also related to formulations, in particular pharmaceutical formulations, which comprise at least one of the compounds according to the invention. Frequently pharmaceutically active compounds are combined with other pharmaceutically acceptable ingredients, in order to ensure an improved efficacy like improved transport, shelf-life, release behavior over time and the like. A variety of such appropriate formulations are known to the one skilled in the art. Ingredients of such formulations are, among others, inert diluents, calcium carbonate, sodium carbonate, lactose, calcium phosphate, sodium phosphate, starch, alginate, gelatine, magnesium stearate and talcum. Certain ingredients can be added in order to allow for a retarded release of the pharmaceutically active active compounds. Respective examples are glycerol monostearate and glycerol distearate. For oral application in particular hard gelatine capsules are used, whereby the pharmaceutically active ingredient is admixed with calcium carbonate, calcium phosphate or kaolin. For soft gelatine capsules the pharmaceutically active compounds are admixed, e.g., with oils (peanut oil, liquid paraffin, olive oil). For the application in aqueous solutions the pharmaceutically active ingredients can be admixed in particular with the following components: carboxymethylcellulose, methylcellulose, hydropropylmethylcellulose, sodium alginate, polyvinylpyrrolidone, lecithin, polymer products of alkylene oxides and fatty acids as for example polyoxyethylenestearate, heptadecaethyleneoxycetanol, polyoxyethylenesorbitol monooleate and polyoxyethylenesorbitane monooleate. For the purpose of preservation different additives may be used. Respective examples are ethyl or n-propyl-p-hydroxybenzoate.

Certain formulations are used in order to allow for particular routes of administration. Examples of routes of administration of compounds according to the present invention are oral, subcutaneous, intravenous, topical, intramuscular, rectal and inhalativ administration. The compounds according to the present invention can be present as pharmaceutical acceptable salts.

The invention is now further illustrated by reference to the following figures and examples from which further advantages, features and embodiments may be taken.

EXAMPLES

Example 1

Material and Methods

Figure 1:
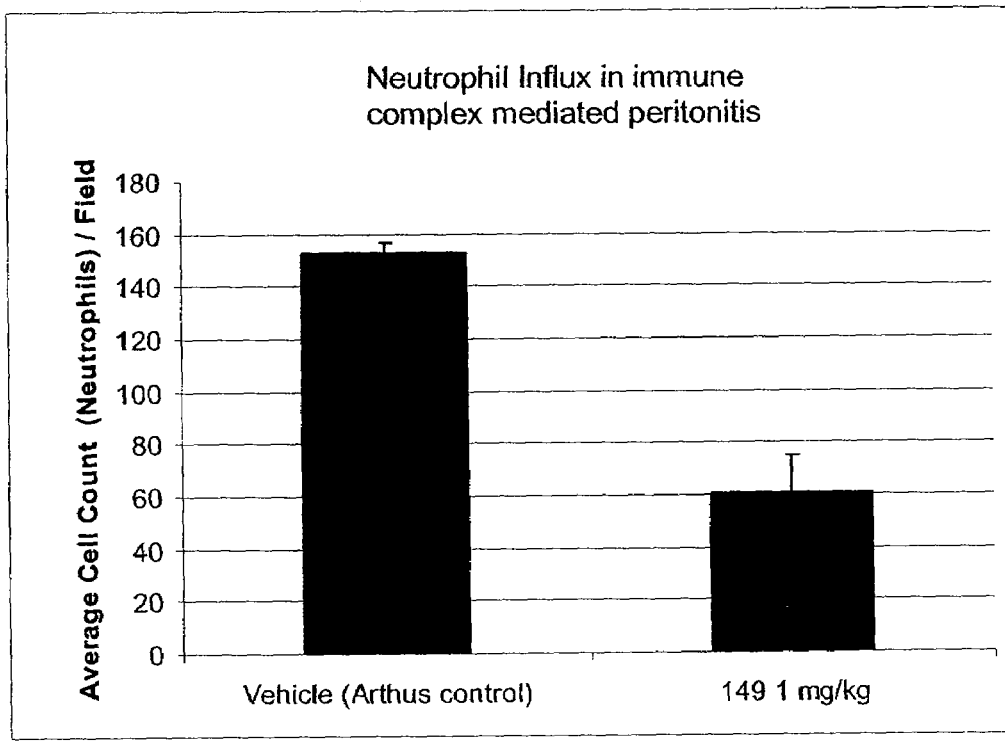
FIG. 1 shows a histogram indicating the influx of neutrophils in connection with immune complex mediated peritonitis expressed as average number of the polymorphonuclear cells/field, upon administration of compound 149 compared to the administration of the vehicle alone.

The materials and methods as well as general procedures described in the following were used in the following further examples:

Solvents:

All solvents were used in the specified quality without further purification.

Acetonitrile (gradient grade, J. T. Baker); dichloromethane (for synthesis, Merck Eurolab); diethylether (for synthesis, Merck Eurolab); N,N-dimethylformamide (LAB, Merck Eurolab); dioxane (for synthesis, Aldrich); methanol (for synthesis, Merck Eurolab).

Water was demineralised using a demineralization system (Milli-Q Plus, Millipore)

Reagents:

The used reagents were purchased from Advanced ChemTech (Bamberg, Germany), Sigma-Aldrich-Fluka (Deisenhofen, Germany), Bachem (Heidelberg, Germany), J. T. Baker (Phillipsburg, USA), Lancaster (Mühlheim/Main, Germany), Merck Eurolab (Darmstadt, Germany), Neosystem (Strassburg, France), Novabiochem (Bad Soden, Germany, from 2003 Merck Biosciences, Darmstadt, Germany) and Acros (Geel, Belgium, distributor Fisher Scientific GmbH, Schwerte, Germany), Peptech (Cambridge, Mass., USA), Synthetech (Albany, Oreg., USA), Pharmacore (High Point, N.C., USA), Anaspec (San Jose, Calif., USA) and used in the specified quality without further purification.

Unnatural amino acids or carboxylic acids for N-terminal modification which were not commercially available, were prepared according to standard protocols. For example, Fmoc-cis-Hyp-OH was prepared by reacting h-cis-Hyp-OH with Fmoc OSu [Paquet et al. 1982 Canadian Journal of Chemistry 60: 976-980A]. Fmoc-Phe(4-STrt-amidino)-OH was synthesized according to a known protocol [Pearson et al. 1996 Journal of Medicinal Chemistry 39:1372-1382]. Side chain modified cysteine derivatives were prepared by alkylation of Fmoc cystein-OH with alkyl halides.

If not indicated differently, concentrations are given as percent by volume.

RP-HPLC-MS Analyses:

For analytic chromatography a Hewlett Packard series 1100 system (degasser G1322A, quaternary pump G1311A, automatic sample loader G1313A, column heater G1316A, variable UV detector G1314A) was used together with an ESI-MS (Finnigan LCQ ion trap mass spectrometer). The system was controlled by "navigator ver. 1,1 sp1" software (Finnigan). Helium was used as impact gas in the ion trap. For separation a RP-18-column (Vydac 218 TP5215, 2.1×150 mm, 5 μm, C18, 300 A with a pre-column (Merck)) was used at 30° C. and a flow of 0.3 ml/min using a linear gradient for all chromatograms (5-95% B within 25 min, linear, whereby A: 0.05% TFA in water and B: 0.05% TFA in $CH_3CN$). UV detection was at λ=220 nm. Retention times ($R_t$) are indicated in the decimal system (e.g. 1.9 min=1 min 54 s) and are referring to detection in the mass spectrometer. The dead time between injection and UV detection (HPLC) was 1.65 min, and between UV detection and mass detection 0.21 min. The accuracy of the mass spectrometer was approx. ±0.2 amu.

Analyses by means of HPLC/MS were performed by injection of 5 μl, using a linear gradient from 95:5 to 5:95 in 9.5 min (A: 0.05% TFA in water and B: 0.05% TFA in acetonitrile), RP columns were from the company Phenomenex, Type Luna (C-18), 3 μm, 50×2.00 mm, flow 0.3 ml, HPLC at room temperature; mass spectrometer: ThermoFinnigan Surveyor with PDA detector (210-350 nm), MS; Advantage and/or LCQ Classic (both iontrap), ESI ionization, helium served as impact gas in the ion trap. Excalibur vers. 1.3 and 1.2, respectively, was used as software. Retention times ($R_t$) are indicated in the decimal system (e.g. 1.9 min=1 min 54 s).

Preparative HPLC:

Preparative HPLC separations were done using Vydac R18-RP columns with gradients of the following solvents: 0.05% TFA in $H_2O$ and B: 0.05% TFA in $CH_3CN$

TABLE 1

Abbreviations:

| | |
|---|---|
| Fig. | Figure |
| AAV | General procedure |
| Ac | Acetyl |
| Acm | Acetamidomethyl |
| Ac | Acetyl |
| d | Doublet |
| DCM | Dichloromethane |
| DIC | Diisopropylcarbodiimide |
| DIPEA | N,N-Diisopropylethylamine |
| DMF | N,N-Dimethylformamide |
| DMEM | Dulbecco's Modified Eagle Medium |
| DMSO | Dimethylsulfoxide |
| eq. | Equivalent(s) |
| Fmoc | 9-Fluorenylmethyloxycarbonyl |
| h | Hour(s) |
| HATU | O-(7-Azabenzotriazol-1-yl)-1,1,3,3-tetramethyluronium-Hexafluorophosphate |
| HBTU | O-(Benzotriazol-1-yl)-1,1,3,3-tetramethyluronium-Hexafluorophosphate |
| HEPES | N-2-2-Hydroxyethyl-1-piperazine-N'-2-ethanesulfonic acid |
| HOBt | 1-Hydroxybenzotriazole |
| HPLC | High-pressure liquid chromatography |
| m | Multiplet |
| Me | Methyl |
| min | Minute(s) |
| ml | Milliliter |
| NMI | N-Methylimidazole |
| NMP | N-Methylpyrrolidone |
| NMR | Nuclear magnetic resonance |
| Ph | Phenyl |
| s | Singlet |
| $^t$Bu | tert-Butyl |
| THF | Tetrahydrofuran |
| TFA | Trifluoroacetic acid |

TABLE 2

For proteinogenic amino acids the 3-letter codes were used:

| 3-letter code | Amino acids | 3-letter code | Amino acids |
|---|---|---|---|
| Ala | Alanine | Met | Methionine |
| Cys | Cysteine | Asn | Asparagine |
| Asp | Aspartic acid | Pro | Proline |
| Glu | Glutamic acid | Gln | Glutamine |
| Phe | Phenylalanine | Arg | Arginine |
| Gly | Glycine | Ser | Serine |
| His | Histidine | Thr | Threonine |
| Ile | Isoleucine | Val | Valine |
| Lys | Lysine | Trp | Tryptophane |
| Leu | Leucine | Tyr | Tyrosine |

TABLE 3

For non-proteinogenic amino acids a 3-letter code was used where the first letter indicates the stereochemistry of the C-alpha-atom. A capital first letter stands for the L-form, a lower case first letter stands for the D-form of the correspondent amino acid.

| | |
|---|---|
| 1Ni | 1-Naphthylalanine |
| 2Ni | 2-Naphthylalanine |
| 3PP | 3-Phenylpropionyl |
| 5Ff | Pentafluorophenylalanine |
| 6FW | 6-Fluoro-DL-tryptophane |
| Aic | 2-Aminoindan-2-carboxylic acid |
| Amf | Alpha-methyl-phenylalanine |
| Aoa | Aminooxyacetic acid |
| Aoc | 1-Aza-bicyclo-[3.3.0]-octan-2-carboxylic acid |
| Aze | Azetidine-2-carboxylic acid |
| Bal | beta-alanine |
| Bhf | beta-homophenylalanine |
| Bta | Benzothienylalanine |
| Bzl | Benzyl |
| Cha | beta-cyclohexylalanine |
| Chg | Cyclohexylglycine |
| Chy | cis-Hydroxyproline |
| Cit | Citrulline |
| Ctb | Cys(tBu) |
| Dab | 2,4-Diaminobutyric acid |
| Dap | 2,3-Diaminopropionic acid |
| Def | N,N-diethyl-phenylalanine |
| Dff | Phe(3,4-F) |
| Eaa | Phe(3,4-Cl) |
| Eaf | Allylglycine |
| Eag | 2-Propargylglycine |
| Eap | Phe(4-tBu) |
| Eay | (2S,4S)-4-Phenyl-pyrrolidine-2-carboxylic acid |
| Ebd | Cys(Et) |
| Ebo | Cys(4-picolyl) |
| Ebu | Cys(3-picolyl) |
| Ebw | 3,3-Diphenylalanine |
| Eby | (S)-3-Amino-3-phenylpropanic acid |
| Ecf | Cys(O-3-picolyl) |
| Ecg | Cys(2-picolyl) |
| Ecp | His(tau-4-Methoxybenzyl) |
| Ecr | His(tau-methyl) |
| Edn | Cys(CH$_2$—CH$_2$-4-Pyridyl) |
| Eec | Cys(1-Methylene-1H-benzotriazole) |
| Eep | Cys(O2-Acm); 3-(acetylamino-methanesulfonyl)-2-amino-propionic acid |
| Eew | Arg(NO$_2$) |
| Egc | DL-Trp(5-Me) |
| Egy | Phe(2,4-Cl) |
| Egz | Phe(3-NO$_2$) |
| Eth | Ethyl |
| FAc | F—CH$_2$—CO— |
| Fai | —CONH$_2$ |
| Faz | 3-Phenylpropionyl |
| Fbi | 2-(4-Pyridyl)acetyl |
| Fbn | Nicotinoyl |
| Fbo | Morpholine-4-carbonyl |
| Fbp | N,N-dimethyl-phenylalanine |
| Fci | Piperidine-3-carbonyl |
| Fck | HO—CH$_2$—(CHOH)$_4$—C═N—O—CH$_2$—CO— |
| Fcn | norArg(CH$_2$CH$_2$); 2-Amino-4-(4,5-dihydro-1H-imidazol-2-ylamino)-butyric acid |
| Fco | bisnorArg(CH$_2$CH$_2$); 2-Amino-3-(4,5-dihydro-1H-imidazol-2-ylamino)-propionic acid |
| Fcp | 2-Amino-5-[bis-(4,5-dihydro-1H-imidazol-2-yl)-amino]-pentanoic acid |
| Ffa | Arg(CH$_2$CH$_2$); 2-Amino-5-(4,5-dihydro-1H-imidazol-2-ylamino)-pentanoic acid |
| Fha | 2-Morpholin-4-yl-acetyl |
| Fhb | N-(2,3-Dihydroxy-propyl)-formamidyl |
| Fhi | 2-[2-(2-Methoxy-ethoxy)-ethoxy]-acetyl |
| Fhu | —C(NH)-NH$_2$ |
| Fib | Arg(4xMe), [(4-amino-4-carboxy-butylamino)-dimethylamino-methylene]-dimethyl-ammonium |
| Fid | Methoxyoxalyl |
| G23 | Orn(SO$_2$Me) |
| G24 | N-(n-Propyl)-glycine |
| G25 | N-(CH$_2$CH$_2$OCH$_3$)-glycine |
| G26 | N-(CH$_2$Furyl)-glycine |
| G27 | N-(CH$_2$Pyridyl)-glycine |
| G30 | N-(CH$_2$CH$_2$CH$_2$(2-oxo-pyrrolidine-1-yl))-glycine |
| G31 | N-(CH$_2$CH$_2$(3,4-dimethoxyphenyl))-glycine |
| Guf | Phe(4-guanidine) |
| Har | homo-arginine |
| Hch | homo-cyclohexylalanine |
| Hci | homo-citrulline |
| Hle | homo-leucine |
| Hoo | Hydroorotic acid; (S)-2,6-dioxo-hexahydro-pyrimidine-4-carbonyl |
| Hse | homo-Serine |
| HyA | Hyp(Ac) |
| Hym | Hyp(Me) |
| Hyp | trans-hydroxyproline |

TABLE 3-continued

For non-proteinogenic amino acids a 3-letter code was used where the first letter indicates the stereochemistry of the C-alpha-atom. A capital first letter stands for the L-form, a lower case first letter stands for the D-form of the correspondent amino acid.

| | |
|---|---|
| L19 | 1-(Methoxymethyl)-2-phenyl-ethylamino |
| L22 | norArg |
| Mcf | Phe(3-Cl) |
| Mff | Phe(3-F) |
| Mmf | Phe(3-Me) |
| Mmy | Phe(3-OMe) |
| Mpa | 3-(3-Pyridyl)-alanine |
| Nip | Nipecotic acid |
| Nle | Norleucine |
| NMA | N—Me-alanine |
| NMD | N—Me-asparagine |
| NMF | N—Me-phenylalanine |
| NMS | N—Me-serine |
| Nva | Norvaline |
| Ocf | Phe(2-Cl) |
| Off | Phe(2-F) |
| Ohf | (S)-2-Hydroxy-3-phenyl-propionyl |
| Oic | Octahydroindole-2-carboxylic acid |
| Omf | Phe(2-Me) |
| Opa | 3-(2-Pyridyl)-alanine |
| OrA | Orn(Ac) |
| OrE | Orn(Et$_2$); 2-Amino-5-diethylamino-pentanoic acid |
| Orn | Ornithine |
| Otf | Phe(2-CF3) |
| Paf | Phe(4-NH$_2$) |
| Pcf | Phe(4-Cl) |
| Pff | Phe(4-F) |
| Phg | Phenylglycine |
| Pip | Pipecolinic acid |
| Pmf | Phe(4-Me) |
| Ppa | 3-(4-Pyridyl)-alanine |
| Tff | Phe(3,4,5-F) |
| Thi | 2-Thienylalanine |
| Tic | 1,2,3,4-Tetrahydroisochinoline-3-carboxylic acid |
| Tiq | Tetrahydroisochinoline-1-carbonxylic acid |
| Tmg | =C(NMe$_2$)-NMe$_2$ |
| XX1 | 2-Amino-3-(4-piperidinyl)propionic acid |
| XX2 | 4-Guanidyl-piperidinyl-alanine |

The activity of the compounds was described in a simplified manner based upon the following conventions:

| | |
|---|---|
| IC$_{50}$ < 5 nM: | A |
| 5 nM < IC$_{50}$ ≦ 10 nM: | B |
| 10 nM < IC$_{50}$ ≦ 20 nM: | C |
| 20 nM < IC$_{50}$ ≦ 50 nM: | D |
| 50 nM < IC$_{50}$ ≦ 200 nM: | E |
| 200 nM < IC$_{50}$ ≦ 2000 nM: | F |
| 2000 nM < IC$_{50}$ | G |

General Procedure (AAV) 1: Synthesis of Linear Peptides

Linear peptides were synthesized using the Fmoc-$^t$Bu-strategy in batch-mode. The synthesis was done either manually in polypropylene syringes with a frit or via an automatic synthesizer (Syro from Multisyntech, Witten or Sophas from Zinsser, Frankfurt).

For the preparation of peptides carrying a C-terminal carboxylic acid, the C-terminal amino acid was either attached to a tritylchloride resin (app. 200 mg resin; loading of reactive groups about 1.5 mmol/g; coupling with 0.8 eq. Fmoc-amino acid and 3.0 eq. DIPEA in CH$_2$Cl$_2$ for 2 h; obtained loading of the amino acid about 0.2-0.4 mmol/g) or to Wang resin (200-500 mg resin; loading of reactive groups about 0.6 mmol/g; coupling by reacting 4 eq. Fmoc-amino acid, 4 eq. DIC and 3 eq. NMI in DMF for 3 h; loading of the amino acid about 0.2-0.6 mmol/g).

For the preparation of peptides carrying a C-terminal carboxylic amide, the first amino acid was attached to the resin via Fmoc deprotection from the Fmoc-Rink amide resin (about 200 mg resin; Fmoc deprotection with 20% piperidine in DMF for 20 min) and subsequent coupling of the Fmoc amino acid (reaction with 5 eq. Fmoc amino acid; 5 eq. HBTU and 15 eq. DIPEA in DMF for 30-60 min repeated once or more times).

After the coupling of the first amino acid, the synthesis of the desired peptide was done via a repeated sequence of events, as necessary, consisting of Fmoc deprotection and coupling of each of the required Fmoc amino acid or carboxylic acids. For the Fmoc deprotection the resin was reacted with 20% piperidine in DMF for 20 min. The coupling was carried out via single or multiple reaction with 5 eq. of the amino acid, 5 eq. HBTU and 15 eq. DIPEA in DMF for 30-60 min. For the introduction of the N-terminal acetyl group, the N-terminal free peptide, bound to the resin, was reacted with a solution of 10% acetic acid anhydride and 20% DIPEA in DMF for 20 min.

For the cleavage of the peptide from the resin and removal of the side chain protecting groups, a mixture of 95% TFA, 2.5% H$_2$O, 2.5% TIPS or a similar solution was added. Finally, TFA was removed using a rotary evaporator or the obtained peptide was precipitated by adding methyl-$^t$butyl-ether at 0° C. and isolated by centrifugation or pouring off the supernatant. For the transformation of the optionally obtained TFA-salts into the correspondent HCl salts, the peptide was solubilized in a mixture of 2 N HCl and MeCN and lyophilized.

Peptides with C-terminal carboxylic amides were directly purified via HPLC. Peptides carrying C-terminal carboxylic acids, however, were cyclized as raw product in accordance with AAV2.

General Procedure (AAV) 2: Cyclization of Peptides having a C-terminal Carboxylic Acid For cyclization about 80 mg of the linear peptide synthesized in accordance with AAV1, were solubilized in 5 ml DMF and 5 ml CH$_2$Cl$_2$. Subsequently, the pH was set to a value of approx. 8 with N-ethylmorpholine and 1 eq. HOBt was added together with 10 eq. DIC. After 2-16 h of stirring at room temperature the solvent removed using a rotary evaporator and the raw product purified via HPLC.

General Procedure (AAV) 3: Reductive Alkylation of Resin-Bound Peptides having a Free N-Terminus Linear peptides, synthesized in accordance with AAV 1, with a free N-terminus were incubated, prior to cleavage from the resin, with 10 eq. of the corresponding aldehyde in 5% acetic acid and 5% trimethylorthoformiate in THF. After approx. 4 h the obtained imine was reduced overnight with 5 eq. sodium cyanoborhydride.

After cleavage from the resin of the peptide completely synthesized in accordance with AAV1 the obtained raw product could be cyclized in accordance with AAV2. Usually an undesired cyclization to the N-terrminal secondary amine occurred apart from the desired cyclization. This byproduct could easily be removed by HPLC.

Example 2

Synthesis of Ac-Phe-[Orn-Pro-cha-Trp-Phe] (1)
[SEQ ID NO: 7]

After linear peptide synthesis in accordance with AAV 1, cyclization in accordance with AAV 2, and subsequent purification via HPLC, 50.9 mg of the desired product Ac-Phe-[Orn-Pro-cha-Trp-Phe] SEQ ID NO: 7] were obtained as white solid.

MS (ESI): m/z =888.3 [(M+H)$^+$].

Example 3

Synthesis of Ac-Phe-[Orn-Hyp-cha-Trp-Phe] (2)

The linear peptide Ac-Phe-Orn-Hyp-cha-Trp-Phe-OH was obtained by linear peptide synthesis in accordance with AAV 1 and cyclized in accordance with AAV 2. Due to the higher nucleophilicity of amines compared to alcohols, no byproduct together with the desired cyclized product was obtained through coupling of the free Hyp-OH group with the C-terminal carboxylic acid. Purification of the obtained raw product via HPLC yielded 26.9 mg of the desired white solid Ac-Phe-[Orn-Hyp-cha-Trp-Phe] (2).

MS (ESI): m/z=903.5 [(M+H)$^+$].

Example 4

Synthesis of Ph-CH$_2$-[orn-Pro-cha-Trp-Nle] (56)

The resin-bound peptide H-Orn-Pro-cha-Trp-Nle-trityl-resin was prepared by linear peptide synthesis in accordance with AAV1 and subjected to reductive alkylation using benzaldehyde. The cyclization in accordance with AAV 2, and subsequent purification via HPLC yielded 0.9 mg of the desired product 56 as white solid.

MS (ESI): m/z=753.4 [(M+H)$^+$].

Example 5

Synthesis of HOCH$_2$(CHOH)$_4$—C=N—O—CH$_2$—CO-Phe-[Orn-Pro-cha-Trp-Nle] (3)

The linear peptide H-Aoa-Phe-Orn-Pro-cha-Trp-Nle-OH was prepared in accordance with AAV 1, solubilized in 24 ml 1:1 MeCN/sodium acetate buffer (0.2 M, pH=4) and incubated with 58 mg (10 eq.) D-glucose. After stirring for 5 days, 2.4 ml acetone were added for quenching the unreacted aminooxyacetic acid-peptide, and after 5 min the solvent was evaporated under vacuum. The obtained raw product was purified via HPLC and subsequently cyclized in accordance with AAV 2. The purification of the raw product via HPLC yielded 1.9 mg of the desired white solid 3.

MS (ESI): m/z=1046.5 [(M+H)$^+$].

Example 6

Synthesis of 2-Acetamido-1-Methyl-Glucuronyl-Phe-[Orn-Pro-cha-Trp-Nle] (4)

The resin-bound peptide H-Phe-Orn-Pro-cha-Trp-Nle-trityl-resin was prepared by linear peptide synthesis in accordance with AAV 1, reacted with 39.8 mg (2.0 eq.) 2-acetamido-1-methyl-glucuronic acid (Schamann et al. 2003 European Journal of Organic Chemistry: 351-358), 60.8 mg (2.0 eq.) HATU and 105.7 µl (10 eq.) 2,4,6-collidine in 1.6 ml DMF. After stirring for 1.5 h the resin was washed with DMF (5×), MeOH (5×) und CH$_2$Cl$_2$ (3×) and the peptide was cleaved from the resin using 95% TFA, 2.5% H$_2$O and 2.5% TIPS. Cyclization in accordance with AAV 2, and HPLC purification yielded 29.0 mg of the desired product 4 as white solid.

MS (ESI): m/z=1043.0 [(M+H)$^+$].

Example 7

Synthesis of Ac-Phe-[Orn-Hyp (COCH$_2$OCH$_2$CH$_2$OCH$_2$CH$_2$OCH$_3$)-cha-Trp-Nle] (5)

The linear peptide Ac-Phe-Orn-Hyp-cha-Trp-Nle-OH was prepared in accordance with AAV 1, was cyclized in accordance with AAV 2 and the resulting cyclic peptide Ac-Phe-[Orn-Hyp-cha-Trp-Nle] was purified via HPLC. 35.4 µl (40 eq.) 2-(2-(2-Methoxyethoxy)ethoxy)acetic acid were reacted with 50.3 µl (120 eq.) thionyl chloride for 15 min at 40° C. After removal of the solvent under vacuum, 78.8 ml (80 eq.) DIPEA, 1 ml CH$_2$Cl$_2$ and 5.0 mg of the compound Ac-Phe-[Orn-Hyp-cha-Trp-Nle] were added. Stirring was continued for 3 days at room temperature and purification was done via HPLC. This yielded 1.6 mg of the desired white solid 5.

MS (ESI): m/z=1029.6 [(M+H)$^+$].

Example 8

Synthesis of Ac-Phe-[Orn-Hyp(CONH—CH$_2$CH (OH)—CH$_2$OH)-cha-Trp-Nle] (6)

The linear peptide Ac-Phe-Orn-Hyp-cha-Trp-Nle-OH was synthesized in accordance with AAV 1, cyclized in accordance with AAV 2, and the resulting cyclic peptide Ac-Phe-[Orn-Hyp-cha-Trp-Nle] was purified via HPLC. Subsequently, 5.0 mg of the peptide were reacted with 26.1 mg 4-isocyanatomethyl-2,2-dimethyl-[1,3]dioxolane and 1.88 µl (2.0 eq.) DIPEA in 0.3 ml MeCN. After stirring for 3 days at 40° C., the solvent was removed by a rotary evaporator and the obtained raw product was purified via HPLC. 0.22 mg of the desired white solid 6 were obtained.

MS (ESI): m/z=986.5 [(M+H)$^+$].

Example 9

Synthesis of Ac-Phe-[Orn-Pro-cha-Trp-Arg (CH$_2$CH$_2$)] (7) [SEQ ID NO: 62]

The linear peptide Ac-Phe-Orn-Pro-cha-Trp-Orn-OH was synthesized in accordance with AAV 1, cyclized in accordance with AAV 2, and the resulting cyclic peptide Ac-Phe-[Orn-Pro-cha-Trp-Orn] was purified via HPLC. Subsequently, 2.6 mg of the peptide were reacted with 22.6 mg (30 eq.) 2-(methylmercapto)-2-imidazoline-hydroiodide and 29.7 µl (60 eq.) DIPEA in 260 µl MeOH. After stirring for 2 days at 50° C., the solvent was removed by a rotary evaporator and the resulting raw product was purified via HPLC. 0.86 mg of the desired white solid 7 were obtained.

MS(ESD: m/z =922.8 [(M+H)].

Example 10

Synthesis of Ph-CH$_2$—CH$_2$—CO-[Orn-Pro-cha-Trp-Nle] (41)

The peptide Ph-CH$_2$—CH$_2$—CO-Orn-Pro-cha-Trp-Nle-OH was prepared by linear peptide synthesis in accordance with AAV1, whereby 3-phenylpropionic acid was used as N-terminal carboxylic acid. Cyclization was performed in accordance with AAV 2 and the raw product was purified via HPLC. 3.13 mg of the desired white solid 41 were obtained.

MS (ESI): m/z=796.5 [(M+H)$^+$].

Example 11

Determination of the IC$_{50}$ Value in an Enzyme Release Assay

The assay procedure is described in Köhl (Köhl 1997 The Anaphylatoxins. In: Dodds, A. W., Sim, R. B. (Eds.), Complement: A Practical Approach. Oxford, pp. 135-163). Basophilic leukemia cells from rats (RBL), which express the human C5aR (CD88), were cultivated in DMEM with 10% fetal bovine serum, 100 U/ml penicillin, 100 µg/ml streptomycin and 2 mM glutamine (all components of the medium from Biochrome, Berlin) until confluence at 37° C. and 10% CO$_2$. The following specifications all refer to a cell culture flask having a surface of 75 cm$^2$. Spent medium was decanted from cells. Cells were washed with 10 ml PBS (Dulbecco's PBS, Biochrome) and subsequently overlayed with 3 ml Cell Dissociation Solution (CDS, Sigma). Cells were incubated for 1 min at room temperature. Subsequently, CDS was removed and the cells were further incubated 10-15 min at 37° C. for detachment. In the assay, 20 µl of the solution containing the compound to be tested were used. This assay solution must not contain more than 2.8% DMSO. For the dilution process, the compounds were diluted in 1/3 or 1/2 steps. To 20 µl compound solution 75 µl of the RBL-cells were added which were treated as follows: after detachment the cells were vigorously tapped off and taken up in 10 ml HAG-CM (20 mM HEPES; 125 mM NaCl, 5 mM KCl, 1 mM CaCl$_2$, 1 mM MgCl$_2$, 0.5 mM Glucose, 0.25% BSA. HEPES-preparation: 2.3 g/l HEPES-salt+2.66 g/l HEPES acid) at 37° C. Cells were counted and centrifuged (200×g, 10 min). The cell pellet was resuspended in preheated HAG-CM (i.e. Hepes-buffered solution of NaCl and glucose with calcium and magnesium), and cell density was adjusted to 2×10$^6$ cells/ml. The cells were incubated at 37° C. for 5 min. 27 µl of a cytochalasin B-solution were added per ml cell suspension (100 µg/ml in DMSO, Sigma). The cells were incubated for further 3 min at 37° C. 75 µl of the cell suspension were added to 20 µl of the solution containing the compound to be tested, leading to a volume of 95 µl per well. After incubation of the cells for 10 min at 37° C. 10 µl hrC5a (10.5 nM in HAG-CM, Sigma) are added per well. Subsequently, the cells are incubated for 5 min at 37° C. Thereafter, the plates are put on ice and centrifugated at 1200×g and 4° C. for 3 min. 75 µl of the supernatant are added to 100 µl substrate solutions (2.7 mg/ml p-nitrophenyl-N-acetyl-β-D-glucosaminide (Sigma) in 42.5 mM Na-acetate pH 4.5). The plate further is incubated for 1 h at 37° C. 75 µl 0.4 M glycine pH 10.4 are added per well. The plate can subsequently be measured in a reader at 405 nm. The IC$_{50}$-value is determined by solving the four parameter equation: $y=((A-D)/(1+(x/C)^B))+D$.

The results of the IC$_{50}$-value determination are shown in table 4.

TABLE 4

Data for antagonistic activity of selected compounds acording to the present invention.

| No. | Compound | (M + H)+ in MS [amu] | activity (group) |
|---|---|---|---|
| 1 | Ac-Phe-[Orn-Pro-cha-Trp-Phe] [SEQ ID NO: 7] | 888.3 | D |
| 2 | Ac-Phe-[Orn-Hyp-cha-Trp-Phe] | 903.5 | D |
| 3 | HOCH2(CHOH)4—C=N—O—CH2—CO-Phe-[Orn-Pro-cha-Trp-Nle] | 1046.5 | E |
| 4 | X-Phe-[Orn-Pro-cha-Trp-Nle]; X = 2-Acetamido-1-Methyl-Glucuronyl | 1043.0 | D |
| 5 | Ac-Phe-[Orn-Hyp(COCH2OCH2CH2OCH2CH2OCH3)-cha-Trp-Nle] | 1029.6 | E |
| 6 | Ac-Phe-[Orn-Hyp(CONH—CH2CH(OH)—CH2OH)-cha-Trp-Nle] | 986.5 | E |
| 7 | Ac-Phe-[Orn-Pro-cha-Trp-Arg(CH2CH2)] [SEQ ID NO: 63] | 922.8 | F |
| 8 | Ac-Phe-[Orn-Pro-cha-Trp-Har] | 910.7 | F |
| 9 | Ac-Phe-[Orn-Pro-cha-Trp-Guf] | 944.6 | F |
| 10 | Ac-Phe-[Orn-Pro-cha-Trp-Cit] | 897.5 | F |
| 11 | Ac-Phe-[Orn-Pro-cha-Trp-Eew] | 941.5 | F |
| 12 | Ac-Phe-[Orn-Pro-cha-Trp-arg] | 896.7 | F |
| 13 | Ac-Phe-[Orn-Pro-cha-Trp-Hci] | 911.6 | F |
| 14 | Ac-Phe-[Orn-Pro-cha-Trp-Paf] | 902.7 | D |
| 15 | Ac-Phe-[Orn-Pro-cha-Trp-Ebo] | 934.6 | F |
| 16 | Ac-Phe-[Orn-Pro-cha-Trp-Ecf] | 950.6 | F |
| 17 | Ac-Phe-[Orn-Pro-cha-Trp-Ebu] | 934.7 | F |
| 18 | Ac-Phe-[Orn-Pro-cha-Trp-Ecg] | 934.6 | F |
| 19 | Ac-Phe-[Orn-Pro-cha-Trp-Edn] | 948.6 | F |
| 20 | Ac-Phe-[Orn-Pro-cha-Trp-Ecr] | 891.7 | E |
| 21 | Ac-Phe-[Orn-Pro-cha-Trp-Phe(4-Amidin)] [SEQ ID NO: 64] | 929.7 | F |
| 22 | Ac-Phe-[Orn-Pro-cha-Trp-Lys] [SEQ ID NO: 65] | 868.6 | G |
| 23 | Ac-Phe-[Orn-Pro-cha-Trp-Ppa] | 888.6 | E |
| 24 | Ac-Phe-[Orn-Pro-cha-Trp-Arg(Me2)] [SEQ ID NO: 66] | 924.7 | E |
| 25 | Ac-Phe-[Orn-Pro-cha-Trp-Dab] | 840.4 | E |
| 26 | Ac-Phe-[Orn-Pro-cha-Trp-Ecp] | 997.7 | F |
| 27 | Ac-Phe-[Orn-Pro-cha-Trp-XX1] | 894.6 | G |
| 28 | Ac-Phe-[Orn-Pro-cha-Trp-Nle] | 852.6 | D |
| 29 | Ac-Phe-[Orn-Pro-cha-Trp-Met] | 871.6 | E |

TABLE 4-continued

Data for antagonistic activity of selected compounds acording to the present invention.

| No. | Compound | (M + H)+ in MS [amu] | activity (group) |
|---|---|---|---|
|  | [SEQ ID NO: 8] |  |  |
| 30 | Ac-Phe-[Orn-Pro-cha-Trp-XX2] | 936.5 | G |
| 31 | Ac-Phe-[Orn-Pro-cha-Trp-Nva] | 839.5 | C |
| 32 | Ac-Phe-[Orn-Pro-cha-Trp-Hle] | 867.5 | D |
| 33 | Ac-Phe-[Orn-Pro-cha-Trp-Eaf] | 837.5 | B |
| 34 | Ac-Phe-[Orn-Pro-cha-Trp-Ebd] | 871.5 | D |
| 35 | Ac-Phe-[Orn-Pro-cha-Trp-Eag] | 835.5 | B |
| 36 | Ac-Phe-[Orn-Pro-cha-Trp-Pmf] | 901.6 | D |
| 37 | Ac-Phe-[Orn-Pro-cha-Trp-2Ni] | 937.5 | E |
| 38 | Ac-Phe-[Orn-Pro-cha-Trp-Thi] | 893.5 | D |
| 39 | Ac-Phe-[Orn-Pro-cha-Trp-Ala] | 811.7 | G |
|  | [SEQ ID NO: 67] |  |  |
| 40 | Ac-Phe-[Orn-Pro-cha-Trp-Arg] | 896.6 | C |
|  | [SEQ ID NO: 68] |  |  |
| 41 | Ph—CH2—CH2—CO-[Orn-Pro-cha-Trp-Nle] | 796.5 | C |
| 42 | H-Phe-[Orn-Pro-cha-Trp-Nle] | 811.5 | C |
| 43 | Ac-Lys-Phe-[Orn-Pro-cha-Trp-Nle] | 1015.7 | D |
|  | [SEQ ID NO: 9] |  |  |
| 44 | H-Phe-[Orn-Ser-cha-Trp-Nle] | 843.5 | D |
| 45 | Ac-Ala-[Orn-Pro-cha-Trp-Arg] | 820.6 | G |
|  | [SEQ ID NO: 69] |  |  |
| 46 | Ac-Phe-[Orn-NMeAla-cha-Trp-Arg] | 884.8 | D |
| 47 | Ac-Phe-[Orn-Pro-ala-Trp-Arg] | 814.8 | G |
|  | [SEQ ID NO: 70] |  |  |
| 48 | Ac-Phe-[Orn-Pro-cha-Ala-Arg] | 781.8 | G |
|  | [SEQ ID NO: 71] |  |  |
| 49 | Ac-Phe-[Orn-Pro-cha-Trp-Ala] | 811.7 | G |
|  | [SEQ ID NO: 72] |  |  |
| 56 | Ph—CH2-[Orn-Pro-cha-Trp-Nle] | 753.4 | D |
| 57 | Ph—CH2-[Orn-Pro-cha-Trp-Phe] | 787.5 | D |
| 58 | Ac-Phe-[Orn-Pro-cha-Trp-1Ni] | 937.7 | D |
| 59 | Ph—CH(OH)—CH2—CO-[Orn-Pro-cha-Trp-Nle] | 812.4 | D |
| 144 | Ac-Phe-[Orn-Hyp-cha-Trp-Nle] | 868.6 | C |
| 145 | 3PP-[Orn-Hyp-cha-Trp-Nle] | 811.6 | D |
| 146 | Ac-Phe-[Orn-Pro-cha-Trp-Tyr] | 902.7 | D |
|  | [SEQ ID NO: 36] |  |  |
| 147 | Ac-Phe-[Orn-Pro-Omf-Trp-Nle] | 860.6 | C |
| 172 | Ac-Phe-[Cys-Pro-cha-Bta-Phe-Cys]-NH2 | 1011.6 | E |
|  | [SEQ ID NO: 38] |  |  |
| 173 | Ac-Phe-[Orn-Asn-cha-Trp-Nle] | 871 | E |
| 174 | Ac-Phe-[Orn-Aze-cha-Trp-Nle] | 839.5 | E |
| 175 | Ac-Phe-[Orn-Chy-cha-Trp-Nle] | 869.5 | E |
| 176 | Ac-Phe-[Orn-HyA-cha-Trp-Phe] | 945.6 | E |
| 177 | Ac-Phe-[Orn-Hyp-hle-Bta-Phe] | 894.7 | E |
| 178 | Ac-Phe-[Orn-Hyp-hle-Mcf-Phe] | 874.2 | E |
| 179 | Ac-Phe-[Orn-Hyp-hle-Pff-Nle] | 823.1 | E |
| 180 | Ac-Phe-[Orn-Hyp-hle-Pff-Phe] | 857 | E |
| 181 | Ac-Phe-[Orn-Hyp-hle-Trp-Phe] | 877.9 | D |
| 182 | Ac-Phe-[Orn-Hyp-Mmf-Trp-Nle] | 877.5 | E |
| 183 | Ac-Phe-[Orn-Hyp-Mmf-Trp-Phe] | 911.8 | E |
| 184 | Ac-Phe-[Orn-NMD-cha-Trp-Nle] | 885.5 | E |
| 185 | Ac-Phe-[Orn-Pip-hle-Bta-Phe] | 892.7 | E |
| 186 | Ac-Phe-[Orn-Pro-cha-Pff-Nle] | 833.3 | E |
| 187 | Ac-Phe-[Orn-Pro-cha-Pff-Phe] | 867.4 | E |
| 188 | Ac-Phe-[Orn-Pro-cha-Trp-1Ni] | 937.7 | E |
| 189 | Ac-Phe-[Orn-Pro-cha-Trp-Cha] | 893.6 | E |
| 190 | Ac-Phe-[Orn-Pro-cha-Trp-Chg] | 879.7 | E |
| 191 | Ac-Phe-[Orn-Pro-cha-Trp-Cit] | 897.5 | F |
| 192 | Ac-Phe-[Orn-Pro-cha-Trp-Ecr] | 891.7 | D |
| 193 | Ac-Phe-[Orn-Pro-cha-Trp-Leu] | 853.5 | E |
|  | [SEQ ID NO: 39] |  |  |
| 194 | Ac-Phe-[Orn-Pro-cha-Trp-nle] | 853.5 | E |
| 195 | Ac-Phe-[Orn-Pro-cha-Trp-Phe] | 887.7 | D |
|  | [SEQ ID NO: 40] |  |  |
| 196 | Ac-Phe-[Orn-Pro-hle-Bta-Nle] | 844.7 | E |
| 197 | Ac-Phe-[Orn-Pro-hle-Bta-Phe] | 879.5 | E |
| 198 | Ac-Phe-[Orn-Pro-hle-Pff-Phe] | 840.9 | E |
| 199 | Ac-Phe-[Orn-Pro-hle-Trp-Nle] | 828.1 | D |
| 200 | Ac-Phe-[Orn-Ser-cha-Trp-Nle] | 843.5 | E |
| 201 | Ac-Phe-[Orn-Ser-cha-Trp-Nle] | 843.5 | E |
| 202 | Ac-Phe-[Orn-Ser-hle-Trp-Nle] | 817.5 | E |
| 203 | Ac-Phe-[Orn-Thr-cha-Trp-Nle] | 858.2 | E |
| 204 | Ac-Phe-[Orn-Tic-cha-Trp-Nle] | 915.5 | E |

TABLE 4-continued

Data for antagonistic activity of selected compounds acording to the present invention.

| No. | Compound | (M + H)+ in MS [amu] | activity (group) |
|---|---|---|---|
| 205 | Ac-Phe-[Orn-Tic-cha-Trp-Nle] | 915.5 | E |
| 311 | Ac-Thi-[Orn-Pro-hle-Bta-Phe] | 884.8 | E |
| 315 | Bzl-[Orn-Pro-cha-Bta-Nle] | 771.8 | E |
| 317 | Def-[Orn-Ser-hle-Trp-Nle] | 831.9 | E |
| 318 | Eby-Phe-[Orn-Hyp-cha-Trp-Phe] | 1008.9 | E |
| 319 | Eth-Phe-[Orn-Pro-hle-Pff-Nle] | 792.4 | E |
| 323 | Fai-Phe-[Orn-Hyp-cha-Trp-Phe] | 904.4 | E |
| 325 | Fbi-Phe-[Orn-Pro-cha-Trp-Nle] | 930.5 | E |
| 326 | Fbn-Phe-[Orn-Hyp-cha-Trp-Phe] | 966.8 | E |
| 327 | Fbn-Phe-[Orn-Pro-cha-Trp-Nle] | 916.5 | E |
| 328 | Fbn-Phe-[Orn-Pro-cha-Trp-Nle] | 916.5 | C |
| 330 | Fbo-Phe-[Orn-Pro-cha-Trp-Nle] | 924.5 | E |
| 331 | Fbp-[Orn-Pro-cha-Trp-Nle] | 839.4 | E |
| 332 | Fci-[Phe-Orn-Hyp-cha-Trp-Phe] | 973.1 | E |
| 333 | Fck-[Phe-Orn-cha-Trp-Nle] | 1046.4 | E |
| 334 | Fck-Phe-[Orn-Pro-cha-Trp-Nle] | 1047.1 | E |
| 335 | Fha-Phe-[Orn-Hyp-cha-Trp-Phe] | 988.9 | E |
| 336 | Fhb-[Phe-Orn-Hyp-cha-Trp-Phe] | 979.1 | E |
| 337 | Fhi-Phe-[Orn-Hyp-cha-Trp-Phe] | 1022 | E |
| 338 | Fhu-Phe-[Orn-Pro-hle-Pff-Nle] | 807 | E |
| 341 | H-Amf-[Orn-Aze-hle-Pff-Nle] | 750.9 | E |
| 342 | H-Bal-Phe-[Orn-Hyp-hle-Trp-Nle] | 872.5 | E |
| 343 | H-Bal-Phe-[Orn-Pro-hle-Pff-Nle] | 836 | E |
| 344 | H-Eby-[Orn-Hyp-hle-Trp-Nle] | 801.9 | E |
| 347 | Hoo-Phe-[Orn-Hyp-hle-Pff-Nle] | 921 | E |
| 353 | H-Phe-[Lys-Hyp-hle-Pff-Nle] | 795.2 | E |
| 354 | H-Phe-[Orn-Hym-hle-Mcf-Nle] | 811.4 | E |
| 355 | H-Phe-[Orn-Hym-hle-Pff-Phe] | 829.1 | E |
| 356 | H-Phe-[Orn-Hyp-cha-Trp-Nle] | 828.1 | D |
| 357 | H-Phe-[Orn-Hyp-cha-Trp-Phe] | 862.1 | D |
| 358 | H-Phe-[Orn-Hyp-ctb-Pff-Nle] | 813.2 | E |
| 359 | H-Phe-[Orn-Hyp-ctb-Trp-Nle] | 834.2 | D |
| 360 | H-Phe-[Orn-Hyp-ctb-Trp-Phe] | 868 | D |
| 361 | H-Phe-[Orn-Hyp-hle-Mcf-Leu] | 796.4 | E |
| 362 | H-Phe-[Orn-Hyp-hle-Pff-Chg] | 807 | E |
| 363 | H-Phe-[Orn-Hyp-hle-Pff-Hle] | 795.1 | E |
| 364 | H-Phe-[Orn-Hyp-hle-Pff-Leu] | 781.2 | E |
| 365 | H-Phe-[Orn-Hyp-hle-Pff-Nle] | 781.1 | E |
| 366 | H-Phe-[Orn-Hyp-hle-Pff-Phe] | 815 | E |
| 367 | H-Phe-[Orn-Hyp-hle-Trp-Hle] | 815.9 | E |
| 368 | H-Phe-[Orn-Hyp-hle-Trp-Leu] | 802.1 | D |
| 369 | H-Phe-[Orn-Hyp-hle-Trp-Nle] | 801.5 | D |
| 370 | H-Phe-[Orn-Hyp-hle-Trp-Nva] | 787.3 | E |
| 371 | H-Phe-[Orn-Hyp-hle-Trp-Phe] | 835.6 | D |
| 372 | H-Phe-[Orn-NMS-cha-Trp-Nle] | 816.1 | E |
| 373 | H-Phe-[Orn-NMS-hle-Pff-Phe] | 802.7 | E |
| 374 | H-Phe-[Orn-Pro-cha-Pff-Nle] | 790.7 | E |
| 375 | H-Phe-[Orn-Pro-cha-Pff-Phe] | 825.2 | E |
| 376 | H-Phe-[Orn-Pro-cha-Trp-Nle] | 811.5 | E |
| 377 | H-Phe-[Orn-Pro-hle-Mcf-Phe] | 815.3 | D |
| 378 | H-Phe-[Orn-Pro-hle-Ocf-Phe] | 815.3 | E |
| 379 | H-Phe-[Orn-Pro-hle-Pff-Nle] | 765.3 | E |
| 380 | H-Phe-[Orn-Pro-hle-Pff-Phe] | 799.2 | D |
| 381 | H-Phe-[Orn-Pro-hle-Trp-Nle] | 786.1 | D |
| 382 | H-Phe-[Orn-Ser-cha-Trp-Nle] | 802.1 | D |
| 383 | H-Phe-[Orn-Ser-cha-Trp-Phe] [SEQ ID NO: 50] | 835.4 | D |
| 384 | H-Phe-[Orn-Ser-hle-Eaa-Nle] | 805.7 | E |
| 385 | H-Phe-[Orn-Ser-hle-Mcf-Leu] | 771.5 | E |
| 386 | H-Phe-[Orn-Ser-hle-Ocf-Nle] | 771.3 | E |
| 387 | H-Phe-[Orn-Ser-hle-Pff-Leu] | 755.2 | E |
| 388 | H-Phe-[Orn-Ser-hle-Pff-Nle] | 754.8 | D |
| 389 | H-Phe-[Orn-Ser-hle-Pff-Phe] | 788.7 | E |
| 390 | H-Phe-[Orn-Ser-hle-Trp-Nle] | 775.7 | D |
| 392 | Ohf-[Orn-Hyp-hle-Trp-Nle] | 802.4 | E |
| 393 | Tmg-Phe-[Orn-Hyp-cha-Trp-Phe] | 959.9 | E |
| 50 | Ac-Phe-Orn-Pro-cha-Trp-Arg-NH2 [SEQ ID NO: 73] | 913.3 | E |
| 51 | Ac-Phe-Orn-Pro-cha-Trp-Phe-NH2 [SEQ ID NO: 10] | 904.5 | D |
| 52 | Ac-Phe-Orn-Aze-cha-Bta-Phe-NH2 | 907.5 | C |
| 53 | Ac-Phe-Orn-Pro-cha-Bta-2Ni-NH2 | 954.4 | D |
| 54 | Ac-Phe-Orn-Pro-cha-Bta-Cha-NH2 | 910.5 | E |

TABLE 4-continued

Data for antagonistic activity of selected compounds acording to the present invention.

| No. | Compound | (M + H)+ in MS [amu] | activity (group) |
|---|---|---|---|
| 55 | Ac-Phe-Orn-Pip-cha-Trp-Phe-NH2 | 941.3 | D |
| 60 | Ac-Phe-Lys-Ala-Cha-Ala-Leu-ala-Tyr-OH [SEQ ID NO: 74] | 978.9 | F |
| 61 | Ac-Phe-Orn-Pro-cha-Trp-Phe-NH2 [SEQ ID NO: 11] | 904.9 | D |
| 62 | Ac-Phe-Orn-Pro-cha-Bta-Phe-NH2 | 921.8 | D |
| 64 | Ac-Phe-Orn-Pro-cha-Trp-2Ni-NH2 | 954.9 | D |
| 65 | Ac-Phe-Orn-Pro-cha-Trp-Cha-NH2 | 911.1 | E |
| 66 | Ac-Thi-Orn-Aze-cha-Bta-Phe-NH2 | 913.5 | C |
| 67 | Ac-Thi-Orn-Pip-cha-Bta-Phe-NH2 | 941.3 | D |
| 68 | Ac-Phe-Orn-Pro-cha-Trp-Eap-NH2 | 960.9 | F |
| 69 | Me2-Phe-Orn-Pro-cha-Trp-Phe-NH2 [SEQ ID NO: 12] | 890.8 | E |
| 70 | Ph2—CH—CH2—CO-Orn-Pro-cha-Trp-Phe-NH2 | 923.7 | F |
| 71 | Ac-Ebw-Orn-Pro-cha-Trp-Phe-NH2 | 980.8 | F |
| 72 | Ac-Phe-Orn-Pro-cha-Trp-NH—CH2—CH2-Ph | 861.8 | F |
| 73 | Ac-Phe-Orn-Aze-cha-Bta-NH—CH2—CH2-Ph | 864.7 | F |
| 74 | H-Phe-Orn-Pro-cha-Trp-Phe-NH2 [SEQ ID NO: 13] | 862.7 | E |
| 75 | H—Me-Phe-Orn-Pro-cha-Trp-Phe-NH2 [SEQ ID NO: 14] | 876.7 | E |
| 76 | Bu-NH—CO-Phe-Orn-Pro-cha-Trp-Phe-NH2 [SEQ ID NO: 15] | 961.8 | F |
| 77 | Ac-Thi-Orn-Pro-cha-Trp-Phe-NH2 | 910.7 | E |
| 78 | Ac-Ebw-Orn-Pro-cha-Trp-Phe-NH2 | 980.8 | E |
| 79 | Ac-Phe-Orn-Ala-cha-Trp-Phe-NH2 [SEQ ID NO: 16] | 878.7 | E |
| 80 | Ac-Phe-Orn-Pro-cha-Trp-Thi-NH2 | 910.7 | E |
| 81 | Ac-Phe-Orn-Aze-cha-Pcf-Phe-NH2 | 885.7 | F |
| 82 | Ac-Phe-Orn(Ac)-Pro-cha-Trp-Phe-NH2 [SEQ ID NO: 17] | 946.9 | E |
| 83 | Ac-Phe-Orn-Aze-cha-Trp-Phe-NH2 | 890.9 | D |
| 84 | Ac-Phe-Trp-Pro-cha-Trp-Phe-NH2 [SEQ ID NO: 18] | 976.5 | E |
| 85 | Ph—NH—CO-Phe-Orn-Pro-cha-Trp-Phe-NH2 [SEQ ID NO: 19] | 981.7 | E |
| 86 | Bu-O—CO-Phe-Orn-Pro-cha-Trp-Phe-NH2 [SEQ ID NO: 20] | 963.2 | F |
| 87 | Ac-Phe-Lys-Pro-cha-Trp-Phe-NH2 [SEQ ID NO: 21] | 918.4 | E |
| 88 | Ac-Phe-Arg-Pro-cha-Trp-Phe-NH2 [SEQ ID NO: 22] | 946.4 | D |
| 89 | Ac-Phe-Gln-Pro-cha-Trp-Phe-NH2 [SEQ ID NO: 23] | 918.4 | F |
| 90 | Ac-Phe-Ser-Pro-cha-Trp-Phe-NH2 [SEQ ID NO: 51] | 877.3 | F |
| 91 | Ac-Phe-Glu-Pro-cha-Trp-Phe-NH2 [SEQ ID NO: 52] | 919.3 | F |
| 92 | Ac-Phe-Orn-Pip-cha-Trp-Phe-NH2 | 919.8 | E |
| 93 | Ac-Phe-Orn-Hyp-cha-Trp-Phe-NH2 | 920.3 | F |
| 94 | Ac-Phe-Orn-Pro-cha-Trp-1Ni-NH2 | 934.5 | D |
| 95 | Ac-Phe-Orn-Aze-cha-Bta-Phe-NH—Me | 921.6 | F |
| 96 | CH3—SO2-Phe-Orn-Aze-cha-Bta-Phe-NH2 | 943.9 | D |
| 99 | Ac-Phe-Orn-Aze-cha-Pff-Phe-NH2 | 869.7 | E |
| 100 | Ac-Phe-Orn-Aze-cha-Mcf-Phe-NH2 | 885.7 | E |
| 101 | Ac-Phe-Orn(Ac)-Aze-cha-Bta-Phe-NH2 | 921.7 | D |
| 102 | Ac-Ebw-Orn-Pro-cha-Trp-Phe-NH2 | 980.8 | E |
| 103 | Ac-Phe-Trp-Pro-cha-Trp-Phe-NH2 [SEQ ID NO: 24] | 876.5 | E |
| 104 | Ac-Phe-Arg-Pro-cha-Trp-Phe-NH2 [SEQ ID NO: 25] | 946.4 | E |
| 105 | Ac-Phe-Orn-Pip-cha-Trp-Phe-NH2 | 919.8 | E |
| 106 | 3PP-Orn-Aze-cha-Bta-Phe-NH2 | 850.8 | E |
| 107 | Ac-Phe-Orn-Tic-cha-Trp-Phe-NH2 | 966.3 | E |
| 108 | Ac-Phe-Orn-Ser-cha-Trp-Phe-NH2 [SEQ ID NO: 26] | 894.5 | D |
| 109 | Ac-Phe-Orn-Pro-chg-Trp-Phe-NH2 [SEQ ID NO: 27] | 890.4 | E |
| 110 | Ac-Phe-Orn-Pro-hch-Trp-Phe-NH2 [SEQ ID NO: 28] | 918.5 | D |
| 111 | Ac-Phe-Orn-Pro-cha-Trp-Phg-NH2 | 890.4 | F |
| 112 | Ac-Phe-Bta-Aze-cha-Bta-Phe-NH2 | 996.6 | D |
| 113 | Ac-Phe-Trp-Pro-cha-Bta-Phe-NH2 | 993.7 | E |

TABLE 4-continued

Data for antagonistic activity of selected compounds acording to the present invention.

| No. | Compound | (M + H)+ in MS [amu] | activity (group) |
|---|---|---|---|
|  | [SEQ ID NO: 29] | | |
| 115 | Ac-Phe-Orn-Pip-cha-Trp-Phe-OH | 919.4 | F |
| 116 | Ac-Phe-Orn-Tic-cha-Trp-Phe-OH | 967.7 | F |
| 117 | Ac-Phe-Orn-Ser-cha-Trp-Phe-OH | 895.7 | F |
|  | [SEQ ID NO: 30] | | |
| 118 | Ac-Phe-Orn-Pro-chg-Trp-Phe-OH | 891.8 | F |
|  | [SEQ ID NO: 31] | | |
| 119 | Ac-Phe-Eec-Pro-cha-Bta-Phe-NH2 | 1041.7 | E |
| 120 | Ac-Phe-Nle-Pro-cha-Bta-Phe-NH2 | 920.5 | E |
| 121 | Ac-Phe-Har-Pro-cha-Bta-Phe-NH2 | 978.0 | D |
| 122 | Ac-Phe-Arg-Pro-cha-Bta-Phe-NH2 | 964.0 | D |
|  | [SEQ ID NO: 32] | | |
| 123 | Ac-Phe-Cys(Acm)-Pro-cha-Bta-Phe-NH2 | 981.5 | F |
|  | [SEQ ID NO: 33] | | |
| 124 | Ac-Phe-Mpa-Pro-cha-Bta-Phe-NH2 | 955.7 | E |
| 125 | Ac-Eby-Orn-Pro-cha-Bta-Phe-NH2 | 921.7 | D |
| 126 | Ac-Phg-Orn-Pro-cha-Bta-Phe-NH2 | 907.8 | E |
| 127 | Ac-Phe-Paf-Pro-cha-Bta-Phe-NH2 | 969.6 | F |
| 128 | H2N—CO-Phe-Orn-Pro-cha-Bta-Phe-NH2 | 922.8 | D |
| 129 | Me—O—CO-Phe-Orn-Pro-cha-Bta-Phe-NH2 | 937.8 | E |
| 130 | (—CO—CH2—NH—CO—)-Phe-Orn-Pro-cha-Bta-Phe-NH2 | 962.9 | E |
| 132 | Ac-Phe-Orn-Pro-hch-Trp-Phe-OH | 919.8 | E |
|  | [SEQ ID NO: 34] | | |
| 133 | (—CO—CH2—CH2—CO—)-Phe-Orn-Pro-cha-Bta-Phe-NH2 | 961.9 | F |
| 134 | tBu-CO-Phe-Orn-Pro-cha-Bta-Phe-NH2 | 963.9 | E |
| 135 | Ac-Lys-Phe-Orn-Aze-cha-Bta-Phe-NH2 | 1036.0 | C |
| 136 | Ac-Gly-Phe-Orn-Aze-cha-Bta-Phe-NH2 | 965.0 | D |
| 137 | Ac-Arg-Phe-Orn-Aze-cha-Bta-Phe-NH2 | 1064.1 | D |
| 138 | Ac-His-Phe-Orn-Aze-cha-Bta-Phe-NH2 | 1045.0 | E |
| 139 | Ac-Ser-Phe-Orn-Aze-cha-Bta-Phe-NH2 | 995.0 | E |
| 140 | Ac-Guf-Phe-Orn-Aze-cha-Bta-Phe-NH2 | 1112.1 | E |
| 141 | Ac-Dab-Phe-Orn-Aze-cha-Bta-Phe-NH2 | 1008.0 | E |
| 142 | FH2C—CO-Phe-Orn-Pro-cha-Bta-Phe-NH2 | 939.8 | D |
| 143 | Ac-Phe-Orn(Et2)-Pro-cha-Trp-Phe-NH2 | 960.9 | E |
|  | [SEQ ID NO: 35] | | |
| 148 | Ac-Phe-N(nBu)-CH2—CO-Pro-cha-Trp-Phe-NH2 | 920.8 | F |
|  | [SEQ ID NO: 53] | | |
| 149 | Ac-Phe-Orn-Pro-hle-Bta-Phe-NH2 | 895.4 | C |
| 150 | Ac-Phe-Arg(CH2—CH2)-Pro-cha-Bta-Phe-NH2 | 990.1 | B |
|  | [SEQ ID NO: 37] | | |
| 151 | Ac-Ala-Phe-Orn-Aze-cha-Bta-Phe-NH2 | 978.8 | D |
| 152 | Ac-Arg-Phe-Orn-Aze-cha-Bta-Phe-NH2 | 1063.8 | D |
| 153 | Ac-Cit-Phe-Orn-Aze-cha-Bta-Phe-NH2 | 1064.7 | D |
| 154 | Ac-Gly-Phe-Orn-Aze-cha-Bta-Phe-NH2 | 964.7 | C |
| 155 | Ac-Gly-Phe-Orn-Aze-chg-Bta-Phe-NH2 | 950-3 | E |
| 156 | Ac-Gly-Phe-Orn-Aze-hch-Bta-Phe-NH2 | 978.3 | E |
| 157 | Ac-Gly-Thi-Orn-Aze-cha-Bta-Phe-NH2 | 971 | D |
| 158 | Ac-His-Phe-Orn-Aze-cha-Bta-Phe-NH2 | 1044.3 | E |
| 159 | Ac-Hyp-Phe-Orn-Aze-cha-Bta-Phe-NH2 | 1020.7 | D |
| 160 | Ac-Lys-Phe-Orn-Aze-cha-Bta-Phe-NH2 | 1035.8 | D |
| 161 | Ac-Mff-Orn-Pro-cha-Bta-Phe-NH2 | 939.5 | E |
| 162 | Ac-Mff-Orn-Pro-hle-Bta-Phe-NH2 | 913.4 | E |
| 163 | Ac-Mff-Orn-Pro-hle-Mcf-Mff-NH2 | 909.9 | E |
| 164 | Ac-Mmy-Orn-Pro-hle-Pff-Phe-NH2 | 888 | E |
| 165 | Ac-NMF-Orn-Pro-cha-Bta-Phe-NH2 | 935.5 | E |
| 166 | Ac-Off-Orn-Pro-cha-Bta-Phe-NH2 | 940 | D |
| 167 | Ac-Off-Orn-Pro-hle-Bta-Phe-NH2 | 913.4 | D |
| 168 | Ac-Orn-Phe-Orn-Aze-cha-Bta-Phe-NH2 | 1043.8 | E |
| 169 | Ac-Pff-Orn-Pro-cha-Bta-Phe-NH2 | 940 | D |
| 170 | Ac-Pff-Orn-Pro-hle-Bta-Phe-NH2 | 913.4 | E |
| 171 | Ac-Pff-Orn-Pro-hle-Mcf-Pff-NH2 | 909.6 | E |
| 206 | Ac-Phe-Ala-Pro-cha-Bta-Phe-NH2 | 878.5 | E |
|  | [SEQ ID NO: 41] | | |
| 207 | Ac-Phe-Arg-Pro-hle-Bta-Phe-NH2 | 937.7 | E |
|  | [SEQ ID NO: 42] | | |
| 208 | Ac-Phe-Arg-Pro-hle-Mcf-Phe-NH2 | 915.9 | E |
|  | [SEQ ID NO: 43] | | |
| 209 | Ac-Phe-Cit-Hyp-hle-Bta-Phe-NH2 | 954.7 | E |
| 210 | Ac-Phe-Cit-Pro-cha-Bta-Phe-NH2 | 964.7 | E |
| 211 | Ac-Phe-Cit-Pro-hle-Bta-Phe-NH2 | 939 | D |
| 212 | Ac-Phe-Cit-Ser-hle-Bta-Phe-NH2 | 928.7 | E |
| 213 | Ac-Phe-Dab-Aze-cha-Bta-Phe-NH2 | 894 | D |
| 214 | Ac-Phe-Dab-Aze-hle-Bta-Phe-NH2 | 868.1 | D |

TABLE 4-continued

Data for antagonistic activity of selected compounds acording to the present invention.

| No. | Compound | (M + H)+ in MS [amu] | activity (group) |
|---|---|---|---|
| 215 | Ac-Phe-Dab-Pro-cha-Bta-Phe-NH2 | 907.9 | C |
| 216 | Ac-Phe-Dap-Pro-cha-Bta-Phe-NH2 | 893.7 | E |
| 217 | Ac-Phe-Ech-Pro-cha-Bta-Phe-NH2 | 1033.7 | E |
| 218 | Ac-Phe-Eep-Pro-cha-Bta-Phe-NH2 | 1013.5 | E |
| 219 | Ac-Phe-Fcn-Aze-cha-Bta-Phe-NH2 | 961.9 | C |
| 220 | Ac-Phe-Fcn-Pro-cha-Bta-Phe-NH2 | 975.9 | C |
| 221 | Ac-Phe-Fco-Pro-cha-Bta-Phe-NH2 | 935.8 | D |
| 222 | Ac-Phe-Fco-Pro-cha-Bta-Phe-NH2 | 962 | E |
| 223 | Ac-Phe-Fcp-Aze-cha-Bta-Phe-NH2 | 1444 | D |
| 224 | Ac-Phe-Ffa-Aze-cha-Bta-Phe-NH2 | 976 | D |
| 225 | Ac-Phe-Ffa-Pro-cha-Bta-Phe-NH2 | 990 | D |
| 226 | Ac-Phe-Ffa-Pro-hle-Bta-Phe-NH2 | 964 | C |
| 227 | Ac-Phe-G23-Pro-cha-Bta-Phe-NH2 | 1000.3 | E |
| 228 | Ac-Phe-Guf-Pro-cha-Bta-Phe-NH2 | 1011.9 | D |
| 229 | Ac-Phe-Har-Aze-cha-Bta-Phe-NH2 | 964.1 | C |
| 230 | Ac-Phe-His-Pro-cha-Bta-Phe-NH2 [SEQ ID NO: 44] | 944.3 | E |
| 231 | Ac-Phe-L22-Pro-cha-Bta-Phe-NH2 | 949.8 | C |
| 232 | Ac-Phe-OrA-Pro-cha-Bta-Phe-NH2 | 963.6 | E |
| 233 | Ac-Phe-OrE-Pro-cha-Bta-Phe-NH2 | 977.8 | E |
| 234 | Ac-Phe-Orn-Aze-hle-Bta-Phe-NH2 | 881.9 | D |
| 235 | Ac-Phe-Orn-Chy-cha-Bta-Phe-NH2 | 937.4 | E |
| 236 | Ac-Phe-Orn-Chy-hle-Pff-Phe-NH2 | 873.8 | E |
| 237 | Ac-Phe-Orn-G24-cha-Bta-Phe-NH2 | 923.8 | E |
| 238 | Ac-Phe-Orn-G25-cha-Bta-Phe-NH2 | 939.8 | E |
| 239 | Ac-Phe-Orn-G26-cha-Bta-Phe-NH2 | 961.8 | E |
| 240 | Ac-Phe-Orn-G27-cha-Bta-Phe-NH2 | 972.7 | E |
| 241 | Ac-Phe-Orn-G30-cha-Bta-Phe-NH2 | 1006.8 | E |
| 242 | Ac-Phe-Orn-G31-cha-Bta-Phe-NH2 | 1045.9 | E |
| 243 | Ac-Phe-Orn-Hse-cha-Bta-Phe-NH2 | 925.9 | E |
| 244 | Ac-Phe-Orn-Hyp-hle-Bta-Phe-NH2 | 911.7 | E |
| 245 | Ac-Phe-Orn-Hyp-hle-Pff-Phe-NH2 | 874 | E |
| 246 | Ac-Phe-Orn-NMA-cha-Bta-Phe-NH2 | 909.8 | E |
| 247 | Ac-Phe-Orn-NMS-cha-Bta-Phe-NH2 | 925.8 | E |
| 248 | Ac-Phe-Orn-Pro-cha-1Ni-Phe-NH2 | 916 | E |
| 249 | Ac-Phe-Orn-Pro-cha-Bta-1Ni-NH2 | 971.9 | E |
| 250 | Ac-Phe-Orn-Pro-cha-Bta-Bhf-NH2 | 935.9 | D |
| 251 | Ac-Phe-Orn-Pro-cha-Bta-Dff-NH2 | 957.7 | D |
| 252 | Ac-Phe-Orn-Pro-cha-Bta-Eaa-NH2 | 933.9 | E |
| 253 | Ac-Phe-Orn-Pro-cha-Bta-L19 | 979.1 | E |
| 254 | Ac-Phe-Orn-Pro-cha-Bta-Mcf-NH2 | 955.9 | E |
| 255 | Ac-Phe-Orn-Pro-cha-Bta-Mff-NH2 | 939.8 | C |
| 256 | Ac-Phe-Orn-Pro-cha-Bta-NH—CH(CH2OH)—CH2-Ph | 964.6 | E |
| 257 | Ac-Phe-Orn-Pro-Cha-Bta-NH-NBn-CO—NH2 | 922.8 | E |
| 258 | Ac-Phe-Orn-Pro-cha-Bta-Opa-NH2 | 922.9 | E |
| 259 | Ac-Phe-Orn-Pro-cha-Bta-Pcf-NH2 | 956.1 | D |
| 260 | Ac-Phe-Orn-Pro-cha-Bta-Pmf-NH2 | 935.8 | D |
| 261 | Ac-Phe-Orn-Pro-cha-Bta-Thi-NH2 | 927.8 | C |
| 262 | Ac-Phe-Orn-Pro-cha-Otf-Phe-NH2 | 933.9 | E |
| 263 | Ac-Phe-Orn-Pro-ctb-Bta-Phe-NH2 | 927.4 | D |
| 264 | Ac-Phe-Orn-Pro-ctb-Eaa-Phe-NH2 | 940.2 | D |
| 265 | Ac-Phe-Orn-Pro-ctb-Mcf-Phe-NH2 | 906.3 | E |
| 266 | Ac-Phe-Orn-Pro-ctb-Pff-Phe-NH2 | 890.1 | D |
| 267 | Ac-Phe-Orn-Pro-hch-Trp-Phe-OH [SEQ ID NO: 45] | 919.8 | E |
| 268 | Ac-Phe-Orn-Pro-hle-1Ni-Phe-NH2 | 889.7 | D |
| 269 | Ac-Phe-Orn-Pro-hle-6FW-Phe-NH2 | 897 | E |
| 270 | Ac-Phe-Orn-Pro-hle-Bta-1Ni-NH2 | 945.8 | E |
| 271 | Ac-Phe-Orn-Pro-hle-Bta-2Ni-NH2 | 946 | E |
| 272 | Ac-Phe-Orn-Pro-hle-Bta-5Ff-NH2 | 985.7 | E |
| 273 | Ac-Phe-Orn-Pro-hle-Bta-Aic-NH2 | 908 | E |
| 274 | Ac-Phe-Orn-Pro-hle-Bta-Cha-NH2 | 902 | E |
| 275 | Ac-Phe-Orn-Pro-hle-Bta-Chg-NH2 | 888 | E |
| 276 | Ac-Phe-Orn-Pro-hle-Bta-Eaa-NH2 | 964.4 | E |
| 277 | Ac-Phe-Orn-Pro-hle-Bta-Egy-NH2 | 964.4 | E |
| 278 | Ac-Phe-Orn-Pro-hle-Bta-Pcf-NH2 | 930.2 | E |
| 279 | Ac-Phe-Orn-Pro-hle-Bta-Pff-NH2 | 913.7 | E |

TABLE 4-continued

Data for antagonistic activity of selected compounds acording to the present invention.

| No. | Compound | (M + H)+ in MS [amu] | activity (group) |
|---|---|---|---|
| 280 | Ac-Phe-Orn-Pro-hle-Bta-Phe-NH2 | 895.8 | D |
| 281 | Ac-Phe-Orn-Pro-hle-Bta-phe-OH | 897 | E |
| 282 | Ac-Phe-Orn-Pro-hle-Bta-Tyr-NH2 | 911.5 | E |
| 283 | Ac-Phe-Orn-Pro-hle-Dff-Phe-NH2 | 875.4 | E |
| 284 | Ac-Phe-Orn-Pro-hle-Eaa-Phe-NH2 | 907.4 | E |
| 285 | Ac-Phe-Orn-Pro-hle-Egc-Phe-NH2 | 892.8 | E |
| 286 | Ac-Phe-Orn-Pro-hle-Egy-Phe-NH2 | 908.3 | E |
| 287 | Ac-Phe-Orn-Pro-hle-Egz-Phe-NH2 | 885 | E |
| 288 | Ac-Phe-Orn-Pro-hle-Mcf-2Ni-NH2 | 924.3 | E |
| 289 | Ac-Phe-Orn-Pro-hle-Mcf-Cha-NH2 | 880.3 | D |
| 290 | Ac-Phe-Orn-Pro-hle-Mcf-Pff-NH2 | 892.1 | E |
| 291 | Ac-Phe-Orn-Pro-hle-Mcf-Phe-NH2 | 874.2 | E |
| 292 | Ac-Phe-Orn-Pro-hle-Mff-Phe-NH2 | 857.9 | E |
| 293 | Ac-Phe-Orn-Pro-hle-Mmy-Phe-NH2 | 870.1 | E |
| 294 | Ac-Phe-Orn-Pro-hle-Ocf-Phe-NH2 | 874.1 | E |
| 295 | Ac-Phe-Orn-Pro-hle-Off-Phe-NH2 | 857.9 | E |
| 296 | Ac-Phe-Orn-Pro-hle-Otf-Phe-NH2 | 907.8 | E |
| 297 | Ac-Phe-Orn-Pro-hle-Pff-2Ni-NH2 | 908.1 | E |
| 298 | Ac-Phe-Orn-Pro-hle-Pff-Cha-NH2 | 864 | E |
| 299 | Ac-Phe-Orn-Pro-hle-Pff-Eaa-NH2 | 926.3 | E |
| 300 | Ac-Phe-Orn-Pro-hle-Pff-Mmy-NH2 | 888.1 | E |
| 301 | Ac-Phe-Orn-Pro-hle-Pff-Pff-NH2 | 876 | E |
| 302 | Ac-Phe-Orn-Pro-hle-Pff-Phe-NH2 | 857.7 | E |
| 304 | Ac-Phe-Orn-Pro-hle-Phe-Phe-NH2 [SEQ ID NO: 46] | 839.7 | E |
| 305 | Ac-Phe-Orn-Pro-hle-Tff-Phe-NH2 | 893.8 | E |
| 306 | Ac-Phe-Orn-Pro-hle-Trp-Phe-NH2 [SEQ ID NO: 47] | 878.9 | E |
| 307 | Ac-Phe-Orn-Pro-ile-Trp-Phe-NH2 [SEQ ID NO: 48] | 864.5 | B |
| 308 | Ac-Phe-Orn-Pro-omf-Bta-Phe-NH2 | 929.8 | E |
| 309 | Ac-Phe-Orn-Ser-cha-Bta-Phe-NH2 | 912 | D |
| 310 | Ac-Ser-Phe-Orn-Aze-cha-Bta-Phe-NH2 | 994.7 | C |
| 312 | Ac-Thi-Orn-Pro-cha-Bta-Phe-NH2 | 927.8 | D |
| 313 | Ac-Thi-Orn-Pro-cha-Bta-Thi-NH2 | 933.8 | D |
| 314 | Ac-Thr-Phe-Orn-Aze-cha-Bta-Phe-NH2 | 1008.7 | D |
| 316 | CH3CH2CO-Phe-Orn-Pro-cha-Bta-Phe-NH2 | 935.9 | D |
| 320 | FAc-Phe-Fib-Aze-cha-Bta-Phe-NH2 | 1023.9 | E |
| 321 | FAc-Phe-Orn-Aze-cha-Bta-Phe-NH2 | 925.7 | D |
| 322 | FAc-Phe-Orn-Pro-cha-Bta-Phe-NH2 | 939.8 | D |
| 324 | Faz-Orn-Pro-cha-Bta-Phe-NH2 | 864.7 | E |
| 329 | Fbn-Phe-Cit-Pro-hle-Bta-Phe-NH2 | 1001.9 | E |
| 339 | Fhu-Phe-Orn-Pro-cha-Bta-Phe-NH2 | 921.8 | E |
| 340 | Fid-Phe-Orn-Pro-cha-Bta-Phe-NH2 | 966.6 | E |
| 345 | H-Gly-Phe-Orn-Pro-cha-Bta-Phe-NH2 [SEQ ID NO: 49] | 936.7 | E |
| 346 | H-Nip-Phe-Cit-Pro-hle-Bta-Phe-NH2 | 1007.7 | E |
| 348 | Hoo-Phe-Cit-Pro-hle-Pff-Phe-NH2 | 999 | E |
| 349 | Hoo-Phe-Orn-Hyp-hle-Pff-Phe-NH2 | 971.8 | E |
| 350 | Hoo-Phe-Orn-Pro-hle-Bta-Phe-NH2 | 994.2 | D |
| 351 | Hoo-Phe-Orn-Pro-hle-Mcf-Phe-NH2 | 972.3 | D |
| 352 | Hoo-Phe-Orn-Pro-hle-Pff-Phe-NH2 | 956 | D |
| 391 | H-Phe-Cit-Pro-hle-Bta-Phe-NH2 | 896.7 | E |

Example 12

Determination of $EC_{50}$ Values in an Enzyme Release Assay

The determination of the $EC_{50}$ value was performed in a way similar to the procedure described in example 11, with the only exception that 30 µl of the compound to be tested were mixed with 75 µl of the cell suspension described in example 11. There was no preincubation or addition of C5a for stimulation of the enzyme release. The results for the tested compounds are shown in table 5.

TABLE 5

Data for agonistic activity of selected compounds according to the present invention

| No. | Compound | $EC_{50}$ (nM) |
|---|---|---|
| — | hrC5a | 2,4 |
| 3 | HOCH2(CHOH)4—C=N—O—CH2—CO—Phe[OP-dCha-W-Nle] | >>1430 |
| 41 | Ph—CH2—CH2—CO-[Orn-Pro-cha-Trp-Nle] | >>1430 |
| 2 | Ac-Phe-[Orn-Hyp-cha-Trp-Phe] | >>1430 |
| 42 | H-Phe-[Orn-Pro-cha-Trp-Nle] | >>1430 |
| 1 | Ac-Phe-[Orn-Pro-cha-Trp-Phe] | >>1430 |

TABLE 5-continued

Data for agonistic activity of selected compounds according to the present invention

| No. | Compound | $EC_{50}$ (nM) |
|---|---|---|
| 43 | Ac-Lys-Phe-[OP-dCha-W-Nle] | >>1430 |
| 28 | H-Phe-[Orn-Pro-cha-Trp-Nle] | >>1430 |
| 44 | H-Phe-[Orn-Ser-cha-Trp-Nle] | >>1430 |
| 33 | Ac-Phe-[Orn-Pro-cha-Trp-Eaf] | >>1430 |
| 61 | Ac-Phe-Orn-Pro-cha-Trp-Phe-NH$_2$ [SEQ ID NO: 11] | >100000 |
| 62 | Ac-Phe-Orn-Pro-cha-Bta-Phe-NH$_2$ | >100000 |
| 71 | Ac-Ebw-Orn-Pro-cha-Trp-Phe-NH$_2$ | >100000 |
| 88 | Ac-Phe-Arg-Pro-cha-Trp-Phe-NH$_2$ [SEQ ID NO: 22] | >100000 |
| 55 | Ac-Phe-Orn-Pip-cha-Trp-Phe-NH$_2$ | >100000 |
| 83 | Ac-Phe-Orn-Aze-cha-Trp-Phe-NH$_2$ | >100000 |
| 84 | Ac-Phe-Trp-Pro-cha-Trp-Phe-NH$_2$ [SEQ ID NO: 18] | >100000 |
| 67 | Ac-Thi-Orn-Pip-cha-Bta-Phe-NH$_2$ | >100000 |

Example 13

Solubility Determination for Selected C5aR-Antagonists

Solubility of compounds was determined by the following procedure: 20 µl of a 10 mM stock solution (in DMSO) of the compound were diluted in 980 µl of the solvent to be tested. After incubation for 24 h at RT under shaking the samples are centrifuged at 11.000 rpm in an Eppendorf centrifuge. The supernatant is determined by photometry. The opiteal density of the sample and of a control in 60% MeOH served as a measure for the solubility. Compounds that showed a similarly good solubility in the solvent to be tested as in the control were tested for their maximum solubility as follows. Therefor the compound was suspended at 10 mg/ml in the solvent systems of choice. The undissolved part was removed by centrifugation after 24 h. The UV-absorption of the supernatant was measured and compared to a respective reference value 60% MeOH). The solubility of some of the compounds according to the invention is shown in table 6.

TABLE 6

Solubility of some representatives of the compounds according to the invention

| No. | Compound | Solubility in 20 mM HEPES pH 7.4 (% of 200 µM) |
|---|---|---|
| 1 | Ac-Phe-[Orn-Pro-cha-Trp-Phe] [SEQ ID NO: 7] | 8 |
| 2 | Ac-Phe-[Orn-Hyp-cha-Trp-Phe] | 13 |
| 28 | Ac-Phe-[Orn-Pro-cha-Trp-Nle] | 22 |
| 42 | H-Phe-[Orn-Pro-cha-Trp-Phe] [SEQ ID NO: 75] | 45 |
| 4 | X-Phe-[Orn-Pro-cha-Trp-Nle]; X = 2-Acetamido-1-Methyl-Glucuronyl | 84 |
| 40 | Ac-Phe-[Orn-Pro-cha-Trp-Arg] [SEQ ID NO: 68] | 94 |
| 43 | Ac-Lys-Phe-[Orn-Pro-cha-Trp-Nle] [SEQ ID NO: 9] | 93 |

Example 14

Development of a Pharmacophor Model Underlying the Antagonists

The exchange of arginine in compound 40 by alanine (39) outlines the importance of the side-chain in this position for the inhibitory activity if the peptide. The replacement of arginine by the positively charged amino acid lysine (22) surprisingly results in an increase of the $IC_{50}$ value (from 20 nM to 8700 nM). This means that the positive charge alone is not responsible for the antagonistic activity. The introduction of 4-aminophenylalanine (Paf) 14 to the C-terminal position results in an $IC_{50}$-value of 30 nM. The amino-group in Paf has a similar distance to the Cα-atom compared to the amino group in lysine. The exchange of arginine in compound 40 with the uncharged and very hydrophobic phenylalanine results in compound 1, which surprisingly shows an $IC_{50}$-value (23 nM) comparable to the one of compound 40. This clearly shows that, surprisingly, not the positively charged side chain of Arg and Paf, respectively, is responsible for the critical interaction with C5aR, but the hydrophobic part of Paf, Phe and the aliphatic side chain of arginine, respectively. It is possible to replace the arginine by other, hydrophobic substitutions without a significant increase of the $IC_{50}$-value compared to compound 40. Examples for these types of substitutions are shown, among others, in compounds 1, 28, 29, 31, 32, 33, 34, 35, 36, 37, 38.

The exchange of further amino acids in 40 by Ala, N-Me-Ala, or d-Ala revealed that the side chains of the following amino acids are important for antagonistic activity: Phe, cha, Trp.

A pharmacophor model was developed based on the structure-activity relationship of these and additional peptides. The distances for the important residues (two hydrophobic and two aromatic groups) for activity are predicted by the following method:

The pharmacophor model was developed based on a 2 ns lasting molecular dynamic simulation (increment of 2 fs) of compound 28. The simulation was performed using AMBER94-force field and an explicit Water-model (TIP3) under periodic frame work. The static analysis of the snapshots from the last nanosecond of the trajectory (1000 structures) gave the distances between the mass-centered pharmacophor groups (see below).

The starting structure for the molecular dynamic simulation was based on ensemble-dynamic calculations with seven cyclic peptides. The peptides were highly active ($IC_{50}$ in the lower nanomolar range) and with structure-restricting properties when compared to each other.

Example 15

Measurement of the AB-Permeability in a TC-7 based Assay-system

The compounds to be tested are diluted to a concentration of 50 µM in HBSS-MES (5 mM, pH 6.5) from 10 mM stock solution in 100% DMSO. $^{14}$C-mannitol (approx. 4 µM) is added to the sample. Subsequently, the solution is centrifuged and the supernatant is added to the apical side of a TC-7 cell culture (passage 15, in a 24 well transwell plate) to a final DMSO-concentration of 1%. HBSS-HEPES (5 mM, pH 7.4) is placed at the basolateral side. Subsequently, the cells were incubated for 120 min at 37° C. The integrity of the TC-7 cell-layer was tested by the added mannitol (Papp <2.5 10$^{-6}$ cm/s). The permeability Papp [cm/s] is derived from the equation $(V_R \times C_{R120})/(\Delta t \times A \times (C_{D,mid} - C_{R,mid}))$, whereby $V_R$ is the volume of the receiver chamber, $C_{R120}$ is the concentration of the test compound in the receiver camber after 120 min, $\Delta t$ is the incubation time, A is the area of the TC-7 cell-layer, $C_{D,mid}$ is the midpoint concentration of the test compound in the donor chamber and $C_{R,mid}$ is the concentration of the test compound in the receiver chamber.

| Compound | AB-permeability [cm/s] |
|---|---|
| Ac-Phe[Orn-Pro-cha-Trp-Arg] [SEQ ID NO: 6] | 0.52 |
| Ac-Phe[Orn-Hyp-cha-Trp-Phe] | 14.25 |

Example 16

Synthesis of Ac-Phe-Orn-Pro-cha-Trp-Phe-NH$_2$ (51) [SEQ ID NO: 10]

The peptide was prepared by linear peptide synthesis in accordance with AAV 1. Subsequent, purification by HPLC yielded 10.0 mg of the desired product 51 as a white solid.
MS (ESI): m/z=904.5 [(M+H)$^+$].

Example 17

Synthesis of Ac-Phe-Orn-Aze-cha-Bta-Phe-NH$_2$ (52)

The linear peptide was prepared by linear peptide synthesis in accordance with AAV 1 and purified by HPLC. 10.5 mg of compound 52 were obtained as a white solid.
MS (ESI): m/z=907.5 [(M+H)$^+$].

Example 18

Synthesis von Ac-Phe-Orn-Pro-cha-Trp-NH—CH$_2$—CH$_2$-Ph (72)

200 mg Bromo-(4-methoxyphenyl)methyl polystyrene resin is incubated with 5 ml of a 50% solution of phenylethylamine in THF (v/v) at RT for 18 h. Subsequently, the resin is washed (DMF; 3×5.0 ml, MeOH; 3×5.0 ml, DCM; 3×5.0 ml) and the peptide is synthesized in accordance with AAV 1. After purification by HPLC 4.1 mg of compound 72 were obtained as a white solid.
MS (ESI): m/z=861.8 [(M+H)$^+$].

Example 19

Synthesis of Ac-Phe-Orn-Aze-cha-Bta-Phe-NH-Me (95)

4.5 g 4-(4-formyl-3-methoxy-phenoxy)-butyl-acid-polystyrene resin was swollen for 15 min in THF. The resin was filtered off and reacted with a mixture of 3.04 g (10 eq.) methylamine-hydrochloride, 2.7 ml acetic acid, 2.7 ml trimethylorthoformiate and 90 ml THF. After one hour of stirring 2.83 g (10 eq.) sodium cyanoborhydride and 45 ml DMF were added. The mixture was stirred over night at room temperature, the resin was filtered off and washed with DMF (5×), MeOH (5×) und CH$_2$Cl$_2$ (5×). Subsequently, an amino acid coupling was performed using 968 mg (5 eq.) Fmoc-Phe-OH, 950 mg (5 eq.) HATU and 3.75 ml DIPEA in 10 ml DMF for two hours. The resin was filtered off and washed with DMF (5×), MeOH (5×) und CH$_2$Cl$_2$ (5×). 200 mg of the obtained resin was further used for linear peptide synthesis in accordance with AAV 1. Subsequent purification by HPLC yielded 10.0 mg of the desired product 95 as a white solid.
MS (ESI): m/z=921.6 [(M+H)$^+$].

Example 20

Synthesis of CH$_3$—SO$_2$-Phe-Orn-Aze-cha-Bta-Phe-NH$_2$ (96)

The peptide was prepared by linear peptide synthesis in accordance with AAV 1, whereby CH$_3$—SO$_2$—Cl was used instead of a N-terminal amino acid. Subsequent purification by HPLC yielded 5.5 mg of the desired product 96 as a white solid.
MS (ESI): m/z=943.9 [(M+H)$^+$].

Example 21

Synthesis of H$_2$N-CO-Phe-Orn-Pro-cha-Bta-Phe-NH$_2$ (128)

The resin-bound peptide H-Phe-Orn-Pro-cha-Bta-Phe-Rink-amide resin was prepared in accordance with AAV 1. Subsequently, diphenylmethylisocyanate (5 eq.) and DIPEA (10 eq.) in DMF were added and agitated for two hours. After cleavage from the resin with a mixture of 95% TFA, 2.5% water and 2.5% TIPS a purification by HPLC was performed. 0.92 mg of the compound was obtained as a white solid.
MS (ESI): m/z=922.8 [(M+H)$^+$].

Example 22

Synthesis of (—CO—CH$_2$—NH—CO—)-Phe-Orn-Pro-cha-Bta-Phe-NH$_2$ (130)

The resin-bound peptide H-Gly-Phe-Orn-Pro-cha-Bta-Phe-Rink-amide resin [SEQ ID NO: 76] was synthesized in accordance with AAV 1. Subsequently, the peptide was incubated for three hours with disuccinimidylcarbonate (3 eq.) and DIPEA (3 eq.) in DMF was added and agitated for 3 hours. Subsequently, additional 3 eq. DIPEA were added and the reaction was agitated for another five hours at room temperature. After cleavage from the resin with a mixture of 95% TFA, 2.5% water, and 2.5% TIPS, purification was performed by HPLC. 3.8 mg of the compound were obtained as a white solid.
MS (ESI): m/z=962.9 [(M+H)$^+$].

Example 23

Synthesis of (—CO—CH$_2$—CH$_2$—CO—)-Phe-Orn-Pro-cha-Bta-Phe-NH$_2$ (133)

The resin-bound peptide H-Phe-Orn-Pro-cha-Bta-Phe-Rink-amide resin was synthesized in accordance with AAV 1. Subsequently, succinic anhydride (5 eq.) and DIPEA (10 eq.) in DMF were added and the reaction agitated for two hours. The resin was filtered off and washed with DMF (5×), MeOH (5×), and CH$_2$Cl$_2$ (5×). Subsequently, the resin was incubated with HBTU (5 eq.) and DIPEA (10 eq.) in DMF for one day. The peptide was cleaved from the resin with a mixture of 95% TFA, 2.5% water and 2.5% TIPS and purified by HPLC, whereby 0.47 mg of the compound were obtained as a white solid.
MS (ESI): m/z=961.9 [(M+H)$^+$].

Example 24

Synthesis of FH$_2$C—CO-Phe-Orn-Pro-cha-Bta-Phe-NH$_2$ (142)

0.9 mg of the desired product 142 were obtained as a white solid after linear peptide synthesis in accordance with AAV 1, whereby fluoro-acetic acid was used rather than a N-terminal amino acid, and subsequent purification by HPLC.
MS (ESI): m/z=939.8 [(M+H)$^+$].

Example 25

Synthesis of Ac-Phe-Orn(Et$_2$)-Pro-cha-Trp-Phe-NH$_2$ (143) [SEQ ID NO: 35]

10.0 mg of compound 51 were obtained after linear peptide synthesis in accordance with AAV 1 and subsequent purification by HPLC. 5.0 mg of this compound were dissolved in THF and 1 ml acetaldehyde was added. The suspension was slowly stirred for 12 h at RT after addition of 100 mg (polystyrene methyl)trimethyl-ammoniumcyanoborhydride (3 mmol/g). Subsequently, the resin was filtered off and the mixture was evaporated to dryness. After purification by HPLC 1.2 mg of the desired compound 143 were obtained.
MS (ESI): m/z=960.9 [(M+H)$^+$].

Example 26

Synthesis of Ac-Phe-N($^n$Bu)-CH$_2$—CO-Pro-cha-Trp-Phe-NH$_2$ (144)

The synthesis of the peptide H-Pro-cha-Trp-Phe-Rink-amide resin was performed in accordance with AAV 1. The free amino group was acylated with 4 ml of a 0.4 M solution of bromoactic acid anhydride in DCM (2×15 min). The resin was washed with (DMF; 3×5.0 ml, MeOH; 3×5.0 ml, DCM; 3×5.0 ml) and then incubated for 2×30 min in 4 ml of a 5 M solution of n-butylamine. After washing the resin with (DMF; 3×5.0 ml, MeOH; 3×5.0 ml, DCM; 3×5.0 ml) the remaining synthesis of the peptide was performed in accordance with AAV 1.

Example 27

Synthesis of Ac-Phe-Arg(CH$_2$CH$_2$)-Pro-cha-Bta-Phe-NH$_2$ (150) [SEQ ID NO: 37]

After linear peptide synthesis in accordance with AAV 1, 700 mg of Ac-Phe-Orn-Pro-cha-Bta-Phe-NH$_2$ (62) were obtained as crude product. To 15 mg of this crude product (0.016 mmol) 39.7 mg (10 eq.) 2-methylthio-2-imidazolin-hydroiodine and 55.4 µl (20 eq.) DIPEA in 1 ml MeCN were added and stirred at 40° C. for one day. After removal of the solvent by using a rotary evaporator there was purification by HPLC and freeze drying after addition of 1 ml 0.1 N HCl and 0.5 ml MeCN, and 0.7 mg of compound 150 were obtained as white solid.
MS (ESI): m/z=960.9 [(M+H)$^+$].

Example 28

Efficacy of Compound 149 in a Model of Immune Complex Mediated Peritonitis

Immune complex mediated peritonitis is part of the pathological conditions of immune complex related diseases such as vasculitis, nephritis, arthritis, and farmer's disease. The corresponding animal model was described by Heller et al. (1999 Journal of Immunology 163: 985-994) and takes advantage of the pro-inflammatory effect of immune complexes formation from i.v. administration of the antigen and i.p. administration of the antibody.

BALB/c mice (6-8 weeks old) were treated i.v. with the compound 149 (1 mg/kg body weight in 200 µl vehicle) which is one in accordance with the present invention, 15 min before the initiation of the reverse passive Arthus reaction. Arthus reaction was induced by the administration of OVA (20 mg/kg i.v. in 200 µl PBS) and polyclonal anti-OVA Ab (rabbit; 800 µg/Maus i.p). After 6 h a peritoenal lavage with 2 ml PBS 0.1% BSA was done. The collected PE-cells were stained with DIFF-Quick. At least 20 visual fields (100× magnification) were analysed for the presence of neutrophils.

FIG. 1 clearly shows the reduction of the influx of pro-inflammatory cells into the peritoneum upon administration of compound 149.

Example 29

Efficacy of Compound 149 in a Model of C5a Induced Neutropenia

C5a induced neutropenia is a model for shock induced diseases (e.g. septic shock), where the systemic role of C5a such as neutropenia, blood pressure decrease, plays an important role. The reason for the decrease of the neutrophils in the circulation is their C5a triggered binding to the vessel walls. This process of neutrophil recruitment is also playing an important role in many other diseases like reperfusion injury. This model was also described by Short et al. (1999 British Journal of Pharmacology 125: 551-554).

Female Wistar rats were anaesthetized i.p. with ketamine (80 mg/kg) and xylazine (12 mg/kg). A catheter was introduced into the jugular veine and the animals were subjected to the following procedure:

1. Rats were pre-treated with vehicle or compound 149 which is a compound according to the invention, via i.v. infusion. A blood sample was taken one minute prior to that.
2. 10 min after compound infusion the rats were treated with 2 µg/kg hrC5a i.v. (2 µg/kg over 1 min)

Blood samples are taken shortly before and at various times after hrC5a administration.

3. Blood samples (about 0.2 ml) in lithium-heparin vials from the jugular veine were used for the differential blood count.

White Blood Cell Count:

White blood cell count was measured with a haematology-cell-counter.

Differential Cell Count:

Blood smears were prepared from the heparinized blood samples. Each sample is dehydrated with methanol prior to staining. After fixation the samples are stained with May Grünwald staining for 5 min. This is followed by a washing step with aqua dest. Subsequently, a Giemsa staining is performed for 2 min and the samples are washed again with aqua dest.

The differential cell count is determined as the sum of neutrophils, eosinophils, basophils, lymphocytes and monocytes of 100 cells. Then the percentage of the neutrophils in relation to all white blood cells is calculated.

Figure 2:
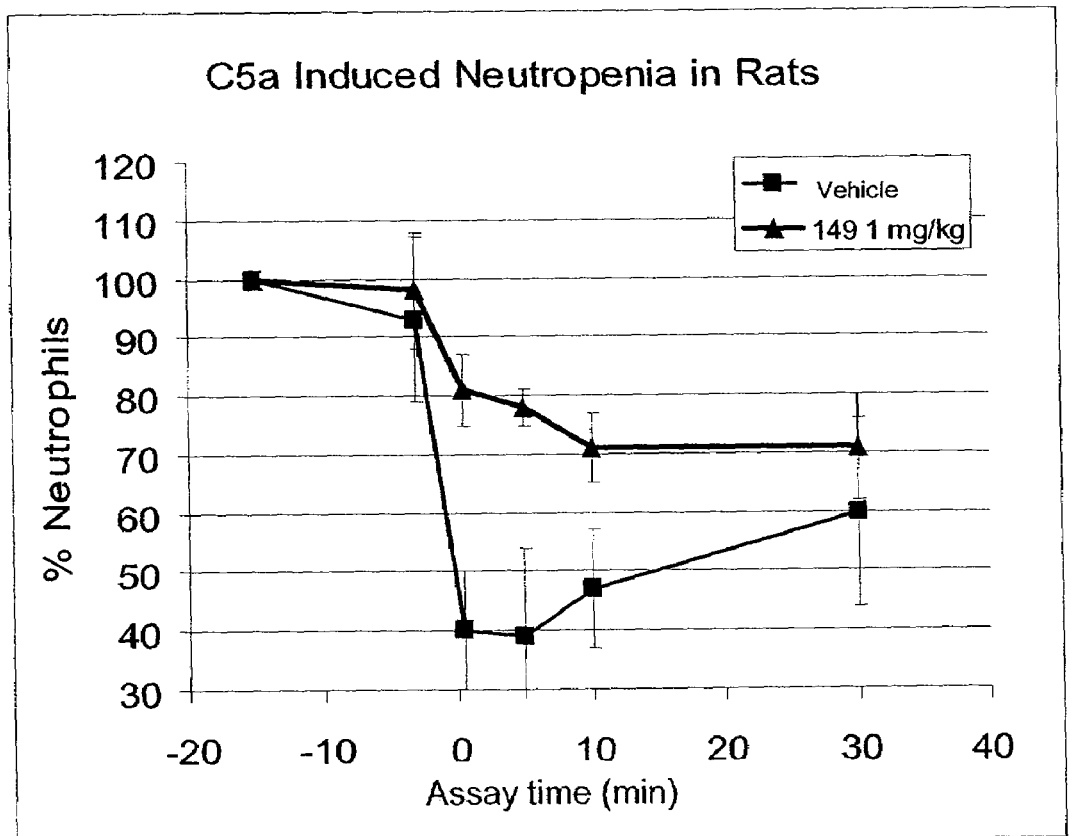
FIG. 2 shows a histogram indicating C5a-induced neutropenia in rats expressed as percentage of neutrophils over time upon administration of compound 149 and of the vehicle alone, respectively.

The result is presented in FIG. 2 and shows that the administration of compound 149 reduces significantly C5a-induced neutropenia, therefore, has the intended anti-inflammatory effect in this inflammatory model.

Example 30

Comparison of Activity of Peptides with Different C-Terminal Amino Acids

The assay system described in example 11 was used to measure the following activity of compounds 10 and 40:

| | | | | |
|---|---|---|---|---|
| 10 | Ac-Phe-[Orn-Pro-cha-Trp-Cit] | 897.5 | F |
| 40 | Ac-Phe-[Orn-Pro-cha-Trp-Arg] [SEQ ID NO: 68] | 896.6 | C |

Note the pronounced drop in activity when the charged arginine (activity class C; i. e. <=20 nM) is replaced by the uncharged citrulline (activity class F; i. e. >200 nM).

As the guanidine group (Arg) and the urea group (Cit) are bioisosteres and have similar space filling properties, the importance of a positive charge is evident, as also described in the prior art such as WO 03/033528. Additionally, this example demonstrates that the size of the substituents is not a sufficient criterion for predicting activity.

Another important aspect is the fact that citrulline is uncharged under physiological conditions, but is quite polar nevertheless, although not as polar as a charged guanidine. This becomes clear when the logP-values of different amino acids are calculated, as shown in the following:

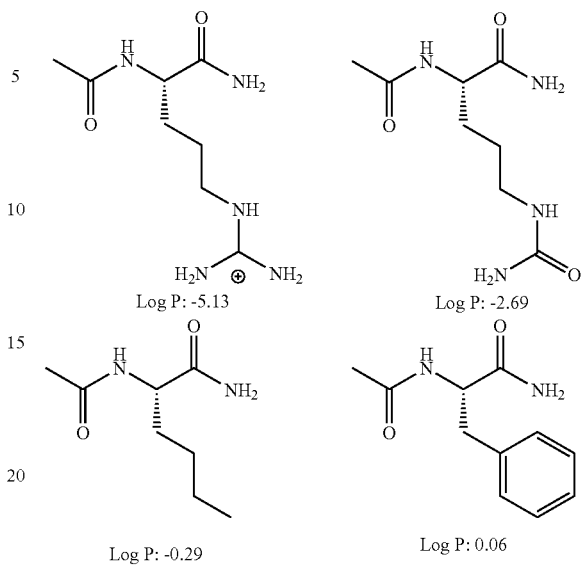

Log P: -5.13    Log P: -2.69

Log P: -0.29    Log P: 0.06

The logP value inicates the distribution coefficient of a compound between a water phase and an n-octanole phase. The more polar compounds are, the lower the logP value is. The logP values were calculated with the program Chemdraw (obtainable from Cambridge Soft, Cambridge, UK).

Due to the huge loss of activity already existent when the very polar guanidine group is replaced by the medium polar urea group, the one skilled in the art would not use an even more unpolar or even hydrophobic substitution instead of arginine, as under such conditions an even less activity would be expected.

The features of the invention disclosed in the above description, the claims or the drawings can individually or in any combination be essential to the practice of the invention in its various embodiments.

The invention claimed is:

1. The compound Hoo-Phe-Orn-Pro-hle-Pff-Phe-NH2, or a pharmaceutically acceptable salt thereof, wherein hle is the D-form.

2. A pharmaceutical composition comprising Hoo-Phe-Orn-Pro-hle-Pff-Phe-NH2, or a pharmaceutically acceptable salt thereof, and a pharmaceutically acceptable carrier, wherein hle is the D-form.

* * * * *

SEQUENCE LISTING

```
<160> NUMBER OF SEQ ID NOS: 76

<210> SEQ ID NO 1
<211> LENGTH: 8
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: X = D-Ala

<400> SEQUENCE: 1

Phe Lys Ala Xaa Ala Leu Xaa Tyr
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: X = N-methyl(D)ala

<400> SEQUENCE: 2

Phe Lys Ala Xaa Ala Leu Xaa Arg
1               5

<210> SEQ ID NO 3
<211> LENGTH: 8
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an ethyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: X = N-Methyl(D)ala group

<400> SEQUENCE: 3

Phe Lys Ala Xaa Ala Leu Xaa Arg
1               5

<210> SEQ ID NO 4
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with a methyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: X = phenylbutanoyl group

<400> SEQUENCE: 4

Phe Lys Pro Xaa Phe Xaa
1               5
```

```
<210> SEQ ID NO 5
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modifed with a methyl group
<220> FEATURE:
<221> NAME/KEY: MISC_FEATURE
<222> LOCATION: (4)..(4)
<223> OTHER INFORMATION: X = beta-cyclohexylalanine group
<220> FEATURE:
<221> NAME/KEY: MISC_FEATURE
<222> LOCATION: (5)..(5)
<223> OTHER INFORMATION: X = psi-CH2N(CH2CH2C6H5) group

<400> SEQUENCE: 5

Phe Lys Pro Xaa Xaa Arg
1               5

<210> SEQ ID NO 6
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modifed with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 6

Phe Xaa Pro Xaa Trp Arg
1               5

<210> SEQ ID NO 7
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 7

Phe Xaa Pro Xaa Trp Phe
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cycloheylalanine

<400> SEQUENCE: 8

Phe Xaa Pro Xaa Trp Met
1               5

<210> SEQ ID NO 9
<211> LENGTH: 7
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (3)..(3)
<223> OTHER INFORMATION: X = ornithine
<220> FEATURE:
<221> NAME/KEY: MISC_FEATURE
<222> LOCATION: (5)..(5)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: X = norleucine

<400> SEQUENCE: 9

Lys Phe Xaa Pro Xaa Trp Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 10

Phe Trp Xaa Pro Xaa Phe
```

<210> SEQ ID NO 11
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modifed with an acetyl group

<400> SEQUENCE: 11

Phe Trp Xaa Pro Xaa Phe
1               5

<210> SEQ ID NO 12
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with 2 methyl groups

<400> SEQUENCE: 12

Phe Trp Xaa Pro Xaa Phe
1               5

<210> SEQ ID NO 13
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine

<400> SEQUENCE: 13

Phe Trp Xaa Pro Xaa Phe
1               5

<210> SEQ ID NO 14
<211> LENGTH: 6

```
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with a methyl group

<400> SEQUENCE: 14

Phe Trp Xaa Pro Xaa Phe
1               5

<210> SEQ ID NO 15
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with a Bu-NH-CO group

<400> SEQUENCE: 15

Phe Trp Xaa Pro Xaa Phe
1               5

<210> SEQ ID NO 16
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 16

Phe Trp Xaa Ala Xaa Phe
1               5

<210> SEQ ID NO 17
<211> LENGTH: 6
<212> TYPE: PRT
```

```
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine modified with an acetyl group
<220> FEATURE:
<221> NAME/KEY: MISC_FEATURE
<222> LOCATION: (6)..(6)
<223> OTHER INFORMATION: modified with an acetyl group

<400> SEQUENCE: 17

Phe Trp Xaa Pro Xaa Phe
1               5

<210> SEQ ID NO 18
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 18

Phe Trp Xaa Pro Trp Phe
1               5

<210> SEQ ID NO 19
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with a phenyl-NH-CO group

<400> SEQUENCE: 19

Phe Trp Xaa Pro Xaa Phe
1               5

<210> SEQ ID NO 20
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
```

```
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with a Bu-O-CO group

<400> SEQUENCE: 20

Phe Trp Xaa Pro Xaa Phe
1               5

<210> SEQ ID NO 21
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = betacyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 21

Phe Trp Xaa Pro Lys Phe
1               5

<210> SEQ ID NO 22
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 22

Phe Trp Xaa Pro Arg Phe
1               5

<210> SEQ ID NO 23
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 23
```

```
<210> SEQ ID NO 24
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 24

Phe Trp Xaa Pro Trp Phe
1               5

<210> SEQ ID NO 25
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 25

Phe Trp Xaa Pro Arg Phe
1               5

<210> SEQ ID NO 26
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 26

Phe Trp Xaa Ser Xaa Phe
1               5

<210> SEQ ID NO 27
<211> LENGTH: 6
<212> TYPE: PRT
<213> ORGANISM: Artificial Sequence
```

(preceding continued entry)

```
Phe Trp Xaa Pro Gln Phe
1               5
```

```
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = cyclohexylglycine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 27

Phe Trp Xaa Pro Xaa Phe
1               5

<210> SEQ ID NO 28
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = homo-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 28

Phe Trp Xaa Pro Xaa Phe
1               5

<210> SEQ ID NO 29
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 29

Phe Xaa Xaa Pro Trp Phe
1               5

<210> SEQ ID NO 30
<211> LENGTH: 6
<212> TYPE: PRT
<213> ORGANISM: Artificial Sequence
<220> FEATURE:
```

```
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 30

Phe Xaa Ser Xaa Trp Phe
1               5

<210> SEQ ID NO 31
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = cyclohexylglycine

<400> SEQUENCE: 31

Phe Xaa Pro Xaa Trp Phe
1               5

<210> SEQ ID NO 32
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 32

Phe Xaa Xaa Pro Arg Phe
1               5

<210> SEQ ID NO 33
<211> LENGTH: 6
<212> TYPE: PRT
<213> ORGANISM: Artificial Sequence
<220> FEATURE:
<223> OTHER INFORMATION: oligopeptide with antagonistic activity at the
```

```
       C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: modified with an acetamidomethyl group
<220> FEATURE:
<221> NAME/KEY: MISC_FEATURE
<222> LOCATION: (6)..(6)
<223> OTHER INFORMATION: modified with an acetyl group

<400> SEQUENCE: 33

Phe Xaa Xaa Pro Cys Phe
1               5

<210> SEQ ID NO 34
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = homo-cyclohexylalanine

<400> SEQUENCE: 34

Phe Xaa Pro Xaa Trp Phe
1               5

<210> SEQ ID NO 35
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = 2-amino-5-diethylamino-pentanoic acid
<220> FEATURE:
<221> NAME/KEY: MISC_FEATURE
<222> LOCATION: (6)..(6)
<223> OTHER INFORMATION: modified with an acetyl group

<400> SEQUENCE: 35

Phe Trp Xaa Pro Xaa Phe
1               5

<210> SEQ ID NO 36
<211> LENGTH: 6
<212> TYPE: PRT
```

```
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 36

Phe Xaa Pro Xaa Trp Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: modified with 2 methyl groups
<220> FEATURE:
<221> NAME/KEY: MISC_FEATURE
<222> LOCATION: (6)..(6)
<223> OTHER INFORMATION: modified with an acetyl group

<400> SEQUENCE: 37

Phe Xaa Xaa Pro Arg Phe
1               5

<210> SEQ ID NO 38
<211> LENGTH: 7
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = benzothienylalanine
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: modified with an acetyl group

<400> SEQUENCE: 38

Cys Phe Xaa Xaa Pro Cys Phe
1               5
```

```
<210> SEQ ID NO 39
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 39

Phe Xaa Pro Xaa Trp Leu
1               5

<210> SEQ ID NO 40
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 40

Phe Xaa Pro Xaa Trp Phe
1               5

<210> SEQ ID NO 41
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 41

Phe Xaa Xaa Pro Ala Phe
1               5

<210> SEQ ID NO 42
```

```
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = homoleucine
<220> FEATURE:
<221> NAME/KEY: MISC_FEATURE
<222> LOCATION: (6)..(6)
<223> OTHER INFORMATION: modified with an acetyl group

<400> SEQUENCE: 42

Phe Xaa Xaa Pro Arg Phe
1               5

<210> SEQ ID NO 43
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = Phe(3-Cl)
<220> FEATURE:
<221> NAME/KEY: MISC_FEATURE
<222> LOCATION: (3)..(3)
<223> OTHER INFORMATION: X = homo-leucine
<220> FEATURE:
<221> NAME/KEY: MISC_FEATURE
<222> LOCATION: (6)..(6)
<223> OTHER INFORMATION: modified with an acetyl group

<400> SEQUENCE: 43

Phe Xaa Xaa Pro Arg Phe
1               5

<210> SEQ ID NO 44
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 44

Phe Xaa Xaa Pro His Phe
1               5

<210> SEQ ID NO 45
<211> LENGTH: 6
```

```
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = homo-cyclohexylalanine

<400> SEQUENCE: 45

Phe Xaa Pro Xaa Trp Phe
1               5

<210> SEQ ID NO 46
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = homo-leucine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 46

Phe Phe Xaa Pro Xaa Phe
1               5

<210> SEQ ID NO 47
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = homo-leucine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 47

Phe Trp Xaa Pro Xaa Phe
1               5

<210> SEQ ID NO 48
<211> LENGTH: 6
<212> TYPE: PRT
```

```
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = D-isoleucine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 48

Phe Trp Xaa Pro Xaa Phe
1               5

<210> SEQ ID NO 49
<211> LENGTH: 7
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine

<400> SEQUENCE: 49

Phe Xaa Xaa Pro Xaa Phe Gly
1               5

<210> SEQ ID NO 50
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 50

Phe Xaa Ser Xaa Trp Phe
1               5

<210> SEQ ID NO 51
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
```

```
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 51

Phe Trp Xaa Pro Ser Phe
1               5

<210> SEQ ID NO 52
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with an acetyl group

<400> SEQUENCE: 52

Phe Trp Xaa Pro Glu Phe
1               5

<210> SEQ ID NO 53
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = N(nBu)-CH2-CO
<220> FEATURE:
<221> NAME/KEY: MISC_FEATURE
<222> LOCATION: (6)..(6)
<223> OTHER INFORMATION: modified with an acetyl group

<400> SEQUENCE: 53

Phe Trp Xaa Pro Xaa Phe
1               5

<210> SEQ ID NO 54
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl goup
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
```

```
<222> LOCATION: (6)..(6)
<223> OTHER INFORMATION: X = D-arginine

<400> SEQUENCE: 54

Phe Lys Pro Xaa Trp Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: X = D-arginine

<400> SEQUENCE: 55

Phe Xaa Pro Xaa Trp Xaa
1               5

<210> SEQ ID NO 56
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 56

Phe Xaa Pro Xaa Trp Arg
1               5

<210> SEQ ID NO 57
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
```

<223> OTHER INFORMATION: X = beta-cyclohexylalanine

<400> SEQUENCE: 57

Phe Lys Pro Xaa Trp Arg
1               5

<210> SEQ ID NO 58
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with a methyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: X = D-arginine

<400> SEQUENCE: 58

Phe Lys Pro Xaa Trp Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: X = D-arginine

<400> SEQUENCE: 59

Phe Lys Pro Xaa Trp Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: X = D-arginine

```
<400> SEQUENCE: 60

Phe Lys Pro Xaa Trp Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 61

Phe Xaa Pro Xaa Trp Arg
1               5

<210> SEQ ID NO 62
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with 2 methyl groups

<400> SEQUENCE: 62

Phe Xaa Pro Xaa Trp Arg
1               5

<210> SEQ ID NO 63
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
```

-continued

```
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with 2 methyl groups

<400> SEQUENCE: 63

Phe Xaa Pro Xaa Trp Arg
1               5

<210> SEQ ID NO 64
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with a 4-amidine group

<400> SEQUENCE: 64

Phe Xaa Pro Xaa Trp Phe
1               5

<210> SEQ ID NO 65
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 65

Phe Xaa Pro Xaa Trp Lys
1               5

<210> SEQ ID NO 66
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
```

```
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (6)..(6)
<223> OTHER INFORMATION: modified with 2 methyl groups

<400> SEQUENCE: 66

Phe Xaa Pro Xaa Trp Arg
1               5

<210> SEQ ID NO 67
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = cyclohexylalanine

<400> SEQUENCE: 67

Phe Xaa Pro Xaa Trp Ala
1               5

<210> SEQ ID NO 68
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 68

Phe Xaa Pro Xaa Trp Arg
1               5

<210> SEQ ID NO 69
<211> LENGTH: 6
<212> TYPE: PRT
<213> ORGANISM: Artificial Sequence
<220> FEATURE:
<223> OTHER INFORMATION: oligopeptide with antagonistic activity at the
```

```
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 69

Ala Xaa Pro Xaa Trp Arg
1               5

<210> SEQ ID NO 70
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = D-alanine

<400> SEQUENCE: 70

Phe Xaa Pro Xaa Trp Arg
1               5

<210> SEQ ID NO 71
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 71

Phe Xaa Pro Xaa Ala Arg
1               5

<210> SEQ ID NO 72
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
```

```
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 72

Phe Xaa Pro Xaa Trp Ala
1               5

<210> SEQ ID NO 73
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine
<220> FEATURE:
<221> NAME/KEY: MISC_FEATURE
<222> LOCATION: (6)..(6)
<223> OTHER INFORMATION: modified with an acetyl group

<400> SEQUENCE: 73

Arg Trp Xaa Pro Xaa Phe
1               5

<210> SEQ ID NO 74
<211> LENGTH: 8
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with an acetyl group
<220> FEATURE:
<221> NAME/KEY: MISC_FEATURE
<222> LOCATION: (4)..(4)
<223> OTHER INFORMATION: X = beta-cyclohexylalanine
<220> FEATURE:
<221> NAME/KEY: MISC_FEATURE
<222> LOCATION: (7)..(7)
<223> OTHER INFORMATION: X = D-alanine

<400> SEQUENCE: 74

Phe Lys Ala Xaa Ala Leu Xaa Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
```

```
<221> NAME/KEY: MISC_FEATURE
<222> LOCATION: (2)..(2)
<223> OTHER INFORMATION: X = ornithine
<220> FEATURE:
<221> NAME/KEY: MISC_FEATURE
<222> LOCATION: (4)..(4)
<223> OTHER INFORMATION: X = beta-cyclohexylalanine

<400> SEQUENCE: 75

Phe Xaa Pro Xaa Trp Phe
1               5

<210> SEQ ID NO 76
<211> LENGTH: 7
<212> TYPE: PRT
<213> ORGANISM: Artificial Sequence
<220> FEATURE:
<223> OTHER INFORMATION: oligopeptide with antagonistic activity at the
      C5a receptor
<220> FEATURE:
<221> NAME/KEY: MISC_FEATURE
<222> LOCATION: (1)..(1)
<223> OTHER INFORMATION: modified with a rink-amide group
<220> FEATURE:
<221> NAME/KEY: MISC_FEATURE
<222> LOCATION: (2)..(2)
<223> OTHER INFORMATION: X = benzothienylalanine
<220> FEATURE:
<221> NAME/KEY: MISC_FEATURE
<222> LOCATION: (3)..(3)
<223> OTHER INFORMATION: X = beta-cyclohexylalanine
<220> FEATURE:
<221> NAME/KEY: MISC_FEATURE
<222> LOCATION: (5)..(5)
<223> OTHER INFORMATION: X = ornithine

<400> SEQUENCE: 76

Phe Xaa Xaa Pro Xaa Phe Gly
1               5
```